US008362084B2

(12) United States Patent
Schreiber et al.

(10) Patent No.: US 8,362,084 B2
(45) Date of Patent: Jan. 29, 2013

(54) HISTONE DEACETYLASES, AND USES RELATED THERETO

(75) Inventors: Stuart L. Schreiber, Boston, MA (US); Jack Taunton, Somerville, MA (US); Christian A. Hassig, Somerville, MA (US); Timothy F. Jamison, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/030,086

(22) Filed: Feb. 17, 2011

(65) Prior Publication Data

US 2011/0218154 A1    Sep. 8, 2011

Related U.S. Application Data

(60) Continuation of application No. 12/196,878, filed on Aug. 22, 2008, now Pat. No. 7,994,362, which is a continuation of application No. 10/919,217, filed on Aug. 16, 2004, which is a division of application No. 08/624,735, filed on Mar. 26, 1996, now Pat. No. 6,777,217.

(51) Int. Cl.
    *A61K 31/19*  (2006.01)
(52) U.S. Cl. .................................................. 514/575
(58) Field of Classification Search ................. 562/621; 514/575
    See application file for complete search history.

(56) References Cited

U.S. PATENT DOCUMENTS

| 4,608,390 A * | 8/1986 | Summers, Jr. ................ 514/575 |
| 4,631,211 A | 12/1986 | Houghten |
| 4,639,462 A | 1/1987 | Kramer et al. |
| 4,683,195 A | 7/1987 | Mullis et al. |
| 4,683,202 A | 7/1987 | Mullis |
| 4,820,828 A | 4/1989 | Demers et al. |
| 4,833,080 A | 5/1989 | Brent et al. |
| 4,861,798 A * | 8/1989 | Tramposch et al. .......... 514/575 |
| 5,045,538 A | 9/1991 | Schneider et al. |
| 5,059,698 A | 10/1991 | Schulthess et al. |
| 5,096,815 A | 3/1992 | Ladner et al. |
| 5,143,854 A | 9/1992 | Pirrung et al. |
| 5,175,191 A * | 12/1992 | Marks et al. .................. 514/575 |
| 5,176,996 A | 1/1993 | Hogan et al. |
| 5,198,346 A | 3/1993 | Ladner et al. |
| 5,223,409 A | 6/1993 | Ladner et al. |
| 5,225,173 A | 7/1993 | Wai |
| 5,238,781 A | 8/1993 | Schadeli |
| 5,256,775 A | 10/1993 | Froehler |
| 5,264,564 A | 11/1993 | Matteucci |
| 5,283,317 A | 2/1994 | Saifer et al. |
| 5,288,514 A | 2/1994 | Ellman |
| 5,304,121 A | 4/1994 | Sahatjian |
| 5,328,470 A | 7/1994 | Nabel et al. |
| 5,359,115 A | 10/1994 | Campbell et al. |
| 5,362,899 A | 11/1994 | Campbell |
| 5,393,741 A | 2/1995 | Pettersen et al. |
| 5,440,016 A | 8/1995 | Blondelle et al. |
| 5,480,971 A | 1/1996 | Houghten et al. |
| 5,659,016 A | 8/1997 | Nakamura et al. |
| 5,700,811 A | 12/1997 | Breslow et al. |
| 5,763,182 A | 6/1998 | Nakamura et al. |
| 5,837,313 A | 11/1998 | Ding et al. |
| 5,886,026 A | 3/1999 | Hunter et al. |
| 5,891,507 A | 4/1999 | Jayaraman |
| 6,030,945 A | 2/2000 | Ashkenazi |
| 6,068,987 A | 5/2000 | Dulski et al. |
| 6,071,305 A | 6/2000 | Brown et al. |
| 6,099,562 A | 8/2000 | Ding et al. |
| 6,153,252 A | 11/2000 | Hossainy et al. |
| 6,190,619 B1 | 2/2001 | Kilcoin et al. |
| 6,195,612 B1 | 2/2001 | Pack-Harris |
| 6,203,551 B1 | 3/2001 | Wu |
| 6,231,600 B1 | 5/2001 | Zhong |
| 6,248,127 B1 | 6/2001 | Shah et al. |
| 6,251,136 B1 | 6/2001 | Guruwaiya et al. |
| 6,258,121 B1 | 7/2001 | Yang et al. |
| 6,273,913 B1 | 8/2001 | Wright et al. |
| 6,428,960 B1 | 8/2002 | Clark et al. |
| 6,495,719 B2 | 12/2002 | Lan-Hargest et al. |
| 6,512,123 B2 | 1/2003 | Grossmann et al. |
| 6,517,889 B1 | 2/2003 | Jayaraman |
| 6,541,661 B1 * | 4/2003 | Delorme et al. ............. 560/318 |
| 6,777,217 B1 | 8/2004 | Schreiber et al. |
| 6,897,220 B2 | 5/2005 | Delorme et al. |
| 6,960,685 B2 | 11/2005 | Watkins et al. |
| 7,244,853 B2 | 7/2007 | Schreiber et al. |
| 7,250,504 B2 | 7/2007 | Grozinger et al. |
| 7,994,362 B2 * | 8/2011 | Schreiber et al. ........... 562/621 |
| 8,076,116 B2 | 12/2011 | Grozinger et al. |
| 2001/0027340 A1 | 10/2001 | Wright et al. |
| 2003/0004209 A1 | 1/2003 | Hunter et al. |

(Continued)

FOREIGN PATENT DOCUMENTS

DE    32 422 252    1/1987
EP    0 259 149 A2    3/1988

(Continued)

OTHER PUBLICATIONS

Tanaka et al, Chem. Pharm. Bull., 31(8), 2810-2819, 1983.*
U.S. Appl. No. 60/289,850, filed May 9, 2001, Schreiber et al.
U.S. Appl. No. 60/664,470, filed Mar. 22, 2005, Bradner et al.
U.S. Appl. No. 60/773,172, filed Feb. 14, 2006, Bradner et al.
U.S. Appl. No. 60/773,510, filed Feb. 14, 2006, Bradner et al.
International Search Report and Written Opinion for PCT/US2010/002220 mailed Apr. 27, 2011.
Invitation to Pay Additional Fees for PCT/US2007/062145 mailed Oct. 29, 2007.

(Continued)

Primary Examiner — Shailendra Kumar
(74) Attorney, Agent, or Firm — Wolf, Greenfield & Sacks, P.C.; C. Hunter Baker; Robin A. Weatherhead

(57) ABSTRACT

The present invention concerns the discovery that proteins encoded by a family of genes, termed here HDx-related genes, which are involved in the control of chromatin structure and, thus in transcription and translation. The present invention makes available compositions and methods that can be utilized, for example to control cell proliferation and differentiation in vitro and in vivo.

13 Claims, 22 Drawing Sheets

U.S. PATENT DOCUMENTS

| | | |
|---|---|---|
| 2003/0129724 A1 | 7/2003 | Grozinger et al. |
| 2003/0187027 A1 | 10/2003 | Schreiber et al. |
| 2003/0216345 A1 | 11/2003 | Nakanishi et al. |
| 2004/0072849 A1 | 4/2004 | Schreiber et al. |
| 2004/0087631 A1 | 5/2004 | Bacopoulos et al. |
| 2004/0092598 A1 | 5/2004 | Watkins et al. |
| 2004/0127522 A1 | 7/2004 | Chiao et al. |
| 2004/0138153 A1 | 7/2004 | Ramesh et al. |
| 2005/0014839 A1 | 1/2005 | Kozikowski et al. |
| 2005/0267037 A1 | 12/2005 | Anderson et al. |
| 2005/0287629 A1 | 12/2005 | Grozinger et al. |
| 2006/0020131 A1 | 1/2006 | Raeppel et al. |
| 2006/0079528 A1 | 4/2006 | Finn et al. |
| 2006/0239909 A1 | 10/2006 | Anderson et al. |
| 2007/0093413 A1 | 4/2007 | Schreiber et al. |
| 2008/0269245 A1 | 10/2008 | Schreiber et al. |
| 2008/0300205 A1 | 12/2008 | Tsai et al. |
| 2009/0036318 A1 | 2/2009 | Grozinger et al. |
| 2009/0209590 A1 | 8/2009 | Mazitschek et al. |
| 2009/0221474 A1 | 9/2009 | Schreiber et al. |
| 2009/0305384 A1 | 12/2009 | Grozinger et al. |
| 2009/0312363 A1 | 12/2009 | Bradner et al. |
| 2010/0056588 A1 | 3/2010 | Bradner et al. |
| 2010/0137196 A1 | 6/2010 | Schreiber et al. |
| 2011/0172303 A1 | 7/2011 | Tang et al. |

FOREIGN PATENT DOCUMENTS

| | | |
|---|---|---|
| EP | 0 322 335 A1 | 6/1989 |
| EP | 0 323 590 A2 | 7/1989 |
| EP | 0 331 524 A2 | 9/1989 |
| EP | 0 458 131 A1 | 11/1991 |
| EP | 0 708 112 A1 | 4/1996 |
| EP | 07872648.6 | 4/2011 |
| EP | 07757000.0 | 5/2011 |
| GB | 2 169 599 A | 7/1986 |
| JP | 8-311321 A | 11/1996 |
| JP | 9-124918 A | 5/1997 |
| JP | 2004-043446 A | 2/2004 |
| WO | WO 91/00257 A1 | 1/1991 |
| WO | WO 91/07087 A1 | 5/1991 |
| WO | WO 92/09690 A2 | 6/1992 |
| WO | WO 92/10092 A1 | 6/1992 |
| WO | WO 92/15694 A1 | 9/1992 |
| WO | WO 93/05807 A2 | 4/1993 |
| WO | WO 93/07148 A1 | 4/1993 |
| WO | WO 93/07867 A1 | 4/1993 |
| WO | WO 93/09668 A1 | 5/1993 |
| WO | WO 93/19778 A1 | 10/1993 |
| WO | WO 93/20242 A1 | 10/1993 |
| WO | WO 94/08051 A1 | 4/1994 |
| WO | WO 94/10300 A1 | 5/1994 |
| WO | WO 97/11366 A1 | 3/1997 |
| WO | WO 97/35990 A2 | 10/1997 |
| WO | WO 98/16830 A2 | 4/1998 |
| WO | WO 98/47869 A1 | 10/1998 |
| WO | WO 98/55449 A1 | 12/1998 |
| WO | WO 00/20415 A1 | 4/2000 |
| WO | WO 00/34313 A1 | 6/2000 |
| WO | WO 00/35911 A1 | 6/2000 |
| WO | WO 00/36132 A1 | 6/2000 |
| WO | WO 00/44709 A2 | 8/2000 |
| WO | WO 02/089782 A1 | 11/2002 |
| WO | WO 04/001059 A2 | 12/2003 |
| WO | WO 2004/046104 A2 | 6/2004 |
| WO | WO 2004/062601 A2 | 7/2004 |
| WO | WO 2004/103369 A1 | 12/2004 |
| WO | WO 2005/007091 A2 | 1/2005 |
| WO | WO 2005/012247 A1 | 2/2005 |
| WO | WO 2005/018578 A2 | 3/2005 |
| WO | WO 2005/066151 A2 | 7/2005 |
| WO | WO 2005/080335 A1 | 9/2005 |
| WO | WO 2006/060676 A1 | 6/2006 |
| WO | WO 2006/060809 A2 | 6/2006 |
| WO | WO 2007/111948 A2 | 10/2007 |
| WO | WO 2008/040934 A1 | 4/2008 |
| WO | WO 2009/063054 A1 | 5/2009 |
| WO | WO 2011/019393 A2 | 2/2011 |

OTHER PUBLICATIONS

International Search Report and Written Opinion for PCT/US2007/062145 mailed Jun. 24, 2008.
International Preliminary Report on Patentability for PCT/US2007/062145 mailed Aug. 28, 2008.
Invitation to Pay Additional Fees for PCT/US2007/062152 mailed Dec. 7, 2007.
International Search Report and Written Opinion for PCT/US2007/062152 mailed Oct. 7, 2008.
International Search Report and Written Opinion for PCT/US2007/062152 mailed Oct. 14, 2008.
International Preliminary Report on Patentability for PCT/US2007/062152 mailed Mar. 19, 2009.
International Search Report and Written Opinion for PCT/US2009/004235 mailed Mar. 4, 2010.
International Preliminary Report on Patentability for PCT/US2009/004235 mailed Feb. 3, 2011.
Supplementary European Search Report for EP 06748614.2 mailed Oct. 16, 2009.
International Search Report and Written Opinion for PCT/US2006/010676 mailed Jul. 14, 2008.
International Preliminary Report on Patentability for PCT/US2006/010676 mailed Mar. 19, 2009.
International Search Report and Written Opinion for PCT/US2007/010587 mailed Jan. 29, 2008.
International Preliminary Report on Patentability for PCT/US2007/010587 mailed Nov. 13, 2008.
International Search Report for PCT/US2002/014835 mailed Dec. 20, 2002.
Written Opinion for PCT/US2002/014835 mailed Aug. 8, 2003.
International Preliminary Exam Report for PCT/US2002/014835 mailed Jun. 4, 2004.
Invitation to Pay Additional Fees for PCT/US1997/005275 mailed Nov. 21, 1997.
International Search Report for PCT/US1997/005275 mailed Feb. 16, 1998.
Written Opinion for PCT/US1997/005275 mailed Mar. 5, 1998.
International Preliminary Examination Report for PCT/US1997/005275 mailed Jul. 3, 1998.
Office Communication, mailed Oct. 15, 2008, for U.S. Appl. No. 11/386,959.
Office Communication, mailed Jul. 21, 2009, for U.S. Appl. No. 11/386,959.
Advisory Action, mailed Nov. 17, 2009, for U.S. Appl. No. 11/386,959.
Office Communication, mailed Nov. 28, 2005, for U.S. Appl. No. 10/621,276.
Office Communication, mailed Aug. 8, 2006, for U.S. Appl. No. 10/621,276.
Notice of Allowance, mailed Mar. 6, 2007, for U.S. Appl. No. 10/621,276.
Office Communication, mailed Sep. 16, 2009, for U.S. Appl. No. 11/879,466.
Notice of Allowance, mailed Feb. 4, 2010, for U.S. Appl. No. 11/879,466.
Office Communication, mailed Jan. 21, 1998, for U.S. Appl. No. 08/624,735.
Office Communication, mailed Jan. 17, 2001, for U.S. Appl. No. 08/624,735.
Office Communication, mailed Oct. 10, 2001, for U.S. Appl. No. 08/624,735.
Office Communication, mailed Oct. 16, 2002, for U.S. Appl. No. 08/624,735.
Office Communication, mailed Aug. 12, 2003, for U.S. Appl. No. 08/624,735.
Notice of Allowance, mailed Apr. 13, 2004, for U.S. Appl. No. 08/624,735.
Office Communication, mailed May 6, 2009, for U.S. Appl. No. 10/919,217.
Office Communication, mailed Mar. 4, 2010, for U.S. Appl. No. 10/919,217.
Office Communication, mailed Oct. 14, 2010, for U.S. Appl. No. 10/919,217.

Office Communication, mailed Apr. 8, 2010, for U.S. Appl. No. 12/196,878.
Office Communication, mailed Aug. 10, 2010, for U.S. Appl. No. 12/196,878.
Office Communication, mailed Jan. 18, 2011, for U.S. Appl. No. 12/196,878.
Office Communication, mailed Aug. 5, 2010, for U.S. Appl. No. 12/196,946.
Office Communication, mailed Dec. 28, 2010, for U.S. Appl. No. 12/196,946.
Advisory Action, mailed Apr. 14, 2011, for U.S. Appl. No. 12/196,946.
Office Communication, mailed Jun. 30, 2003, for U.S. Appl. No. 09/800,187.
Office Communication, mailed Apr. 13, 2004, for U.S. Appl. No. 09/800,187.
Notice of Allowance, mailed Apr. 13, 2007, for U.S. Appl. No. 10/964,313.
Office Communication, mailed Sep. 17, 2009, for U.S. Appl. No. 11/831,303.
Office Communication, mailed Apr. 2, 2010, for U.S. Appl. No. 12/370,390.
Office Communication, mailed Oct. 8, 2010, for U.S. Appl. No. 12/370,390.
Office Communication, mailed Apr. 28, 2011, for U.S. Appl. No. 12/370,390.
GenBank Submission: NIH/NCBI, Accession No. AAA68286; GI: 348052, Henkin et al., Jun. 14, 1995.
GenBank Submission: NIH/NCBI, Accession No. AAD29046, Grozinger et al.; May 6, 1999.
GenBank Submission: NIH/NCBI, Accession No. AAF73428, Buggy et al.; Jun. 1, 2000.
GenBank Submission: NIH/NCBI, Accession No. AAP63491; Kieliszewski; Jun. 12, 2003.
GenBank Submission; NIH/NCBI, Accession No. AB006626; Gi:2564323, Ohara et al.; Mar. 18, 1998.
GenBank Submission; NIH/NCBI, Accession No. AB006626; Gi:6635126, Ohara et al.; Dec. 25, 1999.
GenBank Submission; NIH/NCBI, Accession No. AF039241, Swensen.; Mar. 11, 2009.
GenBank Submission; NIH/NCBI, Accession No. AF132607, Grozinger et al.; May 6, 1999.
GenBank Submission; NIH/NCBI, Accession No. AF230097, Hu et al., May 31, 2000.
GenBank Submission; NIH/NCBI, Accession No. AF245664, Buggy et al.; Jun. 1, 2000.
GenBank Submission; NIH/NCBI, Accession No. AJ011972, Strom et al.; Oct. 19, 1998.
GenBank Submission: NIH/NCBI, Accession No. BAA25526; GI: 3043724, Ohara et al., Apr. 10, 1998.
GenBank Submission; NIH/NCBI, Accession No. BC009676, Strausberg et al.; Jul. 15, 2006.
GenBank Submission: NIH/NCBI, Accession No. BC111735, Strausberg et al.; Jan. 17, 2006.
GenBank Submission; NIH/NCBI, Accession No. CAA09893.1, Strom et al.; Oct. 7, 2008.
GenBank Submission; NIH/NCBI, Accession No. NM_006044.2, Dhakal et al.; Mar. 15, 2009.
GenBank Submission; NIH/NCBI, Accession No. NM_001015053.1, Seo et al.; Mar. 15, 2009.
GenBank Submission; NIH/NCBI, Accession No. NM_006037.3, Chabane et al.; Mar. 29, 2009.
GenBank Submission; NIH/NCBI, Accession No. NM_014707, Muralidhar et al.; Mar. 11, 2011.
GenBank Submission; NIH/NCBI, Accession No. NM_018486, Bailey et al.; Mar. 11, 2011.
GenBank Submission; NIH/NCBI, Accession No. NM_032019, Bailey et al.; Mar. 12, 2011.
GenBank Submission; NIH/NCBI, Accession No. NM_058176, Muralidhar et al.; Feb. 27, 2011.
GenBank Submission; NIH/NCBI, Accession No. NM_058177, Tam et al.; May 7, 2010.
GenBank Submission; NIH/NCBI, Accession No. NM_178423, Muralidhar et al.; Mar. 13, 2011.
GenBank Submission; NIH/NCBI, Accession No. NM_178425, Muralidhar et al.; Feb. 27, 2011.
GenBank Submission; NIH/NCBI, Accession No. NP_001518, Campos et al.; Mar. 13, 2011.
GenBank Submission; NIH/NCBI, Accession No. NP_004955, Dong et al; Mar. 27, 2011.
GenBank Submission; NIH/NCBI, Accession No. NP_005465, Huynh; Mar. 11, 2011.
GenBank Submission; NIH/NCBI, Accession No. NP_006035; Aldana-Masangkay et al.; Mar. 13, 2011.
GenBank Submission; NIH/NCBI, Accession No. 015739, Loomis et al.; Oct. 31, 2006.
GenBank Submission: NIH/NCBI, Accession No. P56524; GI: 3024889, Ohara et al., Dec. 15, 1998.
GenBank Submission: NIH/NCBI, Accession No. Q48935; GI: 3023317, Sakurada et al., Apr. 20, 2010.
GenBank Submission; NIH/NCBI, Accession No. Q9Z2V5, Verdel et al.; Mar. 2, 2010.
GenBank Submission; NIH/NCBI, Accession No. Q9Z2V6, Verdel et aL; Mar. 2, 2010.
GenBank Submission; NIH/NCBI, Accession No. R64669, Wilson; May 26, 1995.
GenBank Submission; NIH/NCBI, Accession No. U31814, Yang et al.; Nov. 13, 1996.
GenBank Submission; NIH/NCBI, Accession No. U31814, Yang et al.; Nov. 14, 1996.
NCBI annotation project, GenBank Accession No. XM_002252, Oct. 16, 2001.
NCBI annotation project, GenBank Accession No. XM_004963, Feb. 9, 2001.
NCBI annotation project, GenBank Accession No. XM_004963.2, Oct. 16, 2001.
NCBI annotation project, GenBank Accession No. XM_007047, Nov. 16, 2000.
NCBI annotation project, GenBank Accession No. XM_008359, Oct. 16, 2001.
NCBI annotation project, GenBank Accession No. XP_002252, Oct. 16, 2001.
NCBI annotation project, GenBank Accession No. XP_008359.2, Feb. 10, 2001.
[No Author Listed] Targeting the aggresome with an HDAC6 inhibitor in combination with velcade for myeloma therapy. Cancer Biology and Therapy. 2005;4(7):i-iv.
Abremski et al., Bacteriophage P1 site-specific recombination. Purification and properties of the Cre recombinase protein. J Biol Chem. Feb. 10, 1984;259(3):1509-14.
Adams et al., Initial assessment of human gene diversity and expression patterns based upon 83 million nucleotides of cDNA sequence. Nature. Sep. 28, 1995;377(6547 Suppl):3-174.
Adams, The proteasome: a suitable antineoplastic target. Nat Rev Cancer. May 2004;4(5):349-60.
Afshar et al., Characterization of a human gene with sequence homology to *Saccharomyces cerevisiae* SIR2. Gene. Jun. 24, 1999;234(1):161-8.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Anderson et al., Analytical Techniques in Combinatorial Chemistry: MAS CH Correlation in Solvent-Swollen Resin. J Org Chem. 1995;60:2650-51.
Anklesaria et al., Engraftment of a clonal bone marrow stromal cell line in vivo stimulates hematopoietic recovery from total body irradiation. Proc Natl Acad Sci U S A. Nov. 1987;84(21):7681-5.
Antón et al., Intracellular localization of proteasomal degradation of a viral antigen. J Cell Biol. Jul. 12, 1999;146(1):113-24.

Antonjuk et al., Asymmetric Induction in the Additions of Anions of Allylic Sulfoxides to Benzaldehyde. Aust J Chem. 1980;33:2635-51.

Aparicio et al., Modifiers of position effect are shared between telomeric and silent mating-type loci in S. cerevisiae. Cell. Sep. 20, 1991;66(6):1279-87.

Arkin et al., An algorithm for protein engineering: simulations of recursive ensemble mutagenesis. Proc Natl Acad Sci U S A. Aug. 15, 1992;89(16):7811-5.

Attal et al., Single versus double autologous stem-cell transplantation for multiple myeloma. N Engl J Med. Dec. 25, 2003;349(26):2495-502.

Auffray et al., [IMAGE: molecular integration of the analysis of the human genome and its expression.] C R Acad Sci III. Feb. 1995;318(2):263-72. French.

Baer et al., Eukaryotic RNA polymerase II binds to nucleosome cores from transcribed genes. Nature. Feb. 10, 1983;301(5900):482-8.

Ballestar et al., Methyl-CpG-binding proteins. Targeting specific gene repression. Eur J Biochem. Jan. 2001;268(1):1-6.

Barbas et al., Semisynthetic combinatorial antibody libraries: a chemical solution to the diversity problem. Proc Natl Acad Sci U S A. May 15, 1992;89(10):4457-61.

Bartel et al., Elimination of false positives that arise in using the two-hybrid system. Biotechniques. Jun. 1993;14(6):920-4.

Beck-Sickinger et al., Neuropeptide Y: identification of the binding site. Int J Pept Protein Res. Dec. 1990;36(6):522-30.

Beck-Sickinger et al., Semiautomated T-bag peptide synthesis using 9-fluorenyl-methoxycarbonyl strategy and benzotriazol-1-yl-tetramethyl-uronium tetrafluoroborate activation. Pept Res. Mar.-Apr. 1991;4(2):88-94.

Beck-Sickinger et al., Structure/activity relationships of C-terminal neuropeptide Y peptide segments and analogues composed of sequence 1-4 linked to 25-36. Eur J Biochem. Dec. 12, 1990;194(2):449-56.

Ben-Bassat et al., Processing of the initiation methionine from proteins: properties of the Escherichia coli methionine aminopeptidase and its gene structure. J Bacteriol. Feb. 1987;169(2):751-7.

Bennett et al., Global impairment of the ubiquitin-proteasome system by nuclear or cytoplasmic protein aggregates precedes inclusion body formation. Mol Cell. Feb. 4, 2005;17(3):351-65.

Berenbaum et al., What is synergy? Pharmacol Rev. Jun. 1989;41(2):93-141.

Berg et al., Long-Chain Polystyrene-Grafted Polyethylene Film Matrix: A New Support for Solid-Phase Peptide Synthesis. J Am Chem Soc. 1989;111:8024-26.

Berge et al., Pharmaceutical salts. J Pharm Sci. Jan. 1977;66(1):1-19.

Bernstein et al., Genomewide studies of histone deacetylase function in yeast. Proc Natl Acad Sci U S A. Dec. 5, 2000;97(25):13708-13.

Blackwell et al., A one-bead, one-stock solution approach to chemical genetics: part 1. Chem Biol. Dec. 2001;8(12):1167-82.

Blankemeyer-Menge et al., Simultaneous Multiple Synthesis of Protected Peptide Fragments on "Allyl"—Functionalized Cellulose Disc Supports. Tetrahedron Lett. 1988;29:5871-74.

Blondelle et al., Soluble combinatorial libraries of organic, peptidomimetic and peptide diversities. Trends Anal Chem. 1995;14:83-92.

Bolden et al., Anticancer activities of histone deacetylase inhibitorsNat Rev Drug Discov. Sep. 2006;5(9):769-84.

Bolger et al., Intracellular trafficking of histone deacetylase 4 regulates neuronal cell death. J Neurosci. Oct. 12, 2005;25(41):9544-53.

Borchardt et al., Synthetic Receptor Binding Elucidated with an Encoded Combinatorial Library. J Am Chem Soc. 1994;116:373-74.

Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.

Bowdish et al., Analysis of RIM11, a yeast protein kinase that phosphorylates the meiotic activator IME1. Mol Cell Biol. Dec. 1994;14(12):7909-19.

Bowdish et al., Bipartite structure of an early meiotic upstream activation sequence from Saccharomyces cerevisiae. Mol Cell Biol. Apr. 1993;13(4):2172-81.

Bowers et al., Synthesis and Conformation-Activity Relationships of the Peptide Isosteres of FK228 and Largazole. J Am Chem Soc. 2009;131:2900-05.

Bowers et al., Total synthesis and biological mode of action of largazole: a potent class I histone deacetylase inhibitor. J Am Chem Soc. Aug. 20, 2008;130(33):11219-22. Epub Jul. 19, 2008.

Brachman et al., The SIR2 gene family, conserved from bacteria to humans, functions in silencing, cell cycle progression, and chromosome stability. Genes Dev. Dec. 1, 1995;9(23):2888-902.

Bradley et al., Formation of germ-line chimaeras from embryo-derived teratocarcinoma cell lines. Nature. May 17-23, 1984;309(5965):255-6.

Bradner et al., Chemical phylogenetics of histone deacetylases. Nat Chem Biol. Mar. 2010;6(3):238-243. Epub Feb. 7, 2010.

Branden et al., Chapter 16. Prediction, Engineering, and Design of Protein Structures. In: Introduction to Protein Structure. Garland Publishing Inc., New York. 1991:247.

Braunstein et al., Efficient transcriptional silencing in Saccharomyces cerevisiae requires a heterochromatin histone acetylation pattern. Mol Cell Biol. Aug. 1996;16(8):4349-56.

Braunstein et al., Transcriptional silencing in yeast is associated with reduced nucleosome acetylation. Genes Dev. Apr. 1993;7(4):592-604.

Bray et al., Gas Phase Cleavage of Peptides from a Solid Support with Ammonia Vapour. Application in Simultaneous Multiple Peptide Synthesis. Tetrahedron Lett. 1991;32:6163-66.

Bray et al., The Simultaneous Multiple Production of Solution Phase Peptides; Assessment of the Geysèn Method of Simultaneous Peptide Synthesis. Tetrahedron Lett. 1990;31:5811-14.

Brenner et al., Encoded combinatorial chemistry. Proc Natl Acad Sci U S A. Jun. 15, 1992;89(12):5381-3.

Brinster et al., Factors affecting the efficiency of introducing foreign DNA into mice by microinjecting eggs. Proc Natl Acad Sci U S A. Jul. 1985;82(13):4438-42.

Brownell et al., Tetrahymena histone acetyltransferase A: a homolog to yeast Gcn5p linking histone acetylation to gene activation. Cell. Mar. 22, 1996;84(6):843-51.

Brummel et al., A mass spectrometric solution to the address problem of combinatorial libraries. Science. Apr. 15, 1994;264(5157):399-402.

Brunet et al., Nuclear translocation of p42/p44 mitogen-activated protein kinase is required for growth factor-induced gene expression and cell cycle entry. EMBO J. Feb. 1, 1999;18(3):664-74.

Buiting et al., Detection of aberrant DNA methylation in unique Prader-Willi syndrome patients and its diagnostic implications. Hum Mol Genet. Jun. 1994;3(6):893-5.

Burbaum et al., A paradigm for drug discovery employing encoded combinatorial libraries. Proc Natl Acad Sci U S A. Jun. 20, 1995;92(13):6027-31.

Burbelo, 14-3-3 proteins. Hot numbers in signal transduction. Curr Biol. Feb. 1, 1995;5(2):95-6.

Byrd et al., Depsipeptide (FR901228): a novel therapeutic agent with selective, in vitro activity against human B-cell chronic lymphocytic leukemia cells. Blood. Aug. 15, 1999;94(4):1401-8.

Calí et al., Nucleotide sequence of a cDNA encoding the human muscle-specific enolase (MSE). Nucleic Acids Res. Apr. 11, 1990;18(7):1893.

Cameron, Recent advances in transgenic technology. Mol Biotechnol. Jun. 1997;7(3):253-65.

Carmen et al., HDA1 and HDA3 are components of a yeast histone deacetylase (HDA) complex. J Biol Chem. Jun. 28, 1996;271(26):15837-44.

Catley et al., NVP-LAQ824 is a potent novel histone deacetylase inhibitor with significant activity against multiple myeloma. Blood. Oct. 1, 2003;102(7):2615-22. Epub Jun. 19, 2003.

Cavenee et al., Expression of recessive alleles by chromosomal mechanisms in retinoblastoma. Nature. Oct. 27-Nov. 2, 1983;305(5937):779-84.

Chauhan et al., Blockade of Hsp27 overcomes Bortezomib/proteasome inhibitor PS-341 resistance in lymphoma cells. Cancer Res. Oct. 1, 2003;63(19):6174-7.

Chauhan et al., Hsp27 inhibits release of mitochondrial protein Smac in multiple myeloma cells and confers dexamethasone resistance. Blood. Nov. 1, 2003;102(9):3379-86. Epub Jul. 10, 2003.

Chen et al., "Analogous" Organic Synthesis of Small-Compound Libraries: Validation of Combinatorial Chemistry in Small-Molecule Synthesis. JACS. 1994;116:2661-62.

Chen et al., Gene therapy for brain tumors: regression of experimental gliomas by adenovirus-mediated gene transfer in vivo. Proc Natl Acad Sci U S A. Apr. 12, 1994;91(8):3054-7.

Chu et al., Free Solution Identification of Candidate Peptides from Combinatorial Libraries by Affinity Capillary Electrophoresis/Mass Spectrometry. J Am Chem Soc. 1995;117:5419-20.

Clackson et al., Making antibody fragments using phage display libraries. Nature. Aug. 15, 1991;352(6336):624-8.

Clemons et al., A one-bead, one-stock solution approach to chemical genetics: part 2. Chem Biol. Dec. 2001;8(12):1183-95.

Clipstone et al., Identification of calcineurin as a key signalling enzyme in T-lymphocyte activation. Nature. Jun. 25, 1992;357(6380):695-7.

Cockell et al., Nuclear compartments and gene regulation. Curr Opin Genet Dev. Apr. 1999;9(2):199-205.

Cohen et al., The histone deacetylase HDAC4 connects neural activity to muscle transcriptional reprogramming. J Biol Chem. Nov. 16, 2007;282(46):33752-9. Epub Sep. 16, 2007.

Corcoran et al., A novel action of histone deacetylase inhibitors in a protein aggresome disease model. Curr Biol. Mar. 23, 2004;14(6):488-92.

Cress et al., Histone deacetylases, transcriptional control, and cancer. J Cell Physiol. Jul. 2000;184(1):1-16.

Csordas, On the biological role of histone acetylation. Biochem J. Jan. 1, 1990;265(1):23-38.

Cuperus et al., Locus specificity determinants in the multifunctional yeast silencing protein Sir2. EMBO J. Jun. 1, 2000;19(11):2641-51.

Curtin et al., Succinimide hydroxamic acids as potent inhibitors of histone deacetylase (HDAC). Bioorg Med Chem Lett. Oct. 21, 2002;12(20):2919-23.

Cwirla et al., Peptides on phage: a vast library of peptides for identifying ligands. Proc Natl Acad Sci U S A. Aug. 1990;87(16):6378-82.

Dangond et al., Differential display cloning of a novel human histone deacetylase (HDAC3) cDNA from PHA-activated immune cells. Biochem Biophys Res Commun. Jan. 26, 1998;242(3):648-52.

Dann et al., Human renin: a new class of inhibitors. Biochem Biophys Res Commun. Jan. 14, 1986;134(1):71-7.

David et al., Histone deacetylase associated with mSin3A mediates repression by the acute promyelocytic leukemia-associated PLZF protein. Oncogene. May 14, 1998;16(19):2549-56.

Davie et al., Multiple functions of dynamic histone acetylation. J Cell Biochem. May 1994;55(1):98-105.

De Ruijter et al., Histone deacetylases (HDACs): characterization of the classical HDAC family. Biochem J. Mar. 15, 2003;370(Pt 3):737-49.

Delgrave et al., Recursive ensemble mutagenesis. Protein Engineer. 1993;6(3):327-31.

Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.

Dev et al., Electrochemotherapy—a novel method of cancer treatment. Cancer Treat Rev. Jan. 1994;20(1):105-15.

Devlin et al., Random peptide libraries: a source of specific protein binding molecules. Science. Jul. 27, 1990;249(4967):404-6.

Dower et al., Chapter 28. The Search for Molecular Diversity (II): Recombinant and Synthetic Randomized Peptide Libraries. Annu Rep Med Chem. 1991;26:271-80.

Dul et al., Hsp70 and antifibrillogenic peptides promote degradation and inhibit intracellular aggregation of amyloidogenic light chains. J Cell Biol. Feb. 19, 2001;152(4):705-15.

Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.

Eichler et al., Application of Cellulose Paper as Support Material in Simultaneous Solid Phase Peptide Synthesis. Collect Czech Chem Commun. 1989;54:1746-52.

Eichler et al., Evaluation of cotton as a carrier for solid-phase peptide synthesis. Pept Res. Sep.-Oct. 1991;4(5):296-307.

Ellison et al., Epitope-tagged ubiquitin. A new probe for analyzing ubiquitin function. J Biol Chem. Nov. 5, 1991;266(31):21150-7.

Emiliani et al., Characterization of a human RPD3 ortholog, HDAC3. Proc Natl Acad Sci U S A. Mar. 17, 1998;95(6):2795-800.

Evans et al., An engineered poliovirus chimaera elicits broadly reactive HIV-1 neutralizing antibodies. Nature. Jun. 1, 1989;339(6223):385-8.

Evans et al., Establishment in culture of pluripotential cells from mouse embryos. Nature. Jul. 9, 1981;292(5819):154-6.

Ewenson et al., Ketomethylene pseudopeptide analogues of substance P: synthesis and biological activity. J Med Chem. Feb. 1986;29(2):295-9.

Fabian et al., A small molecule-kinase interaction map for clinical kinase inhibitors. Nat Biotechnol. Mar. 2005;23(3):329-36. Epub Feb. 13, 2005.

Fabunmi et al., Activity and regulation of the centrosome-associated proteasome. J Biol Chem. Jan. 7, 2000;275(1):409-13.

Feling et al., Salinosporamide A: a highly cytotoxic proteasome inhibitor from a novel microbial source, a marine bacterium of the new genus salinospora. Angew Chem Int Ed Engl. Jan. 20, 2003;42(3):355-7.

Felsenfeld, Chromatin as an essential part of the transcriptional mechanism. Nature. Jan. 16, 1992;355(6357):219-24.

Feng et al., Progressive sequence alignment as a prerequisite to correct phylogenetic trees. J Mol Evol. 1987;25(4):351-60.

Finnin et al., Structures of a histone deacetylase homologue bound to the TSA and SAHA inhibitors. Nature. Sep. 9, 1999;401(6749):188-93.

Fischle et al., A new family of human histone deacetylases related to *Saccharomyces cerevisiae* HDA1p. J Biol Chem. Apr. 23, 1999;274(17):11713-20.

Fitch, Distinguishing Homologous from Analogous Proteins. Syst Zool. 1970;19:99-113.

Fitch et al., High-Resolution $^1$H NMR in Solid-Phase Organic Synthesis. J Org Chem. 1994;59:7955-56.

Fleming et al., The total synthesis of ( )-trichostatin A: Some observations on the acylation and alkylation of silyl enol ethers, silyl dienol ethers and a silyl trienol ether. Tetrahedron. 1983;39:841-46.

Fodor et al., Light-directed, spatially addressable parallel chemical synthesis. Science. Feb. 15, 1991;251(4995):767-73.

Frank et al., Simultaneous Multiple Peptide Synthesis Under Continuous Flow Conditions on Cellulose Paper Discs as Segmental Solid Supports. Tetrahedron. 1988;44:6031-40.

Frank et al., Spot-Synthesis: An Easy Technique for the Positionally Addressable, Parallel Chemical Synthesis on a Membrane Support. Tetrahedron. 1992;48:9217-32.

Frank et al., Strategies and Techniques in Simultaneous Solid Phase Synthesis Based on the Segmentation of Membrane Type Supports. Bioorg Med Chem Lett. 1993;3:425-30.

Friend et al., Deletions of a DNA sequence in retinoblastomas and mesenchymal tumors: organization of the sequence and its encoded protein. Proc Natl Acad Sci U S A. Dec. 1987;84(24):9059-63.

Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun. 1999;260:273-79.

Frye, Phylogenetic classification of prokaryotic and eukaryotic Sir2-like proteins. Biochem Biophys Res Commun. Jul. 5, 2000;273(2):793-8.

Furukawa et al., Isolation and mapping of a human gene (RPD3L1) that is homologous to RPD3, a transcription factor in *Saccharomyces cerevisiae*. Cytogenet Cell Genet. 1996;73(1-2):130-3.

Furumai et al., Potent histone deacetylase inhibitors built from trichostatin A and cyclic tetrapeptide antibiotics including trapoxin. Proc Natl Acad Sci U S A. Jan. 2, 2001;98(1):87-92.

Gallop et al., Applications of combinatorial technologies to drug discovery. 1. Background and peptide combinatorial libraries. J Med Chem. Apr. 29, 1994;37(9):1233-51.

Gammon et al., T cell determinant structure: cores and determinant envelopes in three mouse major histocompatibility complex haplotypes. J Exp Med. Mar. 1, 1991;173(3):609-17.

García-Mata et al., Characterization and dynamics of aggresome formation by a cytosolic GFP-chimera. J Cell Biol. Sep. 20, 1999;146(6):1239-54.

Garcia-Mata et al., Hassles with taking out the garbage: aggravating aggresomes. Traffic. Jun. 2002;3(6):388-96.

Garcia-Ramirez et al., Role of the histone "tails" in the folding of oligonucleosomes depleted of histone H1. J Biol Chem. Sep. 25, 1992;267(27):19587-95.

Gardlik et al., Vectors and delivery systems in gene therapy. Med Sci Monit. Apr. 2005;11(4):RA110-21. Epub Mar. 24, 2005.

Gartenberg, The Sir proteins of *Saccharomyces cerevisiae*: mediators of transcriptional silencing and much more. Curr Opin Microbiol. Apr. 2000;3(2):132-7.

Gelmetti et al., Aberrant recruitment of the nuclear receptor corepressor-histone deacetylase complex by the acute myeloid leukemia fusion partner ETO. Mol Cell Biol. Dec. 1998;18(12):7185-91.

Geysen et al., Use of peptide synthesis to probe viral antigens for epitopes to a resolution of a single amino acid. Proc Natl Acad Sci U S A. Jul. 1984;81(13):3998-4002.

Gordon et al., Applications of combinatorial technologies to drug discovery. 2. Combinatorial organic synthesis, library screening strategies, and future directions. J Med Chem. May 13, 1994;37(10):1385-401.

Gordon et al., Design of peptide derived amino alcohols as transition-state analog inhibitors of angiotensin converting enzyme. Biochem Biophys Res Commun. Jan. 16, 1985;126(1):419-26.

Görlich, Nuclear protein import. Curr Opin Cell Biol. Jun. 1997;9(3):412-9.

Gossler et al., Transgenesis by means of blastocyst-derived embryonic stem cell lines. Proc Natl Acad Sci U S A. Dec. 1986;83(23):9065-9.

Goy et al., Phase II study of proteasome inhibitor bortezomib in relapsed or refractory B-cell non-Hodgkin's lymphoma. J Clin Oncol. Feb. 1, 2005;23(4):667-75. Epub Dec. 21, 2004.

Gray et al., The human histone deacetylase family. Exp Cell Res. Jan. 15, 2001;262(2):75-83.

Green, When the products of oncogenes and anti-oncogenes meet. Cell. Jan. 13, 1989;56(1):1-3.

Gregoretti et al., Molecular evolution of the histone deacetylase family: functional implications of phylogenetic analysisJ Mol Biol. Apr. 16, 2004;338(1):17-31.

Gregory et al., Combination chemotherapy versus melphalan and prednisolone in the treatment of multiple myeloma: an overview of published trials. J Clin Oncol. Feb. 1992;10(2):334-42.

Griffiths et al., Human anti-self antibodies with high specificity from phage display libraries. EMBO J. Feb. 1993;12(2):725-34.

Grignani et al., Fusion proteins of the retinoic acid receptor-alpha recruit histone deacetylase in promyelocytic leukaemia. Nature. Feb. 19, 1998;391(6669):815-8.

Grozinger et al., Deacetylase enzymes: biological functions and the use of small-molecule inhibitors. Chem Biol. Jan. 2002;9(1):3-16.

Grozinger et al., Regulation of histone deacetylase 4 and 5 and transcriptional activity by 14-3-3-dependent cellular localization. Proc Natl Acad Sci U S A. Jul. 5, 2000;97(14):7835-40.

Grozinger et al., Three proteins define a class of human histone deacetylases related to yeast Had1p. Proc Natl Acad Sci U S A. Apr. 27, 1999;96(9):4868-73.

Grunstein, Histone acetylation in chromatin structure and transcription. Nature. Sep. 25, 1997;389(6649):349-52.

Grunstein, Molecular model for telomeric heterochromatin in yeast. Curr Opin Cell Biol. Jun. 1997;9(3):383-7.

Gu et al., Activation of p53 sequence-specific DNA binding by acetylation of the p53 C-terminal domain. Cell. Aug. 22, 1997;90(4):595-606.

Guo et al., Protein tolerance to random amino acid change. Proc Natl Acad Sci U S A. Jun. 22, 2004;101(25):9205-10. Epub Jun. 14, 2004.

Guarente, Sir2 links chromatin silencing, metabolism, and aging. Genes Dev. May 1, 2000;14(9):1021-6.

Habig et al., Glutathione S-transferases. The first enzymatic step in mercapturic acid formation. J Biol Chem. Nov. 25, 1974;249(22):7130-9.

Haggarty et al., Dissecting cellular processes using small molecules: identification of colchicine-like, taxol-like and other small molecules that perturb mitosis. Chem Biol. Apr. 2000;7(4):275-86.

Haggarty et al., Domain-selective small-molecule inhibitor of histone deacetylase 6 (HDAC6)-mediated tubulin deacetylation. Proc Natl Acad Sci U S A. Apr. 15, 2003;100(8):4389-94. Epub Apr. 3, 2003.

Haggarty et al., Mapping chemical space using molecular descriptors and chemical genetics: deacetylase inhibitors. Comb Chem High Throughput Screen. Nov. 2004;7(7):669-76.

Haggarty et al., Multidimensional chemical genetic analysis of diversity-oriented synthesis-derived deacetylase inhibitors using cell-based assays. Chem Biol. May 2003;10(5):383-96.

Hansen et al., Retinoblastoma and the progression of tumor genetics. Trends Genet. May 1988;4(5):125-8.

Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.

Hassig et al., A role for histone deacetylase activity in HDAC1-mediated transcriptional repression. Proc Natl Acad Sci U S A. Mar. 31, 1998;95(7):3519-24.

Hassig et al., Histone deacetylase activity is required for full transcriptional repression by mSin3A. Cell. May 2, 1997;89(3):341-7.

Hassig et al., Nuclear histone acetylases and deacetylases and transcriptional regulation: HATs off to HDACs. Curr Opin Chem Biol. Oct. 1997;1(3):300-8.

Hathaway et al., Dissecting cell biology with chemical scalpels. Curr Opin Cell Biol. Feb. 2005;17(1):12-9.

Hay et al., Histone deacetylase. Association with a nuclease resistant, high molecular weight fraction of HeLa cell chromatin. J Biol Chem. Mar. 25, 1983;258(6):3726-34.

Hayes et al., Histones H2A/H2B inhibit the interaction of transcription factor IIIA with the Xenopus borealis somatic 5S RNA gene in a nucleosome. Proc Natl Acad Sci U S A. Feb. 15, 1992;89(4):1229-33.

He et al., Distinct interactions of PML-RARalpha and PLZF-RARalpha with co-repressors determine differential responses to RA in APL. Nat Genet. Feb. 1998;18(2):126-35.

Hecht et al., Histone H3 and H4 N-termini interact with SIR3 and SIR4 proteins: a molecular model for the formation of heterochromatin in yeast. Cell. Feb. 24, 1995;80(4):583-92.

Hicks et al., Protein import into the nucleus: an integrated view. Annu Rev Cell Dev Biol. 1995;11:155-88.

Hideshima et al., Antitumor activity of lysophosphatidic acid acyltransferase-beta inhibitors, a novel class of agents, in multiple myeloma. Cancer Res. Dec. 1, 2003;63(23):8428-36.

Hideshima et al., Molecular mechanisms mediating antimyeloma activity of proteasome inhibitor PS-341. Blood. Feb. 15, 2003;101(4):1530-4. Epub Sep. 26, 2002.

Hideshima et al., Molecular mechanisms of novel therapeutic approaches for multiple myeloma. Nat Rev Cancer. Dec. 2002;2(12):927-37.

Hideshima et al., NF-κB as a therapeutic target in multiple myeloma. J Biol Chem. May 10, 2002;277(19):16639-47. Epub Feb. 28, 2002.

Hideshima et al., Novel therapeutic approaches for multiple myeloma. Immunol Rev. Aug. 2003;194:164-76.

Hideshima et al., p38 MAPK inhibition enhances PS-341 (bortezomib)-induced cytotoxicity against multiple myeloma cells. Oncogene. Nov. 18, 2004;23(54):8766-76.

Hideshima et al., Proteasome inhibitor PS-341 abrogates IL-6 triggered signaling cascades via caspase-dependent downregulation of gp130 in multiple myeloma. Oncogene. Nov. 20, 2003;22(52):8386-93.

Hideshima et al., Small-molecule inhibition of proteasome and aggresome function induces synergistic antitumor activity in multiple myeloma. Proc Natl Acad Sci U S A. Jun. 14, 2005;102(24):8567-72. Epub Jun. 3, 2005.

Hideshima et al., The proteasome inhibitor PS-341 inhibits growth, induces apoptosis, and overcomes drug resistance in human multiple myeloma cells. Cancer Res. Apr. 1, 2001;61(7):3071-6.

Hideshima et al., The role of tumor necrosis factor alpha in the pathophysiology of human multiple myeloma: therapeutic applications. Oncogene. Jul. 27, 2001;20(33):4519-27.

Hochuli et al., New metal chelate adsorbent selective for proteins and peptides containing neighbouring histidine residues. J Chromatogr. Dec. 18, 1987;411:177-84.

Houdebine, The methods to generate transgenic animals and to control transgene expression. J Biotechnol. Sep. 25, 2002;98(2-3):145-60.

Houghten, General method for the rapid solid-phase synthesis of large numbers of peptides: specificity of antigen-antibody interaction at the level of individual amino acids. Proc Natl Acad Sci U S A. Aug. 1985;82(15):5131-5.

Houghten et al., Simplified procedure for carrying out simultaneous multiple hydrogen fluoride cleavages of protected peptide resins. Int J Pept Protein Res. Jun. 1986;27(6):673-8.

Hu et al., Cloning and characterization of a novel human class I histone deacetylase that functions as a transcription repressor. J Biol Chem. May 19, 2000;275(20):15254-64.

Huang et al., Nuclear receptor corepressors partner with class II histone deacetylases in a Sin3-independent repression pathway. Genes Dev. Jan. 1, 2000;14(1):45-54.

Huang et al., Vaccinia virus recombinants expressing an 11-kilodalton beta-galactosidase fusion protein incorporate active beta-galactosidase in virus particles. J Virol. Oct. 1988;62(10):3855-61.

Hubbert et al., HDAC6 is a microtubule-associated deacetylase. Nature. May 23, 2002;417(6887):455-8.

Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.

Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.

Imai et al., Transcriptional silencing and longevity protein Sir2 is an NAD-dependent histone deacetylase. Nature. Feb. 17, 2000;403(6771):795-800.

Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.

Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.

Imhof et al., Acetylation of general transcription factors by histone acetyltransferases. Curr Biol. Sep. 1, 1997;7(9):689-92.

Itakura et al., Expression in *Escherichia coli* of a Chemically Synthesized Gene for the Hormone Somatostatin. Science. 1984;198:1056-63.

Itakura et al., Synthesis and use of synthetic oligonucleotides. Annu Rev Biochem. 1984;53:323-56.

Iwabuchi et al., Use of the two-hybrid system to identify the domain of p53 involved in oligomerization. Oncogene. Jun. 1993;8(6):1693-6.

Jacobs et al., Combinatorial chemistry—applications of light-directed chemical synthesis. Trends Biotechnol. Jan. 1994;12(1):19-26.

Jaenisch, Germ line integration and Mendelian transmission of the exogenous Moloney leukemia virus. Proc Natl Acad Sci U S A. Apr. 1976;73(4):1260-4.

Jaenisch, Transgenic animals. Science. Jun. 10, 1988;240(4858):1468-74.

Jähner et al., De novo methylation and expression of retroviral genomes during mouse embryogenesis. Nature. Aug. 12, 1982;298(5875):623-8.

Jähner et al., Insertion of the bacterial gpt gene into the germ line of mice by retroviral infection. Proc Natl Acad Sci U S A. Oct. 1985;82(20):6927-31.

Janknecht et al., Rapid and efficient purification of native histidine-tagged protein expressed by recombinant vaccinia virus. Proc Natl Acad Sci U S A. Oct. 15, 1991;88(20):8972-6.

Jin et al., Transcriptional regulation of the MDR1 gene by histone acetyltransferase and deacetylase is mediated by NF-Y. Mol Cell Biol. Jul. 1998;18(7):4377-84.

Johnson et al., Deacetylase activity associates with topoisomerase II and is necessary for etoposide-induced apoptosis. J Biol Chem. Feb. 16, 2001;276(7):4539-42. Epub Jan. 2, 2001.

Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.

Johnson et al., Molecular cloning of Drosophila melanogaster cDNAs that encode a novel histone deacetylase dHDAC3. Gene. Oct. 9, 1998;221(1):127-34.

Johnston et al., Aggresomes: a cellular response to misfolded proteins. J Cell Biol. Dec. 28, 1998;143(7):1883-98.

Johnstone, Histone-deacetylase inhibitors: novel drugs for the treatment of cancer. Nat Rev Drug Discov. Apr. 2002;1(4):287-99.

Jones et al., Probing the elusive catalytic activity of vertebrate class IIa histone deacetylases. Bioorg Med Chem Lett. Mar. 15, 2008;18(6):1814-9. Epub Feb. 14, 2008.

Jung et al., Amide analogues of trichostatin A as inhibitors of histone deacetylase and inducers of terminal cell differentiation. J Med Chem. Nov. 4, 1999;42(22):4669-79.

Junn et al., Parkin accumulation in aggresomes due to proteasome impairment. J Biol Chem. Dec. 6, 2002;277(49):47870-7. Epub Oct. 2, 2002.

Kao et al., Isolation of a novel histone deacetylase reveals that class I and class II deacetylases promote SMRT-mediated repression. Genes Dev. Jan. 1, 2000;14(1):55-66.

Kappel et al., Regulating gene expression in transgenic animals. Curr Opin Biotechnol. Oct. 1992;3(5):548-53.

Katoh et al., MAFFT: a novel method for rapid multiple sequence alignment based on fast Fourier transformation. Nucleic Acids Res. Jul. 15, 2002;30(14):3059-66.

Kawaguchi et al., The deacetylase HDAC6 regulates aggresome formation and cell viability in response to misfolded protein stress. Cell. Dec. 12, 2003;115(6):727-38.

Kennedy et al., Redistribution of silencing proteins from telomeres to the nucleolus is associated with extension of life span in S. cerevisiae. Cell. May 2, 1997;89(3):381-91.

Kerr et al., Encoded Combinatorial Peptide Libraries Containing Non-Natural Amino Acids. J Am Chem, Soc. 1993;115:2529-31.

Khockbin et al., Functional significance of histone deacetylase diversity. Curr Opin Genet Dev. Apr. 2001;11(2):162-6.

Kijima et al., Trapoxin, an antitumor cyclic tetrapeptide, is an irreversible inhibitor of mammalian histone deacetylase. J Biol Chem. Oct. 25, 1993;268(30):22429-35.

Kikuchi et al., Multiplicity of histone deacetylase from calf thymus. FEBS Lett. Feb. 1, 1973;29(3):280-282.

Kleff et al., Identification of a gene encoding a yeast histone H4 acetyltransferase. J Biol Chem. Oct. 20, 1995;270(42):24674-7.

Koeller et al., Chemical genetic modifier screens: small molecule trichostatin suppressors as probes of intracellular histone and tubulin acetylation. Chem Biol. May 2003;10(5):397-410.

Kohler et al., Continuous cultures of fused cells secreting antibody of predefined specificity. Nature. Aug. 7, 1975;256(5517):495-7.

Kopito et al., Aggresomes and Russell bodies. Symptoms of cellular indigestion? EMBO Rep. Sep. 2000;1(3):225-31.

Kopito, Aggresomes, inclusion bodies and protein aggregation. Trends Cell Biol. Dec. 2000;10(12):524-30.

Kouzarides, Acetylation: a regulatory modification to rival phosphorylation? EMBO J. Mar. 15, 2000;19(6):1176-9.

Kozbar et al., The production of monoclonal antibodies from human lymphocytes. Immunology Today. 1983;4:72-79.

Krieger et al., Chemical studies of histone acetylation. Substrate specificity of a histone deacetylase from calf thymus nuclei. J Biol Chem. Jan. 10, 1974;249(1):332-4.

Kumar et al., MEGA: a biologist-centric software for evolutionary analysis of DNA and protein sequences. Brief Bioinform. Jul. 2008;9(4):299-306. Epub Apr. 16, 2008.

Kuruvilla et al., Dissecting glucose signaling with diversity-oriented synthesis and small-molecule microarrays. Nature. Apr. 11, 2002;416(6881):653-7.

Kwon et al., Depudecin induces morphological reversion of transformed fibroblasts via the inhibition of histone deacetylase. Proc Natl Acad Sci U S A. Mar. 31, 1998;95(7):3356-61.

Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.

Lam et al., The "One-Bead-One-Compound" Combinatorial Library Method. Chem Rev. Apr. 1, 1997;97(2):411-48.

Landegren et al., A ligase-mediated gene detection technique. Science. Aug. 26, 1988;241(4869):1077-80.

Landry et al., The silencing protein SIR2 and its homologs are NAD-dependent protein deacetylases. Proc Natl Acad Sci U S A. May 23, 2000;97(11):5807-11.

Lasko et al., Targeted oncogene activation by site-specific recombination in transgenic mice. Proc Natl Acad Sci U S A. Jul. 15, 1992;89(14):6232-6.

Lee et al., A positive role for histone acetylation in transcription factor access to nucleosomal DNA. Cell. Jan. 15, 1993;72(1):73-84.

Lee et al., A Strategy for Macrocyclic Ring Closure and Functionalization Aimed toward Split-Pool Syntheses. J Am Chem Soc. 1999;121(45):10648-49.

Lee et al., Histone acetyltransferase complexes: one size doesn't fit all. Nat Rev Mol Cell Biol. Apr. 2007;8(4):284-95.

Lee et al., Proteasome inhibitors disrupt the unfolded protein response in myeloma cells. Proc Natl Acad Sci U S A. Aug. 19, 2003;100(17):9946-51. Epub Aug. 5, 2003.

Lin et al., Generation and Aldol Reaction of Endlate Anion Adjacnet to a $\eta$3-Allyl-Mo(Co)$^2$Cp Moiety. A New Approach to the Stereoselctive Synthesis of 1,3,5-Triol and 2-Vinyl-3-Hydroxyl-Tetrahydrofuran. Tetrahedron Letters.1990;31(52):7645-48.

Lin et al., Role of the histone deacetylase complex in acute promyelocytic leukaemia. Nature. Feb. 19, 1998;391(6669):811-4.

Lizcano et al., Cell type-specific roles of histone deacetylase in TR ligand-independent transcriptional repression. Mol Cell Endocrinol. Feb. 14, 2001;172(1-2):13-20.

Look et al., Methods for Combinatorial Organic Synthesis: The Use of Fast $^{13}$C NMR Analysis for Gel Phase Reaction Monitoring. J Org Chem. 1994;59:7588-90.

Lopez-Girona et al., Nuclear localization of Cdc25 is regulated by DNA damage and a 14-3-3 protein. Nature. Jan. 14, 1999;397(6715):172-5.

Luger et al., Crystal structure of the nucleosome core particle at 2.8 A resolution. Nature. Sep. 18, 1997;389(6648):251-60.

Lutterbach et al., ETO, a target of t(8;21) in acute leukemia, interacts with the N-CoR and mSin3 corepressors. Mol Cell Biol. Dec. 1998;18(12):7176-84.

MacBeath et al., Printing proteins as microarrays for high-throughput function determination. Science. Sep. 8, 2000;289(5485):1760-3.

Macherla et al., Structure-activity relationship studies of salinosporamide A (NPI-0052), a novel marine derived proteasome inhibitor. J Med Chem. Jun. 2, 2005;48(11):3684-7.

Maddry et al., Inhibition of the Her2 Tyrosine Kinase and Characterization of a Hydrophobic Site Near the Nucleotide Binding Domain. Bioorganic Med Chem Letter. 1997;7(16):2109-14.

Madura et al., N-recognin/Ubc2 interactions in the N-end rule pathway. J Biol Chem. Jun. 5, 1993;268(16):12046-54.

Maeji et al., Multi-pin peptide synthesis strategy for T cell determinant analysis. J Immunol Methods. Nov. 6, 1990;134(1):23-33.

Magnaghi-Jaulin et al., Retinoblastoma protein represses transcription by recruiting a histone deacetylase. Nature. Feb. 5, 1998;391(6667):601-4.

Mahboobi et al., Design of chimeric histone deacetylase- and tyrosine kinase-inhibitors: a series of imatinib hybrides as potent inhibitors of wild-type and mutant BCR-ABL, PDGF-Rbeta, and histone deacetylases. J Med Chem. Apr. 23, 2009;52(8):2265-79.

Manetto et al., Selective presence of ubiquitin in intracellular inclusions. Am J Pathol. Mar. 1989;134(3):505-13.

Marcand et al., Silencing of genes at nontelomeric sites in yeast is controlled by sequestration of silencing factors at telomeres by Rap 1 protein. Genes Dev. Jun. 1, 1996;10(11):1297-309.

Marks et al., Histone deacetylases and cancer: causes and therapies. Nat Rev Cancer. Dec. 2001;1(3):194-202.

Marks et al., Histone deacetylases. Curr Opin Pharmacol. Aug. 2003;3(4):344-51.

Marks et al., Molecular evolution of proteins on filamentous phage. Mimicking the strategy of the immune system. J Biol Chem. Aug. 15, 1992;267(23):16007-10.

Marmuse et al., "Click chemistry" en route to pseudo-starch. Org Biomol Chem. Jun. 21, 2005;3(12):2225-7. Epub May 11, 2005.

Martinelli et al., Molecular therapy for multiple myeloma. Haematologica. Sep. 2001;86(9):908-17.

Marushige et al., Template properties of liver chromatin. J Mol Biol. Jan. 1966;15(1):160-74.

Marx et al., Bench to bedside: the development of rapamycin and its application to stent restenosis. Circulation. Aug. 21, 2001;104(8):852-5.

Massa et al., Synthesis and antimicrobial and cytotoxic activities of pyrrole-containing analogues of trichostatin A. J Med Chem. Oct. 1990;33(10):2845-9.

McKenzie et al., The centromere and promoter factor, 1, CPF1, of Saccharomyces cerevisiae modulates gene activity through a family of factors including SPT21, RPD1 (SIN3), RPD3 and CCR4. Mol Gen Genet. Sep. 1993;240(3):374-86.

Megee et al., Genetic analysis of histone H4: essential role of lysines subject to reversible acetylation. Science. Feb. 16, 1990;247(4944):841-5.

Meinke et al., Histone deacetylase: a target for antiproliferative and antiprotozoal agents. Curr Med Chem. Feb. 2001;8(2):211-35.

Meinke et al., Synthesis of apicidin-derived quinolone derivatives: parasite-selective histone deacetylase inhibitors and antiproliferative agents. J Med Chem. Dec. 14, 2000;43(25):4919-22.

Merrifield et al., Solid Phase Peptide Syntheses. I. The Synthesis of a Tetrapeptide. J Am Chem Soc. 1963;85:2149-54.

Metzger et al., Ion-Spray Mass Spectrometry and High-Performance Liquid Chromatography-Mass Spectrometry of Synthetic Peptide Libraries. Angew Chem Int Ed Engl. 1993;32:894-96.

Miano et al., HDAC7 supports vascular integrity. Nat Med. Sep. 2006;12(9):997-8.

Miller et al., Histone deacetylase inhibitors. J Med Chem. Nov. 20, 2003;46(24):5097-116.

Miller et al., N-terminal methionine-specific peptidase in Salmonella typhimurium. Proc Natl Acad Sci U S A. May 1987;84(9):2718-22.

Minucci et al., Histone deacetylase inhibitors and the promise of epigenetic (and more) treatments for cancer. Nat Rev Cancer. Jan. 2006;6(1):38-51.

Miska et al., HDAC4 deacetylase associates with and represses the MEF2 transcription factor. EMBO J. Sep. 15, 1999;18(18):5099-107.

Mitchison, Towards a pharmacological genetics. Chem Biol. Sep. 1994;1(1):3-6.

Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30.

Mitsiades et al., Molecular sequelae of histone deacetylase inhibition in human malignant B cells. Blood. May 15, 2003;101(10):4055-62. Epub Jan. 16, 2003.

Mitsiades et al., Molecular sequelae of proteasome inhibition in human multiple myeloma cells. Proc Natl Acad Sci U S A. Oct. 29, 2002;99(22):14374-9. Epub Oct. 21, 2002.

Mitsiades et al., Novel biologically based therapies for Waldenstrom's macroglobulinemia. Semin Oncol. Apr. 2003;30(2):309-12.

Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.

Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.

Moazed, Enzymatic activities of Sir2 and chromatin silencing. Curr Opin Cell Biol. Apr. 2001;13(2):232-8.

Mori et al., Synthesis of trichostatin A, a potent differentiation inducer of friend leukemic cells, and its antipode. Tetrahedron. 1988;44:6013-20.

Mottet et al., Histone deacetylase 7 silencing alters endothelial cell migration, a key step in angiogenesis. Circ Res. Dec. 7, 2007;101(12):1237-46. Epub Oct. 18, 2007.

Mowat et al., Rearrangements of the cellular p53 gene in erythroleukaemic cells transformed by Friend virus. Nature. Apr. 18-24, 1985;314(6012):633-6.

Mullins et al., Transgenesis in nonmurine species. Hypertension. Oct. 1993;22(4):630-3.

Munshi et al., Acetylation of HMG I(Y) by CBP turns off IFN beta expression by disrupting the enhanceosome. Mol Cell. Oct. 1998;2(4):457-67.

Mutch et al., Effects of end groups on the stimulatory capacity of minimal length T cell determinant peptides. Pept Res. May-Jun. 1991;4(3):132-7.

Myers et al., Preparation of the Chiral, C-Protected α-Amino Aldehydes of High Optical Purity and Their Use as Condensation Components in a Linear Synthesis Strategy. J Am Chem Soc. 1999;121:8401-02.

Nagai et al., Synthesis of a Bicyclic Dipeptide with the Shape of β-Turn Central Part. Tetrahedron Lett. 1985;26:647-50.

Nagy et al., Nuclear receptor repression mediated by a complex containing SMRT, mSin3A, and histone deacetylase. Cell. May 2, 1997;89(3):373-80.

Nakatsuka et al., Total Synthesis of FK506 and an FKBP Probe Reagent, ($C_8$, $C_9$-$^{13}C_2$)-FK506. J. Am. Chem. Soc. 1990; 112: 5583-5601.

Nakazawa et al., UV and skin cancer: specific p53 gene mutation in normal skin as a biologically relevant exposure measurement. Proc Natl Acad Sci U S A. Jan. 4, 1994;91(1):360-4.

Narang, DNA Synthesis. Tetrahedron. 1983;39:3-22.

Nardelii et al., A chemically defined synthetic vaccine model for HIV-1. J Immunol. Feb. 1, 1992;148(3):914-20.

Nasmyth et al., Both positive and negative regulators of HO transcription are required for mother-cell-specific mating-type switching in yeast. Cell. Feb. 27, 1987;48(4):579-87.

Needleman et al., A general method applicable to the search for similarities in the amino acid sequence of two proteins. J Mol Biol. Mar. 1970;48(3):443-53.

Needles et al., Generation and screening of an oligonucleotide-encoded synthetic peptide library. Proc Natl Acad Sci. 1993;90:10700-04.

Neer et al., The ancient regulatory-protein family of WD-repeat proteins. Nature. Sep. 22, 1994;371(6495):297-300.

Nefzi et al., The Current Status of Heterocyclic Combinatorial Libraries. Chem Rev. Apr. 1, 1997;97(2):449-472.

Nestler et al., A General Method for Molecular Tagging of Encoded Combinatorial Chemistry Libraries. J Org Chem. 1994;59:4723-24.

Newman et al., The influence of natural products upon drug discovery. Nat Prod Rep. Jun. 2000;17(3):215-34.

Ng et al., Histone deacetylases: silencers for hire. Trends Biochem Sci. Mar. 2000;25(3):121-6.

Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.

Nielsen et al., Crystal structure of a bacterial class 2 histone deacetylase homologue. J Mol Biol. Nov. 18, 2005;354(1):107-20. Epub Oct. 7, 2005.

Nielsen et al., Synthetic Methods for the Implementation of Encoded Combinatorial Chemistry. J Am Chem Soc. 1993;115:9812-13.

Nielsen et al., Toward Chemical Implementation of Encoded Combinatorial Libraries. Methods Compan Methods Enzymol. 1994;6:361-71.

Nikolaiev et al., Peptide-encoding for structure determination of nonsequenceable polymers within libraries synthesized and tested on solid-phase supports. Pept Res. May-Jun. 1993;6(3):161-70.

Noll, Characterization of macromolecules by constant velocity sedimentation. Nature. Jul. 22, 1967;215(5099):360-3.

Notterpek et al., PMP22 accumulation in aggresomes: implications for CMT1A pathology. Neurobiol Dis. Oct. 1999;6(5):450-60.

O'Connor, Developing new drugs for the treatment of lymphoma. European Journal of Haematology. 2005;75:150-58.

O'Gorman et al., Recombinase-mediated gene activation and site-specific integration in mammalian cells. Science. Mar. 15, 1991;251(4999):1351-5.

Ohlmeyer et al., Complex synthetic chemical libraries indexed with molecular tags. Proc Natl Acad Sci U S A. Dec. 1, 1993;90(23):10922-6.

Oliva et al., Histone hyperacetylation can induce unfolding of the nucleosome core particle. Nucleic Acids Res. May 11, 1990;18(9):2739-47.

Orban et al., Tissue- and site-specific DNA recombination in transgenic mice. Proc Natl Acad Sci U S A. Aug. 1, 1992;89(15):6861-5.

Park et al., Point mutations in the yeast histone H4 gene prevent silencing of the silent mating type locus HML. Mol Cell Biol. Sep. 1990;10(9):4932-4.

Parra et al., Protein kinase D1 phosphorylates HDAC7 and induces its nuclear export after T-cell receptor activation J Biol Chem. Apr. 8, 2005;280(14):13762-70. Epub Dec. 28, 2004.

Pátek et al., Safety-catch anchoring linkage for synthesis of peptide amides by Boc/Fmoc strategu. Tetrahedron Lett. 1991;32:3891-94.

Patel et al., Identification and characterization of small molecule inhibitors of a class I histone deacetylase from Plasmodium falciparum. J Med Chem. Apr. 23, 2009;52(8):2185-7.

Pei it al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.

Perrod et al., A cytosolic NAD-dependent deacetylase, Hst2p, can modulate nucleolar and telomeric silencing in yeast. EMBO J. Jan. 15, 2001;20(1-2):197-209.

Peterson et al., Small molecule developmental screens reveal the logic and timing of vertebrate development. Proc Natl Acad Sci U S A. Nov. 21, 2000;97(24):12965-9.

Phillips, The challenge of gene therapy and DNA delivery. J Pharm Pharmacol. Sep. 2001;53(9):1169-74.

Posnett et al., A novel method for producing anti-peptide antibodies. Production of site-specific antibodies to the T cell antigen receptor beta-chain. J Biol Chem. Feb. 5, 1988;263(4):1719-25.

Presbitero et al., Drug-eluting stents do they make the difference? Minerva Cardioangiol. Oct. 2002;50(5):431-42. Italian.

Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.

Pyne et al., Reactions of Lithiated *N*-Tosyl *S*-Phenyl *S*-2-Propenyl Sulfoximine with Aldehydes. Sulfur Letters. 1997;20(6):255-60.

Qian et al., A retinoblastoma-binding protein related to a negative regulator of Ras in yeast. Nature. Aug. 12, 1993;364(6438):648-52.

Raje et al., Combination of the mTOR inhibitor rapamycin and CC-5013 has synergistic activity in multiple myeloma. Blood. Dec. 15, 2004;104(13):4188-93. Epub Aug. 19, 2004.

Remiszewski, The discovery of NVP-LAQ824: from concept to clinic. Curr Med Chem. Nov. 2003;10(22):2393-402.

Renthal et al., Histone deacetylase 5 epigenetically controls behavioral adaptations to chronic emotional stimuli. Neuron. Nov. 8, 2007;56(3):517-29.

Richardson et al., A phase 2 study of bortezomib in relapsed, refractory myeloma. N Engl J Med. Jun. 26, 2003;348(26):2609-17.

Richon et al., A class of hybrid polar inducers of transformed cell differentiation inhibits histone deacetylases. Proc Natl Acad Sci U S A. Mar. 17, 1998;95(6):3003-7.

Richon et al., Histone deacetylase inhibitor selectively induces p21WAF1 expression and gene-associated histone acetylation. Proc Natl Acad Sci U S A. Aug. 29, 2000;97(18):10014-9.

Richon et al., Second generation hybrid polar compounds are potent inducers of transformed cell differentiation. Proc Natl Acad Sci U S A. Jun. 11, 1996;93(12):5705-8.

Riester et al., Members of the histone deacetylase superfamily differ in substrate specificity towards small synthetic substrates. Biochem Biophys Res Commun. Nov. 19, 2004;324(3):1116-23.

Rine et al., Four genes responsible for a position effect on expression from HML and HMR in *Saccharomyces cerevisiae*. Genetics. May 1987;116(1):9-22.
Rittinger et al., Structural analysis of 14-3-3 phosphopeptide complexes identifies a dual role for the nuclear export signal of 14-3-3 in ligand binding. Mol Cell. Aug. 1999;4(2):153-66.
Roberts et al., Directed evolution of a protein: selection of potent neutrophil elastase inhibitors displayed on M13 fusion phage. Proc Natl Acad Sci U S A. Mar. 15, 1992;89(6):2429-33.
Robertson et al., Germ-line transmission of genes introduced into cultured pluripotential cells by retroviral vector. Nature. Oct. 2-8, 1986;323(6087):445-8.
Rosato et al., Histone deacetylase inhibitors in clinical development. Expert Opin Investig Drugs. Jan. 2004;13(1):21-38.
Rudinger, Characteristics of the amino acids as components of a peptide hormone sequence. In: Peptide Hormones. J.A. Parsons, ed. University Park Press, Baltimore, MD. 1976;1-7.
Rundlett et al., HDA 1 and RPD3 are members of distinct yeast histone deacetylase complexes that regulate silencing and transcription. Proc Natl Acad Sci U S A. Dec. 10, 1996;93(25):14503-8.
Ruygrok et al., Rapamycin in cardiovascular medicine. Intern Med J. Mar. 2003;33(3):103-9.
Saitou et al., The neighbor-joining method: a new method for reconstructing phylogenetic trees. Mol Biol Evol. Jul. 1987;4(4):406-25.
Sanchez Del Pino et al., Properties of the yeast nuclear histone deacetylase. Biochem J. Nov. 1, 1994;303 ( Pt 3):723-9.
Sasaki et al., Ligand-induced recruitment of a histone deacetylase in the negative-feedback regulation of the thyrotropin beta gene. EMBO J. Oct. 1, 1999;18(19):5389-98.
Sato et al., Synthesis and Antibiotic Activity of a Gramicidin S Analogue containing Bicyclic β-Turn Dipeptides. J Chem Soc Perkin Trans. 1986;1:1231-34.
Sawa et al., Histone deacetylase inhibitors such as sodium butyrate and trichostatin A induce apoptosis through an increase of the bcl-2-related protein Bad. Brain Tumor Pathol. 2001;18(2):109-14.
Schena, Quantitative Monitoring of Gene Expression Patterns with a Complementary DNA Microarray. Science. 1995;270:467-70.
Schlienger et al., Human immunodeficiency virus type 1 major neutralizing determinant exposed on hepatitis B surface antigen particles is highly immunogenic in primates. J Virol. Apr. 1992;66(4):2570-6.
Schmidt et al., Rapid determination of methadone in plasma, cerebrospinal fluid, and urine by gas chromatography and its application to routine drug monitoring. Pharm Res. Mar. 1993;10(3):441-4.
Schreiber, Chemical genetics resulting from a passion for synthetic organic chemistry. Bioorg Med Chem. Aug. 1998;6(8):1127-52.
Schreiber, Target-oriented and diversity-oriented organic synthesis in drug discovery. Science. Mar. 17, 2000;287(5460):1964-9.
Schreiber, Using the Principles of Organic Chemistry to Explore Cell Biology. Chem and Eng News. 1992; 70(43): 22-32.
Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.
Scott et al., Searching for peptide ligands with an epitope library. Science. Jul. 27, 1990;249(4967):386-90.
Secrist et al., HDAC inhibitors for the treatment of cancer. Curr Opin Investig Drugs. Dec. 2003;4(12):1422-7.
Seffernick et al., Melamine deaminase and atrazine chlorohydrolase: 98 percent identical but functionally different. J Bacteriol. Apr. 2001;183(8):2405-10.
Serrador et al., HDAC6 deacetylase activity links the tubulin cytoskeleton with immune synapse organization. Immunity. Apr. 2004;20(4):417-28.
Shpaer, GeneAssist. Smith-Waterman and other database similarity searches and identification of motifs. Methods Mol Biol. 1997;70:173-87.
Sikorski et al., A system of shuttle vectors and yeast host strains designed for efficient manipulation of DNA in *Saccharomyces cerevisiae*. Genetics. May 1989;122(1):19-27.
Smith et al., A phylogenetically conserved NAD+-dependent protein deacetylase activity in the Sir2 protein family. Proc Natl Acad Sci U S A. Jun. 6, 2000;97(12):6658-63.

Smith et al., Comparison of biosequences. Adv Appl Math. 1981;2:482-89.
Smith et al., Mechanisms and molecular probes of sirtuins. Chem Biol. Oct. 20, 2008;15(10):1002-13.
Somoza et al., Structural snapshots of human HDAC8 provide insights into the class I histone deacetylases. Structure. Jul. 2004;12(7):1325-34.
Stamatakis et al., A rapid bootstrap algorithm for the RAxML Web servers. Syst Biol. Oct. 2008;57(5):758-71.
Sternson et al., Split—pool synthesis of 1,3-dioxanes leading to arrayed stock solutions of single compounds sufficient for multiple phenotypic and protein-binding assays. J Am Chem Soc. Feb. 28, 2001;123(8):1740-7.
Sternson et al., Synthesis of 7200 small molecules based on a substructural analysis of the histone deacetylase inhibitors trichostatin and trapoxin. Org Lett. Dec. 27, 2001;3(26):4239-42.
Stevanovic et al., Natural and Synthetic Peptide Pools: Characterization by Sequencing and Electrospray Mass Spectrometry. Bioorg Med Chem Lett. 1993;3(3):431-36.
Stewart et al., Expression of retroviral vectors in transgenic mice obtained by embryo infection. EMBO J. Feb. 1987;6(2):383-8.
Stillman et al., Epistasis analysis of suppressor mutations that allow HO expression in the absence of the yeast SW15 transcriptional activator. Genetics. Mar. 1994;136(3):781-8.
Strebhardt et al., Additional member of the protein-tyrosine kinase family: the src- and lck-related protooncogene c-tkl. Proc Natl Acad Sci U S A. Dec. 1987;84(24):8778-82.
Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.
Suzuki et al., Synthesis and histone deacetylase inhibitory activity of new benzamide derivatives. J Med Chem. Jul. 29, 1999;42(15):3001-3.
Tallarico et al., An alkylsilyl-tethered, high-capacity solid support amenable to diversity-oriented synthesis for one-bead, one-stock solution chemical genetics. J Comb Chem. May-Jun. 2001;3(3):312-8.
Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.
Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.
Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.
Tao et al., Deacetylase inhibition promotes the generation and function of regulatory T cells. Nat Med. Nov. 2007;13(11):1299-307. Epub Oct. 7, 2007.
Taunton et al., A mammalian histone deacetylase related to the yeast transcriptional regulator Rpd3p. Science. Apr. 19, 1996;272(5260):408-11.
Taunton et al., Deacetylation. The Scientist. 1999;13:13.
Taunton et al., Synthesis of Natural and Modified Trapoxins, Useful Reagents for Exploring Histone Deacetylase Function. J Am Chem Soc. 1996;118:10412-22.
Thornton et al., Protein Engineering: Editorial Overview. Curr Opin Biotechnol. 1995;6(4):367-69.
Tissenbaum et al., Increased dosage of a sir-2 gene extends lifespan in Caenorhabditis elegans. Nature. Mar. 8, 2001;410(6825):227-30.
Tong et al., Chromatin deacetylation by an ATP-dependent nucleosome remodeling complex. Nature. 1997;395:917-21.
Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2. J Biol Chem. Nov. 27, 1998;273(48):31788-94.

Tsankova et al., Sustained hippocampal chromatin regulation in a mouse model of depression and antidepressant action. Nat Neurosci. Apr. 2006;9(4):519-25. Epub Feb. 26, 2006.

Turner, Decoding the nucleosome. Cell. Oct. 8, 1993;75(1):5-8.

Uchiyama et al., Adhesion of human myeloma-derived cell lines to bone marrow stromal cells stimulates interleukin-6 secretion. Blood. Dec. 15, 1993;82(12):3712-20.

Uong et al., Stereocontrolled Functionalization of Acyclic Molybdenum-$\eta^3$-Allyl Complexes: A New Approach to the Stereoselective Synthesis of 1,3-Diols. J Chem Soc Chem Commun. 1990:1285-87.

Urnov et al., Targeting of N-CoR and histone deacetylase 3 by the oncoprotein v-erbA yields a chromatin infrastructure-dependent transcriptional repression pathway. EMBO J. Aug. 1, 2000;19(15):4074-90.

Valerio et al., Multipin peptide synthesis at the micromole scale using 2-hydroxyethyl methacrylate grafted polyethylene supports. Int J Pept Protein Res. Jul. 1993;42(1):1-9.

Valerio et al., Synthesis of peptide analogues using the multipin peptide synthesis method. Anal Biochem. Aug. 15, 1991;197(1):168-77.

Van Der Krol et al., Modulation of eukaryotic gene expression by complementary RNA or DNA sequences. Biotechniques. Nov.-Dec. 1988;6(10):958-76.

Van Der Putten et al., Efficient insertion of genes into the mouse germ line via retroviral vectors. Proc Natl Acad Sci U S A. Sep. 1985;82(18):6148-52.

Vannini et al., Crystal structure of a eukaryotic zinc-dependent histone deacetylase, human HDAC8, complexed with a hydroxamic acid inhibitor. Proc Natl Acad Sci U S A. Oct. 19, 2004;101(42):15064-9. Epub Oct. 11, 2004.

Varga-Weisz et al., Chromatin-remodeling factors: machines that regulate? Curr Opin Cell Biol. Jun. 1998;10(3):346-53.

Vegas et al., Fluorous-based small-molecule microarrays for the discovery of histone deacetylase inhibitors. Angew Chem Int Ed Engl. 2007;46(42):7960-4.

Venter et al., The sequence of the human genome. Science. Feb. 16, 2001;291(5507):1304-51.

Verdel et al., Identification of a new family of higher eukaryotic histone deacetylases. Coordinate expression of differentiation-dependent chromatin modifiers. J Biol Chem. Jan. 22, 1999;274(4):2440-5.

Vidal et al., RPD3 encodes a second factor required to achieve maximum positive and negative transcriptional states in *Saccharomyces cerevisiae*. Mol Cell Biol. Dec. 1991;11(12):6317-27.

Vong et al., Regio- and Stereocontrolled Functionalization of Acyclic Molybdenum-$\eta^3$-Allyl Complexes. J Am Chem Soc. 1991;113:573-82.

Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J Biol Chem. Apr. 5, 1990;265(10):5736-46.

Wallace et al., Understanding cytochrome c function: engineering protein structure by semisynthesis. FASEB J. Apr. 1, 1993;7(6):505-15.

Wang et al., ETO, fusion partner in t(8;21) acute myeloid leukemia, represses transcription by interaction with the human N-CoR/mSin3/HDAC1 complex. Proc Natl Acad Sci U S A. Sep. 1, 1998;95(18):10860-5.

Wang et al., HDAC4, a human histone deacetylase related to yeast HDA1, is a transcriptional corepressor. Mol Cell Biol. Nov. 1999;19(11):7816-27.

Wang et al., Isolation of high-affinity peptide antagonists of 14-3-3 proteins by phage display. Biochemistry. Sep. 21, 1999;38(38):12499-504.

Wang et al., Zinc binding in HDAC inhibitors: a DFT study. J Org Chem. Jul. 6, 2007;72(14):5446-9. Epub Jun. 19, 2007.

Warrell et al., Therapeutic targeting of transcription in acute promyelocytic leukemia by use of an inhibitor of histone deacetylase. J Natl Cancer Inst. Nov. 4, 1998;90(21):1621-5.

Wegener et al., A fluorogenic histone deacetylase assay well suited for high-throughput activity screening. Chem Biol. Jan. 2003;10(1):61-8.

Weinberg, Finding the anti-oncogene. Sci Am. Sep. 1988;259(3):44-51.

Wennemers et al., Cyclooligomeric Receptors Based on Trimesic Acid and 1,2-Diamines. Minimal Structure for Sequence-Selective Peptide Binding. J Org Chem. 1995;60:1108-09.

Whelan et al., A general empirical model of protein evolution derived from multiple protein families using a maximum-likelihood approach. Mol Biol Evol. May 2001;18(5):691-9.

Wilen et al., Strategies in Optical Resolution. Tetrahedron. 1977;33:2725-36.

Witkowski et al., Conversion of a beta-ketoacyl synthase to a malonyl decarboxylase by replacement of the active-site cysteine with glutamine. Biochemistry. Sep. 7, 1999;38(36):11643-50.

Wong et al., Modular synthesis and preliminary biological evaluation of stereochemically diverse 1,3-dioxanes. Chem Biol. Sep. 2004;11(9):1279-91.

Wong et al., Structural biasing elements for in-cell histone deacetylase paralog selectivity. J Am Chem Soc. May 14, 2003;125(19):5586-7.

Workman et al., Alteration of nucleosome structure as a mechanism of transcriptional regulation. Annu Rev Biochem. 1998;67:545-79.

Xie et al., Sum1 and Hst1 repress middle sporulation-specific gene expression during mitosis in *Saccharomyces cerevisiae*. EMBO J. Nov. 15, 1999;18(22):6448-54.

Xu et al., Coactivator and corepressor complexes in nuclear receptor function. Curr Opin Genet Dev. Apr. 1999;9(2):140-7.

Xue et al., NURD, a novel complex with both ATP-dependent chromatin-remodeling and histone deacetylase activities. Mol Cell. Dec. 1998;2(6):851-61.

Yaffe et al., The structural basis for 14-3-3:phosphopeptide binding specificity. Cell. Dec. 26, 1997;91(7):961-71.

Yang et al., Cloning and characterization of two mouse genes with homology to the yeast Sir2 gene. Genomics. Nov. 1, 2000;69(3):355-69.

Yang et al., Isolation and characterization of cDNAs corresponding to an additional member of the human histone deacetylase gene family. J Biol Chem. Oct. 31, 1997;272(44):28001-7.

Yang et al., Maintenance of G2 arrest in the Xenopus oocyte: a role for 14-3-3-mediated inhibition of Cdc25 nuclear import. EMBO J. Apr. 15, 1999;18(8):2174-83.

Yang et al., Transcriptional repression by YY1 is mediated by interaction with a mammalian homolog of the yeast global regulator RPD3. Proc Natl Acad Sci U S A. Nov. 12, 1996;93(23):12845-50.

Yoon et al., Cyclooligomeric Receptors for the Sequence Selective Binding of Peptides. A Tetrahedral Receptor from the Trimesic Acid and 1,2-Diamines. Tetrahedron Lett. 1994;35:8557-60.

Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.

Yoshida et al., Potent and specific inhibition of mammalian histone deacetylase both in vivo and in vitro by trichostatin A. J Biol Chem. Oct. 5, 1990;265(28):17174-9.

Yoshida et al., Trichostatin A and trapoxin: novel chemical probes for the role of histone acetylation in chromatin structure and function. Bioessays. May 1995;17(5):423-28.

Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.

Yu et al., The proteasome inhibitor bortezomib interacts synergistically with histone deacetylase inhibitors to induce apoptosis in Bcr/Abl+ cells sensitive and resistant to STI571. Blood. Nov. 15, 2003;102(10):3765-74. Epub Jul. 31, 2003.

Zervos et al., Mxi1, a protein that specifically interacts with Max to bind Myc-Max recognition sites. Cell. Jan. 29, 1993;72(2):223-32.

Zhang et al., The dermatomyositis-specific autoantigen Mi2 is a component of a complex containing histone deacetylase and nucleosome remodeling activities. Cell. Oct. 16, 1998;95(2):279-89.

Zhou et al., Cloning and characterization of a histone deacetylase, HDAC9. Proc Natl Acad Sci U S A. Sep. 11, 2001;98(19):10572-7. Epub Sep. 4, 2001.

Zhou et al., Identification of a transcriptional repressor related to the noncatalytic domain of histone deacetylases 4 and 5. Proc Natl Acad Sci U S A. Feb. 1, 2000;97(3):1056-61.

Zimmermann et al., Conformational and epitope mapping of herpes-simplex-virus type-1 thymidine kinase using synthetic peptide segments. Eur J Biochem. Sep. 1, 1991;200(2):519-28.

Extended European Search Report for EP 09800666.1 mailed Aug. 24, 2011.

Office Communication, mailed Sep. 29, 2011, for U.S. Appl. No. 12/279,440.

Office Communication, mailed Nov. 29, 2011, for U.S. Appl. No. 12/299,430.

Office Communication, mailed Nov. 23, 2011, for U.S. Appl. No. 10/919,217.

CAS Registry File RN 505-22-6, STN Entry Date: Nov. 16, 1984.

[No Author Listed] Inhibitor. Available at http://www.biology-online.org/dictionary/inhibitor. Last accessed Apr. 7, 2011. 1 page.

Bundgaard, Chapter 1. Design of prodrugs: Bioreversible derivatives for various functional groups and chemical entities. In: Design of Prodrugs. Elsevier. 1985:1-4.

Marks et al., Polar/apolar chemical inducers of differentiation of transformed cells: strategies to improve therapeutic potential. Proc Natl Acad Sci U S A. Aug. 1989;86(16):6358-62.

Reuben et al., A new group of potent inducers of differentiation in murine erythroleukemia cells. Proc Natl Acad Sci U S A. Mar. 1976;73(3):862-6.

Zhu et al., Phosphine-catalyzed synthesis of 1,3-dioxan-4-ylidenes. Org Lett. Mar. 31, 2005;7(7):1387-90.

Extended European Search Report for EP 07872648.6 mailed Apr. 13, 2011.

Extended European Search Report for EP 07757000.0 mailed May 3, 2011.

Andrews et al., Anti-malarial effect of histone deacetylation inhibitors and mammalian tumour cytodifferentiating agents. Int J Parasitol. May 2000;30(6):761-8.

Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.

Breslow et al., Potent cytodifferentiating agents related to hexamethylenebisacetamide. Proc Natl Acad Sci U S A. Jul. 1, 1991;88(13):5542-6.

Dankwardt et al., Solid-phase synthesis of di- and tripeptidic hydroxamic acids as inhibitors of procollagen C-proteinase. Bioorg Med Chem Lett. Nov. 20, 2000;10(22):2513-6.

Farkas et al., A comparison between the chelating properties of some dihydroxamic acids, desferrrioxamine B and acetohydroxamic acid. Polyhedron. 1999;18(1999):2391-98.

Giacomelli et al., Simple one-flask method for the preparation of hydroxamic acids. Org Lett. Jul. 24, 2003;5(15):2715-7.

Hynes, Hydroxylamine derivatives as potential antimalarial agents. 1. Hydroxamic acids. J Med Chem. Nov. 1970;13(6):1235-7.

Khomutov et al., Directed synthesis of inhibitors of enzymic changes of glutamic acid. Doklady Akademii Nauk SSSR. 1965;161(5):1227-30. Russian.

Menger et al., Chemical Reaction between Colliding Vesicles. Chem Int Ed Engl. Oct. 15, 2001;40(20):3905-3907.

Munegumi et al., Amidation of carboxyl group involved in N-protected amino acids using O-benzylhydroxylamine. Peptide Chemistry. 1993;31:49-52.

Patani et al., Bioisosterism: A Rational Approach in Drug Design. Chem Rev. Dec. 19, 1996;96(8):3147-3176.

Singh et al., Chemistry and structure-activity relationship of HIV-1 integrase inhibitor integracide B and related natural products. J Nat Prod. Oct. 2003;66(10):1338-44.

Stowell et al., The synthesis of N-hydroxy-N'-phenyloctanediamide and its inhibitory effect on proliferation of AXC rat prostate cancer cells. J Med Chem. Apr. 14, 1995;38(8):1411-3.

U.S. Appl. No. 13/221,602, filed Aug. 30, 2011, Schreiber et al.

U.S. Appl. No. 13/221,561, filed Aug. 30, 2011, Schreiber et al.

Office Communication, mailed Jun. 20, 2011, for U.S. Appl. No. 12/279,440.

Notice of Allowance, mailed Jun. 8, 2011, for U.S. Appl. No. 12/196,878.

Notice of Allowance, mailed Aug. 17, 2011, for U.S. Appl. No. 12/370,390.

* cited by examiner

```
  1  MAQTQGTRRK VCYYYDGDVG NYYYGQGHPM KPHRIRMTHN LLLNYGLYRK MEIYRPHKAN AEEMTKYHSD
 71  DYIKFLRSIR PDNMSEYSKQ MQRFNVGEDC PVFDGLFEFC QLSTGGSVAS AVKLNKQQTD IAVNWAGGLH
141  HAKKSEASGF CYVNDIVLAI LELLKYHQRV LYIDIDIHHG DGVEEAFYTT DRVMTVSFHK YGEYFPGTGD
211  LRDIGAGKGK YYAVNYPLRD GIDDESYEAI FKPVMSKVME MFQPSAVVLQ CGSDSLSGDR LGCFNLTIKG
281  HAKCVEFVKS FNLPMLMLGG GGYTIRNVAR CWTYETAVAL DTEIPNELPY NDYFEYFGPD FKLHISPSNM
351  TNQNTNEYLE KIKQRLFENL RMLPHAPGVQ MQAIPEDAIP EESGDEDEDD PDKRISICSS DKRIACEEEF
421  SDSEEEGEGG RKNSSNFKKA KRVKTEDEKE KDPEEKKEVT EEEKTKEEKP EAKGVKEEVK LA
```

(SEQ ID NO: 5)

Fig. 3A

 αHD1
 αRbAp48
Fig. 4B

Sequences
1> SEQ ID NO: 1 HD1                                  5> SEQ ID NO: 18 R18769
2> RESIDUES 1-358 OF SEQ ID NO: 2 HSC11A021          6> SEQ ID NO: 19 D31480
3> RESIDUES 1-368 OF SEQ ID NO: 3 R21136             7> SEQ ID NO: 20 R98879
4> RESIDUES 61-227 OF SEQ ID NO: 4 F07807            8> SEQ ID NO: 21 N59055

```
          *         *         *         *         *        50
1> ATGGCGCAGACgCAGGGCACCCGGAGGAAAGTCTGTTACTACTACGACGGGGATGTTGGA
6> ATGGCGCAGACGCAGGGCACCCGGAGGAAAGTNTGTTACTACTACGACGGGGATGTTGGA

*         *         *         *        100         *
1> AATTACTATTATGGACAAGGCCACCCAATGAAGCCTCACCGAATCCGCATGACTCATAAT
6> AATTACTATTATGGACAAGGCCACCCAATGAAGCCTCACCGAATCCGCATGACTCATAAT

*         *         *        150         *         *
1> TTGCTGCTCAACTATGGTCTCTACCGAAAAATGGAAATCTATCGCCCTCACAAAGCCAAT
6> TTGCTGCTCAACTATGGTCTCTACCGAAAAATGGAAATCTATCGNCCTCACAAAGCCAAT

*         *        200         *         *         *
1> gCTGAGGAGATGACCAAGTACCACAGCGATGACTACATTAAATTCTTGCGCTCCATCCGT
2>                                             ATTGACTTCCTGCAGAGAGTCAGC
6> NCTGAGGAGATGACCAAGTANCACAGCGATGAC
7>                                                    TCCTGCAGAGAGTCAGC

*        250         *         *         *         *       300
1> CCAGATAACATGTCGGAGTACAGCAAGCAGATGCAGAGATTCAACGTTGGTGAGGACTGT
2> CCCACCAATATGCAAGGCTTCACCAAGAGTCTTAATGCCTTCAACGTAGGCGATGACTGC
5>                                                      CGATGACTGC
7> CCCACCAATATGCAAGGCTTCACCAAGAGTCTTAATGCCTTCAACGTAGGCGATGACTGC

*         *         *         *         *       359
1> CCAGTATTCGATGGCCTGTTTGAGTTCTGTCAGTTGTCTACTGGTGGTTCTGTGGCAAGT
2> CCAGTGTTTCCCGGGCTCTTTGAGTTCTGCTCGCGTTACACAGGCGCATCTCTGCAAGGA
5> CCAGTGTTTCCCGGGCTCTTTGAGTTCTGCTCGCGTTACACAGGCGCATCTCTGCAAGGA
7> CCAGTGTTTCCCGGGCTCTTTGAGTTCTGCTCGCGTTACACAGGCGCATCTCTGCAAGGA

*         *         *         *        400         *
1> GCTGTGAAACTTAATAAGCAGCAGACGGACATCGCTGTGAATTGGGCTGGGGGGCTGCAC
2> GCAACCCAGCTGAACAACAAGATCTGTGATATTGCCATTAACTGGGCTGGTGGTCTGCAC
5> GCAACCCAGCTGAACAACAAGATCTGTGATATTGCCATTAACTTGGCTGGTGGCTTNAAC
7> GCAACCCAGCTGAACAACAAGATCTGTGATATTGCCATTAACTGGGCTGGTNGTCTGCAC

*         *         *        450         *         *
1> CATGCAAAGAAGTCCGAGGCATCTGGCTTCTGTTACGTCAATGATATCGTCTTGGCCATC
2> CATGCCTAGAAGTTTGAGGCCTCTGGCTTCTGCTATGTCAACGACATTGTGTTTGGCATC
```

Fig. 5A-1

```
 5> NATGCCANGANGTTTNAGGCCTCTGGNTTCTGCTATGTCAACGACATTGTGATTGGCATC
 7> CATGCCAAGAAGTTTGAGGCCTCTGGTTTCTGCTATGTCAACGACATTGTGATTGGCATC

*         *        500         *         *         *
 1> CTGGAACTGCTAAAGTATCACCAGAGGGtgCTGTACATTGACATTGATATTCACCATGGT
 2> CTGGAGCTGCTCAAGTACCACCCTCGGGTGCTCTACATTGACATTGACATCCACCATGGT
 5> CTGGAGCTGCTCAAGTACCACCCTCGGGTGCTCTACATTGACATTGACATCCACCATGGT
 7> CTGGAGCTGCTCAAGTACCACCCTCGGGTGCTCTACATTGACATTGACATCCACCA

*        550         *         *         *         *        600
 1> GACGGCGTGGAAGAGGcCTTCTACACCACGGACCGGGTCATGACTGTGTCCTTTCATAAG
 2> GACGGGGTTCAAGAAGCTTTCTACCTCACTGACC
 5> GACGGGGTTCAAGAAGCTTTCTACCTCACTGACCGGGTCATGACGGTGTCCTTTCCACAA
10>                        CTACACCACGGACCGGGTCATGACTGTGTCCTTTCATAAG

*         *         *         *         *        650
 1> TATGGAGAGTACTTCCCAGGAACTGGGGACCTACGGGATATCGGGGCTGGCAAAGGCAAG
 5> ATACGGGAAATTTACTTNTTCCNGGGGCACAGGTGACATGTTNTGGAAGTTCGGGGGGCA
10>TATGGAGAGTACTTCCCAGGGACTTGGGACCTACGGGATATCGGGGCTGGCAAAGGCAAG

*         *         *         *        700         *
 1> TATTATGCTGTTAACTACCCGCTCCGAGACGGGATTGATGACGAGTCCTATGAGGCCATT
 3> TACTACTGTCTGAACGTGCCCCTGCGGATGGGCATTGATGACCAGAGTTACAAGCACCTT
 5> GGAGAGTTGGCCC
10>TATTATGCTGTTAACTACCCGCTCCGAGACGGGATTNATGACGAGTCCTATGAGGCCATT

*         *         *        750         *         *
 1> TTCAAGCCGGTCATGTCCAAAGTAATGGAGATGTTCCAGCCTAGTGCGGTGGTCTTACAG
 3> TTCCAGCCGGTTATCAACCAGGTAGTGGACTTCTACCAACCCACGTGCATTGTGCTCCAG
 8>                                          CCCTATAGTGAGTCGTATTNN
10>TTCAAGCCGGTCATGTCCAAAGTAATNGAGATGTTCCAGCCTAGTGCG

*         *        800         *         *         *
 1> TGTGGCTCAGACTCCCTATCTGGGGATCGGTTAGGTTGCTTCAATCTAACTATCAAAGGA
 3> TGTGGAGCTGACTCTCTGGGCTGTGATCGATTGGGCTGCTTTAACCTCAGCATCCGAGGG
 8> TNAAAACATGACTCACTNGGNTNNNTACGATTGGGCTGCTTTAACCTCAGCATCCGAGGG
 9>                                                          AGGT

*        850         *         *         *         *        900
 1> CACgCCAAGTGTGTGGAATTTGTCAAGAGCTTTAACCTGCCTATGCTGATGCTGGGAGGC
 3> CATGGGGAATGCGTTGAATATGTCAAGAGCTTCAATATCCCTCTACTCGTGCTGGGTGGT
 4>                                                           GGA
 8> CATGGGNAATGCGTTGAATATGTCAAGAGCTTCAATATCCCTCTACTCGTGCTGGGTGGT
 9> NATGCTAAATGTGTAGAAGTTGTAAAAACTTTTAACTTACCATTACTGATGCTTGGAGGA
```

Fig. 5A-2

```
            *         *         *         *         *       950
1>  GGTGGTTACACCATTCGTAACGTTGCCCGGTGCTGGACATATGAGACAGCTGTGGCCCTG
3>  GGTGGTTATACTGTCCGAAATGTTGCCCGCTGCTGGACATATGAGACATCGCTGCTGGTA
4>  GGTGGCTACACAATCCGTAATGTTGCTCGATGTTGGACATATGAGACTGCAGTTGCCCTT
8>  GGTGGTTATACTGTCCGAAATGTNGCCCGCTGCTGGACATATGAGACANCGCTGCTGGTA
9>  GGTGGCTACACAATCCGTAATGTTGCTCGATGTTGGACATATGAGACTGCAGTTGCCCTT

*         *         *         *       1000        *
1>  GATACGGAGATCCCTAATGAGCTTCCATACaATGACTACTTTGAATACTTTGGACCAGAT
3>  GAAGAGGCCATTAGTGAGGAGCTTCCCTATAGTGAATACTTCGAGTACTTTGCCCCAGAC
4>  GATTGTGAGATTCCCAATGAGTTGCCATATAATGATTACTTTGAGTATTTTGGACCAGAC
8>  GAAGAGGCCATTAGTGAGGAGCTTCCCTAATAGTGAATACTTCGNTACTTTGCCCCAGAC
9>  GATTGTGAGATTCCCAATGGTAAGTGTTCTCATTACAATATCTTTATTGTATG

*         *         *      1050        *         *
1>  TTCAAGCTCCACATCAGTCCTTCCAATATGACTAACCAGAACACGAATGAGTACCtGGAG
3>  TTCACACT
4>  TTCAAACTGCATATTAGTCCTTCAAACATGACAAACCAGAACAC
8>  TTCACACTTCATCCANATGTCAGCACCCGCATCGAGAATCCAGAACTCACGCCAGTATC

*         *      1100        *         *         *
1>  AAGATCAAACAGCGACTGTTTGAGAACCTTAGAATGCTGCCGCACGCACCTGGGGTCCAA
8>  NGGACCAAGATCCGCCAGACAATCTTTGNAAACCTGAAGGTTCTTNAACC

*      1150        *         *         *         *      1200
1>  ATGCAGGCGATTCCTGAGGACGCCATCCCTGAGGAGAGTGGCGATGAGGACGAAGACGAC

*         *         *         *         *      1250
1>  CCTGACAAGCGCATCTCGATCTGCTCCTCTGACAAACGAATTGCCTGTGAGGAAGAGTTC

*         *         *         *      1300        *
1>  TCCGATTCTGAAGAGGAGGGAGAGGGGGGCCGCAAGAACTCTTCCAACTTCAAAAAAGCC

*         *         *      1350        *         *
1>  AAGAGAGTCAAAACAGAGGATGAAAAAGAGAAAGACCCAGAGGAGAAGAAAGAAGTCACC

*         *      1400        *         *         *
1>  GAAGAGGAGAAAACCAAGGAGGAGAAGCCAGAAGCCAAAGGGGTCAAGGAGGAGGTCAAG

1>  TTGGCCTGA

9>  SEQ ID NO: 22 F06693
10> SEQ ID NO: 23 H05234
3>  RESIDUES 1-368 OF SEQ ID NO: 3 R21136
```

Fig. 5A-3

```
SEQ ID NO: 5   HD1      (1)   ----------maqtqGTRRKVCYYYDGDVGNYYYGQGHPMKPHRIRMTHNLLLNYGLYRK
SEQ ID NO: 9   RPD3     (1)   mvyeatpfdpITVKPSDKRRVAYFYDADVGNYAYGAGHPMKPHRIRMAHSLIMNYGLYKK
SEQ ID NO: 10  x_rpd3   (1)   ----------MALTLGTKKKVCYYYDGDVGNYYYGQGHPMKPHRIRMTHNLLLNYGLYRK SEQ ID NO: 6          <EstA>         IDFLQRVSPTNMQGFTKSLNAFNVGDDCPVFPGLFEFC
                      HD1      (51)  MEIYRPHKANAEEMTKYHSDDYIKFLRSIRPDNMSEYSKQMQRFNVGEDCPVFDGLFEFC
                      RPD3     (61)  MEIYRAKPATKQEMCQFHTDEYIDFLSRVTPDNLEMFKRESVKFNVGDDCPVFDGLYEYC x_rpd3   (51)  MEIFRPHKASAEDMTKYHSDDYIKFLRSIRPDNMSEYSKQMQRFNVGEDCPVFDGLFEFC
                      <EstA>         SRYTGASLQGATQLNNKICDIAINWAGGLHHAKKFEASGFCYVNDIVFGILELLKYHPRV
                      HD1      (111) QLSTGGSVASAVKLNKQQTDIAVNWAGGLHHAKKSEASGFCYVNDIVLAILELLKYHQRV
                      RPD3     (121) SISGGGSMEGAARLNRGKCDVAVNYAGGLHHAKKSEASGFCYLNDIVLGIIELLRYHPRV
                      x_rpd3   (111) QLSAGGSVASAVKLNKQQTDISVNWSGGLHHAKKSEASGFCYVNDIVLAILELLKYHQRV SEQ ID NO: 7          <EstB>                                              YYCLNVPLRM
                      <EstA>         LYIDIDIHHGDGVQEAFYLTDRVMTVSFPQIREIY
                      HD1      (171) LYIDIDIHHGDGVEEAFYTTDRVMTVSFHKYGEYFPGTGDLRDIGAGKGKYYAWNYPLRD
                      RPD3     (181) LYIDIDVHHGDGVEEAFYTTDRVMTCSFHKYGEFFPGTGELRDIGVGAGKNYAVNVPLRD
                      x_rpd3   (171) VYIDIDIHHGDGVEEAFYTTDRVMTVSFHKYGEYFPGTGDLRDIGAGKGKYYAVNYALRD SEQ ID NO: 8          <EstC>                                                NLLVLGHAKCVEVVKT
                      <EstB>         GIDDQSYKHLFQPVINQVVDFYQPTCIVLQCGADSLGCDRLGCFNLSIRGHGECVEYVKS
                      HD1      (231) GIDDESYEAIFKPVMSKVMEMFQPSAVVLQCGSDSLSGDRLGCFNLTIKGHAKCVEFVKS
                      RPD3     (241) GIDDATYRSVFEPVIKKIMEWYQPSAVVLQCGGDSLSGDRLGCFNLSMEGHANCVNYVKS
                      x_rpd3   (231) GIDDESYEAIFKPVMSKVMEMFQPSAVVLQCGADSLSGDRLGCFNLTIKGHAKCVEFIKT <EstC>         FNLPLLMLGGGGYTIRNVARCWTYETAVALDCEIPNELPYNDYFEYFGPDFKLHISPSNM
                      <EstB>         FNIPLLVLGGGGYTVRNVARCWTYETSLLVEEAISEELPYSEYFEYFAPDFTLHP
                      HD1      (291) FNLPMLMLGGGGYTIRNVARCWTYETAVALDTEIPNELPYNDYFEYFGPDFKLHISPSNM
                      RPD3     (301) FGIPMMVVGGGGYTMRNVARTWCFETGLLNNVVLDKDLPYNEYYEYYGPDYKLSVRPSNM
                      x_rpd3   (291) FNLPLLMLGGGGYTIRNVARCWTYETAVALDSEIPNELPYNDYFEYFGPDFKLHISPSNM <EstC>         TNQN
                      <HD1>          TNQNTNEYLEKIKQRLFENLRMLPHAPGVQMQAIPEDAIPEESGDEDEDDPDKRISICSS
                      RPD3     (361) FNVNTPEYLDKVMTNIFANLENTKYAPSVQLNHTPRDaedlgdveedsaeakdtkggsqy
                      x_rpd3   (351) TNQNTNEYLEKIKQRLFENLRMLPHAPGVQMQAVAEDSIHDDSGEEDEDDPDKRISIRSS HD1      (411) DKRIACEEEFSDSEEEGEGGRKNSSNFKKAKRVKTEDEKEkdPEEKKEVTEEEKTKEEKP
                      RPD3     (421) ardlhvehdnefy-----------------------------------------------
                      x_rpd3   (411) DKRIACDEEFSDSEDEGEGGRKNVANFKKVKRVKTEEEKE--GEDKKDVKEEEKAKDEKT HD1      (471) EAKGVKEEVKla
                      RPD3     (434) ------------
                      x_rpd3   (469) DSKRVKEETKsv              Fig. 5B
```

HISTONE DEACETYLASES, AND USES RELATED THERETO

RELATED APPLICATIONS

The present application claims priority under 35 U.S.C. §120 to and is a continuation of U.S. patent application Ser. No. 12/196,878, filed Aug. 22, 2008, now U.S. Pat. No. 7,994,362, which claims priority under 35 U.S.C. §120 to and is a continuation of U.S. patent application Ser. No. 10/919,217, filed Aug. 16, 2004, which claims priority under 35 U.S.C. §120 to and is a divisional of U.S. patent application Ser. No. 08/624,735, filed Mar. 26, 1996, now issued as U.S. Pat. No. 6,777,217; each of which is incorporated herein by reference.

GOVERNMENT FUNDING

Word described herein was supported in part by funding from the National Institutes of Health. The United States Government has certain rights in the invention.

BACKGROUND OF INVENTION

The organization of regulatory DNA elements into precise chromatin structures is important for both DNA replication and transcription in vivo (Lee et al. (1993) Cell 72:73-84; Felsenfeld (1992) Nature. 355:209). In eukaryotic cells, nuclear DNA exists as a hierarchy of chromatin structures, resulting in the compaction of nuclear DNA about 10,000 fold (Davie and Hendzel (1994) J. Cell. Biochem. 55:98). The repeating structural unit in the extended 10 nm fibre form of chromatin is the nucleosome (van Holde (1988) *Chromatin*. New York: Springer-Verlag). The nucleosome consists of 146 bp of DNA wrapped around a protein core of the histones H2A, H2B, H3, and H4, known as the core histones. These histones are arranged as an $(H3-H4)_2$ tetramer and two H2A-H2B dimmers positioned on each face of the tetramer. The DNA joining the nucleosomes is called link DNA; it is to the linker DNA to which the H1 or linker histones bind. The 10 nm fibre is compacted further into the 30 nm fibre. Linker histones and amino-terminal regions ("tails") of the core histones maintain the higher order folding of chromatin (Garcia Ramirez et al. (1992) J. Biol Chem 267:19587). This chromatin structure must be relaxed when DNA is transcribed or translated.

Histones of the nucleosome core particle are subject to reversible acetylation at the ε-amino group of lysines present in their amino terminus (Csordas et al. (1990) *Biochem J* 265:23-38). Transcriptionally silent regions of the genome are enriched in underacetylated histone H4 (Turner (1993) *Cell* 75:5-8), and histone hyperacetylation facilitates the ability of transcription factor TFIIIA to bind to chromatin templates (Lee et al. (1993) *Cell* 72:73-84). Recent genetic, biochemical and immunological approaches have provided substantial evidence indicating that histones associated with actively transcribed genes are more highly acetylated than those from nontranscribed regions. While not wishing to be bound by any particular theory, histone acetylation may influence transcription at several stages, for example, by causing transcription factors to bind or by inducing structural transitions in chromatin, or by facilitating histone displacement and repositioning during polymerase elongation.

The acetylation and deacetylation are catalyzed by specific enzymes, histone acetyltransferase and deacetylase, respectively, and the net level of the acetylation is controlled by the equilibrium between these enzymes. The steady state level of acetylation and the rates at which acetate groups are turned over vary both between and within different cell types, with half-lives that vary from a few minutes to several hours. Although a histone acetyltransferase gene (HAT1) has been identified in yeast (Kelff et al. (1995) *J. Biol. Chem.* 270: 24674-24677), the molecular entities responsible for histone deacetylation were heretofore unknown in the art.

The identification of the mechanism by which histones are deacetylated would be of great benefit in the control of gene transcription and the cell cycle.

SUMMARY OF THE INVENTION

The present invention relates to the discovery of a novel family of genes, and gene products, expressed in mammals, which genes are referred to hereinafter as the "histone deacetylase" genes or "HDx" gene family, the products of which are referred to as histone deacetylases or HDx proteins.

In general, the invention features isolated HDx polypeptides, preferably substantially pure preparations of one or more of the subject HDx polypeptides. The invention also provides recombinantly produced HDx polypeptides. In preferred embodiments the polypeptide has a biological activity including an ability to deacetylate an acetylated histone substrate, preferably a substrate analog of histone H3 and/or H4. In other embodiments the HDx polypeptides of the present invention bind to trapoxin or to trichostatin, such binding resulting in the inhibition a deacetylase activity of the HDx polypeptide. However, HDx polypeptides which specifically antagonize such activities, such as may be provided by dominant negative mutants, are also specifically contemplated.

The HDx polypeptides disclosed herein are capable of modulating proliferation, survival and/or differentiation of cells, because of their ability to alter chromatin structure by deacetylating histones such as H3 or H4. Moreover, in preferred embodiments, the subject HDx proteins have the ability to modulate cell growth by influencing cell cycle progression or to modulate gene transcription.

In one embodiment, the polypeptide is identical with or homologous to an HDx protein. Exemplary HDx polypeptide include amino acid sequences represented in any one of SEQ ID Nos 5-8. Related members of the HDx family are also contemplated, for instance, an HDx polypeptide preferably has an amino acid sequence at least 85% homologous to a polypeptide represented by one or more of the polypeptides designated SEQ ID Nos: 5-8, though polypeptides with higher sequence homologies of, for example, 88, 90% and 95% or are also contemplated. In one embodiment, the HDx polypeptide is encoded by a nucleic acid which hybridizes under stringent conditions with a nucleic acid sequence represented in one or more of SEQ ID Nos. 1-4. Homologs of the subject HDx proteins also include versions of the protein which are resistant to post-translation modification, as for example, due to mutations which alter modification sites (such as tyrosine, threonine, serine or asparagine residues), or which inactivate an enzymatic activity associated with the protein.

The HDx polypeptide can comprise a full length protein, such as represented in SEQ ID No. 5, or it can comprise a fragment corresponding to particular motifs/domains, or to arbitrary sizes, e.g., at least 5, 10, 25, 50, 100, 150 or 200 amino acids in length. In preferred embodiments, the polypeptide, or fragment thereof, specifically deacetylates histone H4. In other preferred embodiments, the HDx polypeptide includes both a ν motif (SEQ ID No. 12) and a χ motif (SEQ ID No. 14), preferably a ν motif represented in the general formula SEQ ID No. 13, and a χ motif represented in the general formula SEQ ID No. 15.

In certain preferred embodiments, the invention features a purified or recombinant HDx polypeptide having a molecular weight in the range of 40 kd to 60 kd. For instance, preferred HDx polypeptides, have molecular weights in the range of 50 kd to about 60 kd, even more preferably in the range of 53-58 kd. It will be understood that certain post-translational modifications, e.g., phosphorylation, prenylation and the like, can increase the apparent molecular weight of the HDx protein relative to the unmodified polypeptide chain.

The subject proteins can also be provided as chimeric molecules, such as in the form of fusion proteins. For instance, the HDx protein can be provided as a recombinant fusion protein which includes a second polypeptide portion, e.g., a second polypeptide having an amino acid sequence unrelated (heterologous) to the HDx polypeptide, e.g. the second polypeptide portion is glutathione-S-transferase, e.g. the second polypeptide portion is an enzymatic activity such as alkaline phosphatase, e.g. the second polypeptide portion is an epitope tag.

In yet another embodiment, the invention features a nucleic acid encoding a an HDx polypeptide, or polypeptide homologous thereto, which polypeptide has the ability to modulate, e.g., either mimic or antagonize, at least a portion of the activity of a wild-type HDx polypeptide. Exemplary HDx-encoding nucleic acid sequences are represented by SEQ ID Nos: 1-4.

In another embodiment, the nucleic acid of the present invention includes a coding sequence which hybridizes under stringent conditions with one or more of the nucleic acid sequences in SEQ ID Nos: 1-4. The coding sequence of the nucleic acid can comprise a sequence which is identical to a coding sequence represented in one of SEQ ID Nos: 1-4, or it can merely be homologous to one or more of those sequences. In preferred embodiments, the nucleic acid encodes a polypeptide which specifically modulates, by acting as either an agonist or antagonist, the enzymatic activity of an HDx polypeptide.

Furthermore, in certain preferred embodiments, the subject HDx nucleic acid will include a transcriptional regulatory sequence, e.g. at least one of a transcriptional promoter or transcriptional enhancer sequence, which regulatory sequence is operably linked to the HDx gene sequence. Such regulatory sequences can be used in to render the HDx gene sequence suitable for use as an expression vector. This invention also contemplates the cells transfected with said expression vector whether prokaryotic or eukaryotic and a method for producing HDx proteins by employing said expression vectors.

In yet another embodiment, the nucleic acid hybridizes under stringent conditions to a nucleic acid probe corresponding to at least 12 consecutive nucleotides of either sense or antisense sequence of one or more of SEQ ID Nos: 1-4; though preferably to at least 25 consecutive nucleotides; and more preferably to at least 40, 50 or 75 consecutive nucleotides of either sense or antisense sequence of one or more of SEQ ID Nos: 1-4.

Yet another aspect of the present invention concerns an immunogen comprising an HDx polypeptide in an immunogenic preparation, the immunogen being capable of eliciting an immune response specific for an HDx polypeptide; e.g. a humoral response, e.g. an antibody response; e.g. a cellular response. In preferred embodiments, the immunogen comprising an antigenic determinant, e.g. a unique determinant, from a protein represented by one of SEQ ID Nos: 5-8.

A still further aspect of the present invention features antibodies and antibody preparations specifically reactive with an epitope of the HDx immunogen.

The invention also features transgenic non-human animals, e.g. mice, rats, rabbits, chickens, frogs or pigs, having a transgene, e.g., animals which include (and preferably express) a heterologous form of an HDx gene described herein, or which misexpress an endogenous HDx gene, e.g., an animal in which expression of one or more of the subject HDx proteins is disrupted. Such a transgenic animal can serve as an animal model for studying cellular and tissue disorders comprising mutated or mis-expressed HDx alleles or for use in drug screening.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequence of SEQ ID Nos: 1-4, or naturally occurring mutants thereof. Nucleic acid probes which are specific for each of the HDx proteins are contemplated by the present invention, e.g. probes which can discern between nucleic acid encoding a human or bovine HD. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of an HDx protein, such as for detecting in a sample of cells isolated from a patient, a level of a nucleic acid encoding a subject HDx protein; e.g. measuring an HDx mRNA level in a cell, or determining whether a genomic HDx gene has been mutated or deleted. These so called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject HDx proteins so as to inhibit expression of that protein, e.g. by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, of an interaction between an HDx protein and an HDx binding protein or nucleic acid sequence. An exemplary method includes the steps of (i) combining an HDx polypeptide or fragment thereof, an HDx target polypeptide (such as a histone or RpAp48), and a test compound, e.g., under conditions wherein, but for the test compound, the HDx protein and target polypeptide are able to interact; and (ii) detecting the formation of a complex which includes the HDx protein and the target polypeptide either by directly quantitating the complex, the deacetylase activity of the HDx protein, or by measuring inductive effects of the HDx protein. A statistically significant change, such as a decrease, in the formation of the complex in the presence of a test compound (relative to what is seen in the absence of the test compound) is indicative of a modulation, e.g., inhibition, of the interaction between the HDx protein and its target polypeptide.

Furthermore, the present invention contemplates the use of other homologs of the HDx polypeptides or bioactive fragments thereof to generate similar assay formats. In one embodiment, the drug screening assay can be derived with a fungal homolog of an HDx protein, such as RPD3, in order to identify agents which inhibit histone deacetylation in a yeast cell.

Yet another aspect of the present invention concerns a method for modulating one or more of growth, differentiation, or survival of a mammalian cell by modulating HDx bioactivity, e.g., by inhibiting the deacetylase activity of HDx proteins, or disrupting certain protein-protein interactions. In general, whether carried out in vivo, in vitro, or in situ, the method comprises treating the cell with an effective amount of an HDx therapeutic so as to alter, relative to the cell in the absence of treatment, at least one of (i) rate of growth, (ii) differentiation, or (iii) survival of the cell. Accordingly, the method can be carried out with HDx therapeutics such as peptide and peptidomimetics or other molecules identified in the above-referenced drug screens which antagonize the effects of a naturally-occurring HDx protein on said cell. Other HDx therapeutics include antisense constructs for inhibiting expression of HDx proteins, and dominant negative mutants of HDx proteins which competitively inhibit protein-substrate and/or protein-protein interactions upstream and downstream of the wild-type HDx protein.

In an exemplary embodiment the subject method is used to treat tumor cells by antagonizing HDx activity and blocking cell cycle progression. In one embodiment, the subject method includes the treatment of testicular cells, so as modulate spermatogenesis. In another embodiment, the subject method is used to modulate osteogenesis, comprising the treatment of osteogenic cells with an HDx polypeptide. Likewise, where the treated cell is a chondrogenic cell, the present method is used to modulate chondrogenesis. In still another embodiment, HDx polypeptides can be used to modulate the differentiation of progenitor cells, e.g., the method can be used to cause differentiation of a hematopoietic cells, neuronal cells, or other stem/progenitor cell populations, to maintain a that cell in a differentiated state, and/or to enhance the survival of a differentiated cell, e.g., to prevent apoptosis or other forms of cell death.

In addition to such HDx therapeutic uses, anti-fungal agents developed with such screening assays as described herein can be used, for example, as preservatives in foodstuff, feed supplement for promoting weight gain in livestock, or in disinfectant formulations for treatment of non-living matter, e.g., for decontaminating hospital equipment and rooms. In similar fashion, assays provided herein will permit selection of deacetylase inhibitors which discriminate between the human and insect deacetylase enzymes. Accordingly, the present invention expressly contemplates the use and formulations of the deacetylase inhibitors in insecticides, such as for use in management of insects like the fruit fly. Moreover, certain of the inhibitors can be selected on the basis of inhibitory specificity for plant HDx-related activities relative to the mammalian enzymes. Thus, the present invention specifically contemplates formulations of deacetylase inhibitors for agricultural applications, such as in the form of a defoliant or the like.

The present method is applicable, for example, to cell culture technique, such as in the culturing of hematopoietic cells and other cells whose survival or differentiative state is dependent on HDx function. Moreover, HDx agonists and antagonists can be used for therapeutic intervention, such as to enhance survival and maintenance of cells, as well as to influence organogenic pathways, such as tissue patterning and other differentiation processes. In an exemplary embodiment, the method is practiced for modulating, in an animal, cell growth, cell differentiation or cell survival, and comprises administering a therapeutically effective amount of an HDx polypeptide to alter, relative the absence of HDx treatment, at least one of (i) rate of growth, (ii) differentiation, or (iii) survival of one or more cell-types in the animal.

Another aspect of the present invention provides a method of determining if a subject, e.g. a human patient, is at risk for a disorder characterized by unwanted cell proliferation or aberrant control of differentiation. The method includes detecting, in a tissue of the subject, the presence or absence of a genetic lesion characterized by at least one of (i) a mutation of a gene encoding an HDx protein, e.g. represented in one of SEQ ID Nos: 1-4, or a homolog thereof; or (ii) the misexpression of an HDx gene. In preferred embodiments, detecting the genetic lesion includes ascertaining the existence of at least one of: a deletion of one or more nucleotides from an HDx gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of an HDx gene, e.g. a nucleic acid represented in one of SEQ ID Nos: 1-4, or naturally occurring mutants thereof, or 5' or 3' flanking sequences naturally associated with the HDx gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the HDx gene and, optionally, of the flanking nucleic acid sequences. For instance, the probe/primer can be employed in a polymerase chain reaction (PCR) or in a ligation chain reaction (LCR). In alternate embodiments, the level of an HDx protein is detected in an immunoassay using an antibody which is specifically immunoreactive with the HDx protein.

In another aspect, the invention provides compounds useful for inhibition of HDxs. In a preferred embodiment, an HDx inhibitor compound of the invention can be represented by the formula A-B-C, in which A is a specificity element for selective binding to an HDx, B is a linker element, and C is an electrophilic moiety capable of reacting with a nucleophilic moiety of an HDx; with the proviso that the compound is not butyrate, trapoxin, or trichostatin.

For instance, in one embodiment, there is provided a composition for inhibiting a histone deacetylase comprising a compound represented by the general formula A-B-C, wherein A is selected from the group consisting of cycloalkyls, unsubstituted and substituted aryls, heterocyclyls, amino acyls, and cyclopeptides;

B is selected from the group consisting of substituted and unsubstituted $C_4$-$C_8$ alkylidenes, $C_4$-$C_8$ alkenylidenes, $C_4$-$C_8$ alkynylidenes, and -(D-E-F)-, in which D and F are, independently, absent or represent a $C_2$-$C_7$ alkylidene, a $C_2$-$C_7$ alkenylidene or a $C_2$-$C_7$ alkynylidene, and E represents O, S, or NR', in which R' represents H, a lower alkyl, a lower alkenyl, a lower alkynyl, an aralkyl, aryl, or a heterocyclyl; and C is selected from the group consisting of

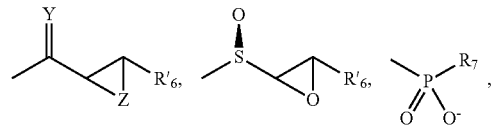

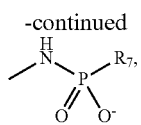

and a boronic acid; in which Z represents O, S, or NR$_5$, and Y; R$_5$ represents a hydrogen, an alkyl, an alkoxycarbonyl, an aryloxycarbonyl, an alkylsulfonyl, an arylsulfonyl or an aryl; R'$_6$ represents hydrogen, an alkyl, an alkenyl, an alkynyl or an aryl; and R$_7$ represents a hydrogen, an alkyl, an aryl, an alkoxy, an aryloxy, an amino, a hydroxylamino, an alkoxylamino or a halogen; with the proviso that the compound is not trapoxin.

In another preferred embodiment, the compound represented by the general formula A-B-C, wherein A is selected from the group consisting of cycloalkyls, unsubstituted and substituted aryls, heterocyclyls, amino acyls, and cyclopeptides;

B is selected from the group consisting of substituted and unsubstituted C$_4$-C$_8$ alkylidenes, C$_4$-C$_8$ alkenylidenes, C$_4$-C$_8$ alkynylidenes, and -(D-E-F)-, in which D and F are, independently, absent or represent C$_2$-C$_7$ alkylidenes, C$_2$-C$_7$ alkenylidenes or C$_2$-C$_7$ alkynylidenes, and E represents O, S, or NR', in which R' represents H, a lower alkyl, a lower alkenyl, a lower alkynyl, an aralkyl, an aryl, or a heterocyclyl; and C is selected from the group consisting of

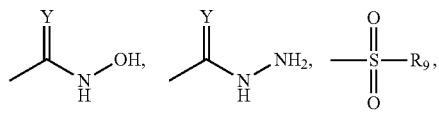

in which R$_9$ represents a hydrogen, an alkyl, an aryl, a hydroxyl, an alkoxy, an aryloxy or an amino,
with the proviso that the inhibitor compound is not trichostatin.

In still another preferred embodiment, the compound is represented by the general formula A-B-C, wherein A is selected from the group consisting of cycloalkyls, unsubstituted and substituted aryls, heterocyclyls, amino acyls, and cyclopeptides;

B is selected from the group consisting of substituted and unsubstituted C$_4$-C$_8$ alkylidenes, C$_4$-C$_8$ alkenylidenes, C$_4$-C$_8$ alkynylidenes, and -(D-E-F)-, in which D and F are, independently, absent or a C$_2$-C$_7$ alkylidene, a C$_2$-C$_7$ alkenylidene, or a C$_2$-C$_7$ alkynylidene, and E represents O, S, or NR', in which R' is H, lower alkyl, lower alkenyl, lower alkynyl, aralkyl, aryl, or heterocyclyl; and C represents

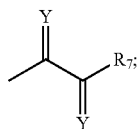

in which Y is O or S, and R$_7$ represents a hydrogen, an alkyl, an aryl, an alkoxy, an aryloxy, an amino, a hydroxylamino, an alkoxylamino or a halogen.

The present invention also contemplates pharmaceutical preparations of such compounds, e.g., in an amount effective for inhibiting proliferation of a cell, formulated in a pharmaceutically acceptable diluent.

Moreover, such compounds can be used for modulating one or more of growth, differentiation, or survival of a mammalian cell responsive to HDx-mediated histone deacetylation, by treating the cell with an effective amount of the deacetylase inhibitor so as to modulate the deacetylase activity and alter, relative to the cell in the absence of the agent, at least one of (i) the rate of growth, (ii) the differentiation state, or (iii) the rate of survival of the cell.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 3A is the predicted amino acid sequence of human HD1. An in-frame stop codon was found upstream of the starting methionine. Regions equivalent to microsequenced tryptic peptides from the purified bovine protein are boxed. Underlined amino acids 319-334 and 467-482 denote the sequences of synthetic peptides that were conjugated to KLH and used to generate polyclonal antisera. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIG. 4B shows the coprecipitation of HD1 and RbAp48, as detected by protein immunoblot analysis.

FIGS. 5A and 5B are sequence alignments for various HDx and HDx-related cDNAs and proteins, respectively.

DETAILED DESCRIPTION OF THE INVENTION

Figure 1A:
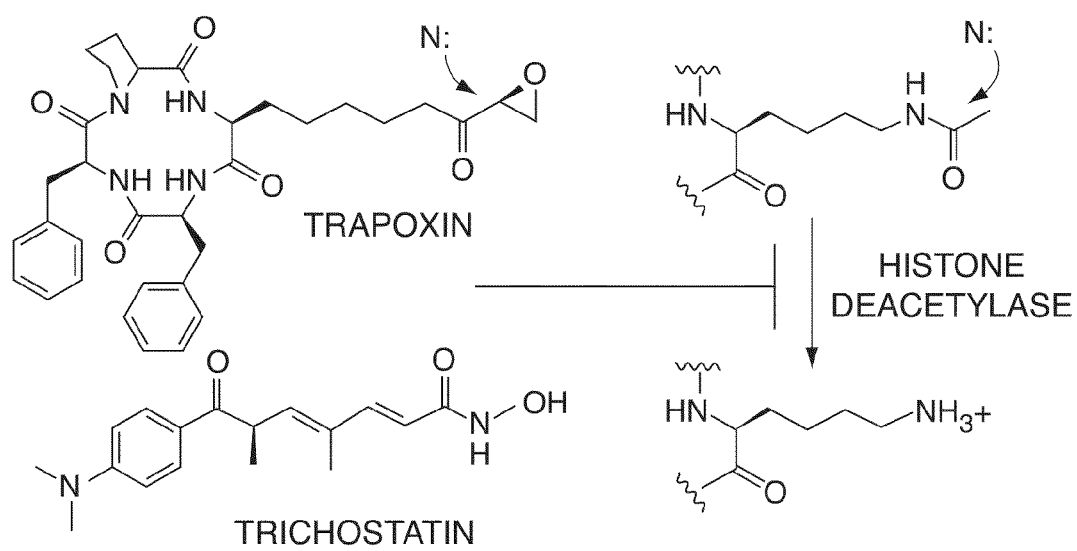
FIG. 1A illustrates the chemical structures of trapoxin and trichostatin, natural products that inhibit the enzymatic deacetylation of lysine residues near the NH$_2$-terminus of histones. The epoxyketone side chain of trapoxin is approximately isosteric with N-acetyl lysine and likely alkylates an active site nucleophile.

The positioning of nucleosomes relative to particular regulatory elements in genomic DNA has emerged as a mechanism for managing the association of sequence-specific DNA-binding proteins with promoters, enhancers and other transcriptional regulatory sequences. Two modifications to nucleosomes have been observed to influence the association of DNA-binding proteins with chromatin. Depletion of histones H2A/H2B from the nucleosome facilitates the binding of RNA polymerase II (Baer et al. (1983) *Nature* 301:482-488) and TFIIIA (Hayes et al. (1992) *PNAS* 89:1229-1233). Likewise, acetylation of the core histones apparently destabilizes the nucleosome and is thought to modulate the accessibility of transcription factors to their respective enhancer and promoter elements (Oliva et al. (1990) *Nuc Acid Res* 18:2739-2747; and Walker et al. (1990) *J Biol Chem* 265: 5622-5746). In both cases, overall histone-DNA contacts are altered.

In one aspect, the present invention concerns the discovery of a family of genes in mammals, the gene products of which are referred to herein as "histone deacetylases" or "HDx's". Experimental evidence indicates a functional role for the HDx gene products as catalysts of the deacetylation of histones in mammalian cells, and accordingly play a role in determining tissue fate and maintenance. For instance, the results provided below indicate that proteins encoded by the HDx genes may participate, under various circumstances, in the control of proliferation, differentiation and cell death.

The family of HDx gene apparently encode at least three different sub-families, e.g., paralogs, and have been identified from the cells of various mammals. The HDx proteins were first isolated from bovine thymus nuclei by use of a binding assay which exploited the ability of trapoxin, an inhibitor of histone deacetylase activity, to isolate proteins which co-purified with a histone acetylase activity. The partial identity of the isolated proteins were determined by peptide microsequencing, and primers based on the peptide sequences were used to clone human cDNAs from a T cell library. One of the HDx gene products described below is referred to herein as HD1, and is represented in SEQ ID No. 1 (nucleotide) and SEQ ID No. 2 (amino acid).

A search of expressed sequence tag (EST) libraries turned up partial sequences for human HDx transcripts, and revealed the existence of at least two other human HDx genes related to HD1, these other paralogs referred to herein as HD2 and HD3. Nucleotide and amino acid sequences for partial clones of other human HDx homologs are provided by SEQ ID Nos. 2-4 and 6-8, respectively.

Analysis of the HDx sequences indicated no obvious similarities with any previously identified domains or motifs. However, the fact that each full-length clone lacks a signal sequence, along with the observation that proteins cans be detected in the nucleus, indicates that the HDx genes encode intracellular proteins.

Careful inspection of the HDx clones suggests at least two novel motifs, one or both of which may be characteristic of at least subfamilies of the mammalian HDx family. The first apparently conserved structural element of the HDx family occurs in the N-terminal portion of the molecule, and is designated herein as the "v motif". With reference to human HD1, the v motif corresponds to amino acid residues Asp130-Phe198. By alignment of the human HDx sequences, the element is represented by the consensus sequence:

(SEQ ID No. 12)
DXXNXGGLHHAKKXEASGFCYXNDIVXXIXELLXYHXRVXYIDXDXHHGD

GXEAFY-XTDRVMTXSF, more preferably by the consensus sequence:

(SEQ ID No. 13)
DIAX$_1$NWAGGLHHAKKX$_2$EASGFCYVNDIVX$_3$X$_4$ILELLKYHX$_5$RVLYID

IDIHHGDGX$_6$E-AFYX$_7$TDRVMTVSF wherein each of X$_n$ represents any single amino acid, though more preferably represents an amino acid residue in the corresponding human HDx sequences of the appended sequence listing.

A second motif, herein designated by the χ motif is represented by the consensus sequence:

(SEQ ID No. 14)
CVXXXKXFXXPXXXXGGGGYTXRNVARXWXXET more preferably by the consensus sequence:

(SEQ ID No. 15)
CVEX$_8$VKX$_9$FNX$_{10}$PLLX$_{11}$LGGGGYTX$_{12}$RNVARCWTYET wherein each of X$_n$ represents any single amino acid, though more preferably represents an amino acid residue in the corresponding human HDx sequences of the appended sequence listing. The χ motif can be found in the human HD1 sequence at C284-Thr316.

The family of HDx proteins apparently ranges in size from about 40 kd to about 60 kd for the unmodified polypeptide chain. For instance, the bovine HD1 protein migrates on an SDS-PAGE (9%) gel with an apparent molecular weight of 46 kD. The human HD1 amino acid sequence predicts a molecular weight for the polypeptide chain of 55 kD.

Accordingly, certain aspects of the present invention relate to nucleic acids encoding HDx proteins, the HDx proteins themselves, antibodies immunoreactive with HDx proteins, and preparations of such compositions. Moreover, the present invention provides diagnostic and therapeutic assays and reagents for detecting and treating disorders involving, for example, aberrant expression (or loss thereof) of HDx homologs. In addition, drug discovery assays are provided for identifying agents which can modulate the biological function of HDx proteins, such as by altering the binding of HDx molecules to either proteins or nucleic acids. Such agents can be useful therapeutically to alter the growth and/or differentiation of a cell.

Other aspects of the invention are described below or will be apparent to those skilled in the art in light of the present disclosure.

Analysis of the human HDx sequences, while not revealing any obvious similarities to known domains or motifs, did indicate similarities with previously identified proteins from both *Saccharomyces cerevisiae* and *Xenopus laevis*. Those genes, RPD3 (SEQ ID No. 9) and Xe-RPD3 (SEQ ID No. 10), respectively, had not previously been ascribed any specific function. However, based on our observations for the function of HD1, it is now apparent that each of these other proteins are also deacetylases, and represent potential therapeutic targets. Accordingly, drug discovery assays are provided for identifying agents which can modulate the biological function of "HDx-related" proteins, such as RPD3 homologs, by altering the enzymatic activity of the deacetylase, or its binding to other cellular components including homologs of RbAp48 (described infra). Such agents can be useful therapeutically to alter the growth and/or differentiation of non-human cells, such as in the treatment of mycotic infections, or as additives to livestock feed, e.g., to promote weight gain, or as topical antiseptics for sterilizing medical equipment.

In addition we isolated another bovine protein having an approximate molecular size of 50 kD which apparently binds HDx proteins isolated by the trapoxin matrix, and microsequencing of that protein demonstrated that it was related to the protein referred to in the art as RbAp48 (Qian et al. (1993) *Nature* 364:648; SEQ ID No. 11). RbAp48 was originally identified as a protein that binds to the retinoblastoma (Rb) gene product. The retinoblastoma (RB) gene product plays a role in tumor suppression (Weinberg, R. A., (September 1988) *Scientific Amer.* pp 44-51; Hansen et al. (1988) *Trends Genet.* 4:125-128). The role of RB as a tumor-suppressor protein in cell-cycle control is believed to be similar to that of another tumor-suppressor, p53 (Green (1989) *Cell* 56:1-3; Mowat et al (1985 *Nature* 314:633-636). Inactivation or mutation of the second RB allele in one of the somatic cells of these susceptible individuals appears to be the molecular event that leads to tumor formation (Caveneee et al. (1983) *Nature* 305:799-784; Friend et al. (1987) *PNAS* 84:9059-9063).

The growth suppression function of the retinoblastoma protein is thought to be mediated by Rb binding to cellular proteins. RbAp48 is one of the major proteins that binds to a putative functional domain at the carboxy terminus of the Rb protein. Complex formation between RbAp48 and Rb occurs in vitro and in vivo, and apparently involves direct interaction between the proteins. Like Rb, RbAp48 is a ubiquitously expressed nuclear protein. RbAp48 share sequence homology with MS11, a negative regulator of the Ras-cyclic AMP pathway in the yeast *Saccharomyces cerevisiae*. Furthermore, like MS11, human RbAp48 suppresses the heat-shock sensitivity of the yeast iral strains and RAS2Val19 strains. Interaction with RbAp48 may be one of the mechanisms for suppression of growth mediated by Rb. Accordingly, the interaction of RbAp48 with HDx proteins further implicates the HDx proteins in cell-cycle regulation.

The RpAp48 interaction with HDx and HDx-related proteins represents yet another therapeutic target. Accordingly, drug discovery assays are provided for identifying agents which can modulate the interaction of RbAp48 proteins and the like with HDx-related proteins. Such assays can be derived to detect the ability of a test agent to alter protein-protein contacts, or to alter the enzymatic activity of the deacetylase in complexes including an RbAp48 protein (e.g., were such complexes allosterically modulate the HDx enzymatic activity). As above, such agents can be useful therapeutically to alter the growth and/or differentiation of cells.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding one of the HDx polypeptides of the present invention, including both exon and (optionally) intron sequences. A "recombinant gene" refers to nucleic acid encoding an HDx polypeptide and comprising HDx-encoding exon sequences, though it may optionally include intron sequences which are either derived from a chromosomal HDx gene or from an unrelated chromosomal gene. Exemplary recombinant genes encoding the subject HDx polypeptide are represented in the appended Sequence Listing. The term "intron" refers to a DNA sequence present in a given HDx gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an HDx polypeptide or, where anti-sense expression occurs from the transferred gene, the expression of a naturally-occurring form of the HDx protein is disrupted.

As used herein, the term "specifically hybridizes" refers to the ability of the probe/primer of the invention to hybridize to at least 15 consecutive nucleotides of an HDx gene, such as an HDx sequence designated in one of SEQ ID Nos: 1-4, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than an HDx protein, as defined herein. In preferred embodiments, the oligonucleotide probe specifically detects only one of the subject HDx paralogs, e.g., does not substantially hybridize to transcripts for other HDx homologs in the same species.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant HDx genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of HDx genes.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of hepatic, pancreatic, neuronal or hematopoietic origin. The term also covers so-called "leaky" promoters, which regulate expression of a selected DNA primarily in one tissue, but can cause at least low level expression in other tissues as well.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the HDx proteins, e.g. either agonistic or antagonistic forms. However, transgenic animals in which the recombinant HDx gene is silent are also contemplated, as for example, the FLP or CRE recombinase dependent constructs described below. Moreover, "transgenic animal" also includes those recombinant animals in which gene disruption of one or more HDx genes is caused by human intervention, including both recombination and antisense techniques.

The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The invention also contemplates transgenic insects, including those of the genus *Drosophila*, such as *D. melanogaster*. The term "chimeric animal" is used herein to refer to animals in which the recombinant gene is found, or in which the recombinant is expressed in some but not all cells of the animal. The term "tissue-specific chimeric animal" indicates that one of the recombinant HDx genes is present and/or expressed or disrupted in some tissues but not others.

As used herein, the term "transgene" means a nucleic acid sequence (encoding, e.g., one of the HDx polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an HDx polypeptide" may thus refer to one or more genes within a particular individual. Moreover, certain differences in nucleotide sequences may exist between individuals of the same species, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with one of the HDx sequences of the present invention.

As used herein, an "HDx-related" protein refers to the HDx proteins described herein, and other human homologs of those HDx sequences, as well as orthologs and paralogs (homologs) of the HDx proteins in other species, ranging from yeast to other mammals, e.g., homologous histone deacetylase, The term "ortholog" refers to genes or proteins which are homologs via speciation, e.g., closely related and assumed to have common descent based, on structural and functional considerations. Orthologous proteins function as recognizably the same activity in different species. The term "paralog" refers to genes or proteins which are homologs via gene duplication, e.g., duplicated variants of a gene within a genome. See also, Fritch, W M (1970) *Syst Zool* 19:99-113.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject HDx polypeptides with a second amino acid sequence defining a domain (e.g. polypeptide portion) foreign to and not substantially homologous with any domain of one of the HDx proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-HDx-Y, wherein HDx represents a portion of the protein which is derived from one of the HDx proteins, and X and Y are, independently, absent or represent amino acid sequences which are not related to one of the HDx sequences in an organism.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject HDx polypeptides preferably includes no more than 10 kilobases (kb) of nucleic acid sequence which naturally immediately flanks the HDx gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to isolated nucleic acids comprising nucleotide sequences encoding HDx polypeptides, and/or equivalents of such nucleic acids. The term nucleic acid as used herein is intended to include fragments as equivalents. The term equivalent is understood to include nucleotide sequences encoding functionally equivalent HDx polypeptides or functionally equivalent peptides having an activity of an HDx protein such as described herein. Equivalent nucleotide sequences will include sequences that differ by one or more nucleotide substitutions, additions or deletions, such as allelic variants; and will, therefore, include sequences that differ from the nucleotide sequence of the HDx cDNA sequences shown in any of SEQ ID Nos:1-4 due to the degeneracy of the genetic code. Equivalents will also include nucleotide sequences that hybridize under stringent conditions (i.e., equivalent to about 20-27° C. below the melting temperature ($T_m$) of the DNA duplex formed in about 1M salt) to the nucleotide sequences represented in one or more of SEQ ID Nos:1-4. In one embodiment, equivalents will further include nucleic acid sequences derived from and evolutionarily related to, a nucleotide sequences shown in any of SEQ ID Nos:1-4.

Moreover, it will be generally appreciated that, under certain circumstances, it may be advantageous to provide homologs of one of the subject HDx polypeptides which function in a limited capacity as one of either an HDx agonist (mimetic) or an HDx antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of HDx proteins.

Homologs of each of the subject HDx proteins can be generated by mutagenesis, such as by discrete point mutation(s), or by truncation. For instance, mutation can give rise to homologs which retain substantially the same, or merely a subset, of the biological activity of the HDx polypeptide from which it was derived. Alternatively, antagonistic forms of the protein can be generated which are able to inhibit the function of the naturally occurring form of the protein, such as by competitively binding to an HDx substrate or HDx associated protein, as for example competing with wild-type HDx in the binding of RbAp48 or a histone. In addition, agonistic forms of the protein may be generated which are constitutively active, or have an altered $K_{cat}$ or $K_m$ for deacetylation reactions. Thus, the HDx protein and homologs thereof provided by the subject invention may be either positive or negative regulators of transcription and/or replication.

In general, polypeptides referred to herein as having an activity of an HDx protein (e.g., are "bioactive") are defined as polypeptides which include an amino acid sequence corresponding (e.g., identical or homologous) to all or a portion of the amino acid sequences of an HDx proteins shown in any one or more of SEQ ID Nos:5-8 and which mimic or antagonize all or a portion of the biological/biochemical activities of a naturally occurring HDx protein. Examples of such biological activity include the ability to modulate proliferation of cells. For example, inhibiting histone deacetylation causes cells to arrest in G1 and G2 phases of the cell cycle. The biochemical activity associated with HDx proteins of the present invention can also characterized in terms of binding to and (optionally) catalyzing the deacetylation of an acetylated histone. Another biochemical property of certain of the subject HDx proteins involves binding to other cellular proteins, such, as RbAp48.

Other biological activities of the subject HDx proteins are described herein or will be reasonably apparent to those skilled in the art. According to the present invention, a polypeptide has biological activity if it is a specific agonist or antagonist of a naturally-occurring form of an HDx protein.

Preferred nucleic acids encode an HDx polypeptide comprising an amino acid sequence at least 80% homologous, more preferably at least 85% homologous and most preferably at least 88% homologous with an amino acid sequence of a human HDx, e.g., such as selected from the group consisting of SEQ ID Nos: 5-8. Nucleic acids which encode polypeptides at least about 90%, more preferably at least about 95%, and most preferably at least about 98-99% homology with an amino acid sequence represented in one of SEQ ID Nos:5-8 are of course also within the scope of the invention, as are nucleic acids identical in sequence with any of the enumerated HDx sequences of the sequence listing. In one embodiment, the nucleic acid is a cDNA encoding a polypeptide having at least one activity of the subject HDx polypeptide.

In certain preferred embodiments, the invention features a purified or recombinant HDx polypeptide having peptide chain with a molecular weight in the range of 40 kd to 60 kd, even more preferably in the range of 45-50 kd or 53-58 kd. It will be understood that certain post-translational modifications, e.g., phosphorylation and the like, can increase the apparent molecular weight of the HDx protein relative to the unmodified polypeptide chain, and cleavage of certain sequences, such as pro-sequences, can likewise decrease the apparent molecular weight.

In other preferred embodiments, the nucleic acid encodes an HDx polypeptide which includes both the ν and χ motifs, and preferably possess a histone deacetylase activity. For example, preferred HDx proteins are represented by the general formula A-(ν motif)-B-(χ motif)-C, wherein the ν motif is an amino acid sequence represented in SEQ ID No. 12, more preferably SEQ ID No. 13, the χ motif is an amino acid sequence represented in SEQ ID No. 14, more preferably SEQ ID No. 15, and A, B and C represent amino acid sequences which are correspond to HDx or HDx-related proteins.

Still other preferred nucleic acids of the present invention encode an HDx polypeptide which includes a polypeptide sequence corresponding to all or a portion of amino acid residues of any one of SEQ ID Nos: 5-8, e.g., at least 5, 10, 25, 50 or 100 amino acid residues of that region.

Another aspect of the invention provides a nucleic acid which hybridizes under high or low stringency conditions to the nucleic acid represented by SEQ ID No: 1. Appropriate stringency conditions which promote DNA hybridization, for example, 6.0+ sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequences shown in one of SEQ ID Nos: 1-4 due to degeneracy in the genetic code are also within the scope of the invention. Such nucleic acids encode functionally equivalent peptides (i.e., a peptide having a biological activity of an HDx polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an HDx polypeptide. However, it is expected that DNA sequence polymorphisms that do lead to changes in the amino acid sequences of the subject HDx polypeptides will exist among, for example, humans. One skilled in the art will appreciate that these variations in one or more nucleotides (up to about 3-5% of the nucleotides) of the nucleic acids encoding polypeptides having an activity of an HDx polypeptide may exist among individuals of a given species due to natural allelic variation.

As used herein, an HDx gene fragment refers to a nucleic acid having fewer nucleotides than the nucleotide sequence encoding the entire mature form of an HDx protein yet which (preferably) encodes a polypeptide which retains some biological activity of the full length protein. Fragment sizes contemplated by the present invention include, for example, 5, 10, 25, 50, 75, 100, or 200 amino acids in length.

As indicated by the examples set out below, HDx protein-encoding nucleic acids can be obtained from mRNA present in any of a number of eukaryotic cells. It should also be possible to obtain nucleic acids encoding HDx polypeptides of the present invention from genomic DNA from both adults and embryos. For example, a gene encoding an HDx protein can be cloned from either a cDNA or a genomic library in accordance with protocols described herein, as well as those generally known to persons skilled in the art. A cDNA encoding an HDx protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding an HDx protein can also be cloned using established polymerase chain reaction techniques in accordance with the nucleotide sequence information provided by the invention. The nucleic acid of the invention can be DNA or RNA. A preferred nucleic acid is a cDNA including a nucleotide sequence represented by one of SEQ ID Nos: 1-4.

Another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding one or more of the subject HDx proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an HDx protein. Alternatively, the antisense construct is an oligonucleotide probe which is generated ex vivo and which, when introduced into the cell causes inhibition of expression by hybridizing with the mRNA and/or genomic sequences of an HDx gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775), or peptide nucleic acids (PNAs). Additionally, general approaches to constructing oligomers useful in antisense therapy have been reviewed, for example, by Van der Krol et al. (1988) Biotechniques 6:958-976; and Stein et al. (1988) Cancer Res 48:2659-2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of routes of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of one of the HDx proteins, can be used in the manipulation of tissue, e.g. tissue differentiation or growth, both in vivo and ex vivo.

Furthermore, the anti-sense techniques (e.g. microinjection of antisense molecules, or transfection with plasmids whose transcripts are anti-sense with regard to an HDx mRNA or gene sequence) can be used to investigate role of HDx in developmental events, as well as the normal cellular function of HDx in adult tissue. Such techniques can be utilized in cell culture, but can also be used in the creation of transgenic animals (described infra).

This invention also provides expression vectors containing a nucleic acid encoding an HDx polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject HDx proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding HDx polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a peptide having an agonistic activity of a subject HDx polypeptide, or alternatively, encoding a peptide which is an antagonistic form of the HDx protein, such as a catalytically-inactive deacetylase. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids, e.g., encoding either an agonistic or antagonistic form of one of the subject HDx proteins or an antisense molecule described above. Thus, another aspect of the invention features expression vectors for in vivo or in vitro transfection and expression of an HDx polypeptide or antisense molecule in particular cell types so as to reconstitute the function of, or alternatively, abrogate the function of HDx-induced transcription in a tissue in which the naturally-occurring form of the protein is misexpressed; or to deliver a form of the protein which alters differentiation of tissue, or which inhibits neoplastic transformation.

Expression constructs of the subject HDx polypeptides, as well as antisense constructs, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of HDx expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA encoding the particular HDx polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Retrovirus vectors, adenovirus vectors and adeno-associated virus vectors are exemplary recombinant gene delivery system for the transfer of exogenous genes in vivo, particularly into humans. These vectors provide efficient delivery of genes into cells, and the transferred nucleic acids are stably integrated into the chromosomal DNA of the host.

In addition to viral transfer methods, such as those illustrated above, non-viral methods can also be employed to cause expression of a subject HDx polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject HDx polypeptide gene by the targeted cell. Exemplary gene delivery systems of this type include liposomal derived systems, poly-lysine conjugates, and artificial viral envelopes.

In clinical settings, the gene delivery systems for the therapeutic HDx gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057). AN HDx gene, such as any one of the clones represented in the group consisting of SEQ ID NO:1-4, can be delivered in a gene therapy construct by electroporation using techniques described, for example, by Dev et al. ((1994) Cancer Treat Rev 20:105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery, system.

Another aspect of the present invention concerns recombinant forms of the HDx proteins. Recombinant polypeptides preferred by the present invention, in addition to native HDx proteins, are at least 80% homologous, more preferably at least 85% homologous and most preferably at least 88% homologous with an amino acid sequence represented by any of SEQ ID Nos: 5-8. Polypeptides which possess an activity of an HDx protein (i.e. either agonistic or antagonistic), and which are at least 90%, more preferably at least 95%, and most preferably at least about 98-99% homologous with a sequence selected from the group consisting of SEQ ID Nos: 5-8 are also within the scope of the invention. In other preferred embodiments, the HDx polypeptide includes both the v and χ motifs, and preferably possess a histone deacetylase activity.

The term "recombinant HDx protein" refers to a polypeptide which is produced by recombinant DNA techniques, wherein generally, DNA encoding an HDx polypeptide is inserted into a suitable expression vector which is in turn used to transform a host cell to produce the heterologous protein. Moreover, the phrase "derived from", with respect to a recombinant HDx gene, is meant to include within the meaning of "recombinant protein" those proteins having an amino acid sequence of a native HDx protein, or an amino acid sequence similar thereto which is generated by mutations including substitutions and deletions (including truncation) of a naturally occurring form of the protein.

The present invention further pertains to recombinant forms of the subject HDx polypeptides which are encoded by genes derived from a mammal (e.g. a human), and which have amino acid sequences evolutionarily related to the HDx proteins represented in SEQ ID Nos: 5-8. Such recombinant HDx polypeptides preferably are capable of functioning in one of either role of an agonist or antagonist of at least one biological activity of a wild-type ("authentic") HDx protein of the appended sequence listing. The term "evolutionarily related to", with respect to amino acid sequences of HDx proteins, refers to both polypeptides having amino acid sequences which have arisen naturally, and also to mutational variants of HDx polypeptides which are derived, for example, by combinatorial mutagenesis.

The present invention also provides methods of producing the subject HDx polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant HDx polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant HDx polypeptide is a fusion protein containing a domain which facilitates its purification, such as GST fusion protein or poly(His) fusion protein.

This invention also pertains to a host cell transfected to express recombinant forms of the subject HDx polypeptides. The host cell may be any prokaryotic or eukaryotic cell. Thus, a nucleotide sequence derived from the cloning of HDx proteins, encoding all or a selected portion of a full-length protein, can be used to produce a recombinant form of an HDx polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinases, p53, WT1, PTP phosphatases, SRC, and the like. Similar procedures, or modifications thereof, can be employed to prepare recombinant HDx polypeptides by microbial means or tissue-culture technology in accord with the subject invention.

The recombinant HDx genes can be produced by ligating nucleic acid encoding an HDx protein, or a portion thereof, into a vector suitable for expression in either prokaryotic cells, eukaryotic cells, or both. Expression vectors for production of recombinant forms of the subject HDx polypeptides include plasmids and other vectors. For instance, suitable vectors for the expression of an HDx polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an HDx polypeptide is produced recombinantly utilizing an expression vector generated by sub-cloning the coding sequence of one of the HDx genes represented in SEQ ID Nos:1-4.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant HDx polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an HDx protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751-757) and Salmonella typhimurium and its in vitro activity has been demonstrated on recombinant proteins (Miller et al. (1987) PNAS 84:2718-1722). Therefore, removal of an N-terminal methionine, if desired, can be achieved either in vivo by expressing HDx-derived polypeptides in a host which produces MAP (e.g., E. coli or CM89 or S. cerevisiae), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of an HDx protein. For example, the VP6 capsid protein of rotavirus can be used as an immunologic carrier protein for portions of the HDx polypeptide, either in the monomeric form or in the form of a viral particle. The nucleic acid sequences corresponding to the portion of a subject HDx protein to which antibodies are to be raised can be incorporated into a fusion gene construct which includes coding sequences for a late vaccinia virus structural protein to produce a set of recombinant viruses expressing fusion proteins comprising HDx epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an HDx protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of an HDx polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of HDx proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the HDx polypeptides of the present invention. For example, HDx polypeptides can be generated as glutathione-5-transferase (GST-fusion) proteins. Such GST-fusion proteins can enable easy purification of the HDx polypeptide; as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

HDx polypeptides may also be chemically modified to create HDx derivatives by forming covalent or aggregate conjugates with other chemical moieties, such as glycosyl groups, lipids, phosphate, acetyl groups and the like. Covalent derivatives of HDx proteins can be prepared by linking the chemical moieties to functional groups on amino acid sidechains of the protein or at the N-terminus or at the C-terminus of the polypeptide.

The present invention also makes available isolated HDx polypeptides which are isolated from, or otherwise substantially free of other cellular proteins, especially other signal transduction factors and/or transcription factors which may normally be associated with the HDx polypeptide. The term "substantially free of other cellular proteins" (also referred to herein as "contaminating proteins") or "substantially pure or purified preparations" are defined as encompassing preparations of HDx polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified HDx preparations will lack any contaminating proteins from the same animal from that HDx is normally produced, as can be accomplished by recombinant expression of, for example, a human HDx protein in a non-human cell.

As described above for recombinant polypeptides, isolated HDx polypeptides can include all or a portion of an amino acid sequences corresponding to an HDx polypeptide represented in any one of SEQ ID Nos: 5-8 or homologous sequences thereto. In preferred embodiments, the HDx polypeptide includes both the ν and χ motifs, and preferably possess a histone deacetylase activity.

Isolated peptidyl portions of HDx proteins can be obtained by screening peptides, recombinantly produced from the corresponding fragment of the nucleic acid encoding such, peptides. In addition, fragments can be chemically synthesized using techniques known the art such as conventional Merrifield solid phase f-Moc or t-Boc chemistry. For example, an HDx polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") HDx protein.

The recombinant HDx polypeptides of the present invention also include homologs of the authentic HDx proteins, such as versions of those protein which are resistant to proteolytic cleavage, as for example, due to mutations which alter ubiquitination or other enzymatic targeting associated with the protein.

Modification of the structure of the subject HDx polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the HDx polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981). Whether a change in the amino acid sequence of a peptide results in a functional HDx homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject HDx proteins as well as truncation mutants, and is especially useful for identifying potential variant sequences (e.g. homologs) that are functional in modulating histone deacetylation. The purpose of screening such combinatorial libraries is to generate, for example, novel HDx homologs which can act as either agonists or antagonist, or alternatively, possess novel activities all together. To illustrate, HDx homologs can be engineered by the present method to provide selective, constitutive activation of enzymatic activity. Thus, combinatorially-derived homologs can be generated to have an increased potency relative to a naturally occurring form of the protein.

Likewise, HDx homologs can be generated by the present combinatorial approach to selectively inhibit (antagonize) histone deacetylation. For instance, mutagenesis can provide HDx homologs which are able to bind other regulatory proteins or cytoskeletal elements (or DNA) yet prevent acetylation of histones, e.g. the homologs can be dominant negative mutants. In a preferred embodiment, a dominant negative mutant of an HDx protein is mutated at one or more residues of its catalytic site and/or specificity subsites.

In one aspect of this method, the amino acid sequences for a population of HDx homologs or other related proteins are aligned, preferably to promote the highest homology possible. Such a population of variants can include, for example, HDx homologs from one or more species. Amino acids which appear at each position of the aligned sequences are selected to create a degenerate set of combinatorial sequences. In a preferred embodiment, the variegated library of HDx variants is generated by combinatorial mutagenesis at the nucleic acid level, and is encoded by a variegated gene library. For instance, a mixture of synthetic oligonucleotides can be enzymatically ligated into gene sequences such that the degenerate set of potential HDx sequences are expressible as individual polypeptides, or alternatively, as a set of larger fusion proteins (e.g. for phage display) containing the set of HDx sequences therein.

As illustrated in FIG. 5B, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. For instance, FIG. 5B includes the alignment of the ν and χ-motifs for several of the HDx gene products. Analysis of the alignment of these sequences from the HDx clones can give rise to the generation of a degenerate library of polypeptides comprising potential HDx sequences. In an exemplary embodiment, a library of variants based on the HD1 sequence, but degenerate across each of the ν and χ-motifs can be provided. On such library can be represented by the general formula A-(ν-motif)-B-(χ motif)-C, wherein the ν motif is an amino acid sequence represented in the general formula

DIAX$_1$NWAGGLHHAKKX$_2$EASGFCYVNDIVX$_3$X$_4$ILELLKYHX$_5$RVLYID

IDIHHGDGX$_6$E-AFYX$_7$TDRVMTVSF the χ motif is an amino acid sequence represented in the general formula

CVEX$_8$VKX$_9$FNX$_{10}$PLLX$_{11}$LGGGGYTX$_{12}$RNVARCWTYET

A corresponds to Met1-Thr129 of SEQ ID No. 5, B corresponds to His199-Lys283 of SEQ ID No. 5, and C corresponds to Ala317-Ala482 of SEQ ID No. 5, wherein X$_i$ represents Ile or Val; X$_2$ represents Phe or Ser; X$_3$ represents Phe or Leu; X$_4$ represents Gly or Ala; X$_5$ represents Pro or Gln; X$_6$ represents Gln or Glu; X$_7$ represents Leu or Thr; X$_8$ represents Val or Tyr; X$_9$ represents Thr or Ser; X$_{10}$ represents Leu or Ile; X$_{11}$ represents Met or Val; and X$_{12}$ represents Ile or Val. To further expand the combinatorial set, other conservative mutations relative to those appearing in the human sequences can be provided. For example, in a more expansive library, X$_1$ represents Gly, Ala, Val, Be or Leu; X$_2$ represents Phe, Tyr, Thr or Ser; X$_3$ represents Phe, Tyr, Gly, Ala, Val, Be or Leu; X$_4$ represents Gly, Ala, Val, Ile or Leu; X$_5$ represents Pro, Asn or Gln; X$_6$ represents Asn, Gln, Asp or Glu; X$_7$ represents Gly, Ala, Val, Ile, Leu, Ser or Thr; X$_8$ represents Gly, Ala, Val, Ile, Leu, Phe or Tyr; X$_9$ represents Thr, Cys, or Ser; X$_{10}$ represents Gly, Ala, Val, Ile or Leu; X$_{11}$ represents Met, Cys, Gly, Ala, Val, Ile, Leu, Ser or Thr; and X$_{12}$ represents Gly, Ala, Val, Ile or Leu. In still another library, each degenerate position can be any one of the naturally occurring amino acids. Likewise, the ν and χ-motifs can correspond to the degenerate sequences designated by SEQ ID Nos. 12 and 14, respectively.

There are many ways by which such libraries of potential HDx homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential HDx sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for an HDx clone in order to generate a variegated population of HDx fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an HDx coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of HDx homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

In an exemplary embodiment, the library of HDx variants is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd., and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007-16010; Griffiths et al. (1993) EMBO J. 12:725-734; Clackson et al. (1991) Nature 352:624-628; and Barbas et al. (1992) PNAS 89:4457-4461).

For example, the recombinant phage antibody system (RPAS, Pharmacia Catalog number 27-9400-01) can be easily modified for use in expressing and screening HDx combinatorial libraries by panning on glutathione immobilized histones/GST fusion proteins or RbAp48/GST fusion protein to enrich for HDx homologs which retain an ability to bind a substrate or regulatory protein. Each of these HDx homologs can subsequently be screened for further biological activities in order to differentiate agonists and antagonists. For example, histone-binding homologs isolated from the combinatorial library can be tested for their enzymatic activity directly, or for their effect on cellular proliferation relative to the wild-type form of the protein.

The invention also provides for reduction of the HDx or RbAp48 or histones proteins to generate mimetics, e.g. peptide or non-peptide agents, which are able to disrupt a biological activity of an HDx polypeptide of the present invention, e.g. as catalytic inhibitor or an inhibitor of protein-protein interactions. Thus, such mutagenic techniques as described above are also useful to map the determinants of the HDx proteins which participate in protein-protein or protein-DNA interactions involved in, for example, interaction of the subject HDx polypeptide with histones, RbAp48 or cytoskeletal elements. To illustrate, the critical residues of a subject HDx polypeptide which are involved in molecular recognition of histones can be determined and used to generate HDx-derived peptidomimetics which competitively inhibit binding of the authentic HDx protein with that moiety. Likewise, residues of a histone or of RbAp48 involved in binding to HDx proteins can be identified, and peptides or peptidomimetics based on such residues can also be used as competitive inhibitors of the interaction of an HDx protein with either of those proteins. By employing, for example, scanning mutagenesis to map the amino acid residues of a protein which is involved in binding other proteins, peptidomimetic compounds can be generated which mimic those residues which facilitate the interaction. Such mimetics may then be used to interfere with the normal function of an HDx protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71).

Another aspect of the invention pertains to an antibody specifically reactive with an HDx protein. For example, by using immunogens derived from an HDx protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., an HDx polypeptide or an antigenic fragment which is capable of eliciting an antibody response). Techniques for conferring immunogenicity on a protein or peptide include conjugation to carriers or other techniques well known in the art. An immunogenic portion of an HDx protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an HDx protein of a organism, such as a mammal, e.g. antigenic determinants of a protein represented by one of SEQ ID Nos: 5-8 or closely related homologs (e.g. at least 85% homologous, preferably at least 90% homologous, and more preferably at least 95% homologous). In yet a further preferred embodiment of the present invention, in order to provide, for example, antibodies which are immuno-selective for discrete HDx homologs, e.g. HD1, the anti-HDx polypeptide antibodies do not substantially cross react (i.e. does not react specifically) with a protein which is, for example, less than 85%, 90% or 95% homologous with the selected HDx. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for the intended target HDx.

Following immunization of an animal with an antigenic preparation of an HDx polypeptide, anti-HDx antisera can be obtained and, if desired, polyclonal anti-HDx antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an HDx polypeptide of the present invention and monoclonal antibodies isolated from a culture comprising such hybridoma cells.

The term antibody as used herein is intended to include fragments thereof which are also specifically reactive with one of the subject HDx polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for an HDx protein conferred by at least one CDR region of the antibody.

Both monoclonal and polyclonal antibodies (Ab) directed against authentic HDx polypeptides, or HDx variants, and antibody fragments such as Fab, F(ab)$_2$, Fv and scFv can be used to block the action of one or more HDx proteins and allow the study of the role of these proteins in, for example, differentiation of tissue. Experiments of this nature can aid in deciphering the role of HDx proteins that may be involved in control of proliferation versus differentiation, e.g., in patterning and tissue formation.

Antibodies which specifically bind HDx epitopes can also be used in immunohistochemical staining of tissue samples in order to evaluate the abundance and pattern of expression of each of the subject HDx polypeptides. Anti-HDx antibodies can be used diagnostically in immuno-precipitation and immuno-blotting to detect and evaluate HDx protein levels in tissue as part of a clinical testing procedure. For instance, such measurements can be useful in predictive valuations of the onset or progression of proliferative or differentiative disorders. Likewise, the ability to monitor HDx protein levels in an individual can allow determination of the efficacy of a given treatment regimen for an individual afflicted with such a disorder. The level of HDx polypeptides may be measured from cells in bodily fluid, such as in samples of cerebral spinal fluid or amniotic fluid, or can be measured in tissue, such as produced by biopsy. Diagnostic assays using anti-HDx antibodies can include, for example, immunoassays designed to aid in early diagnosis of a disorder, particularly ones which are manifest at birth. Diagnostic assays using anti-HDx polypeptide antibodies can also include immunoassays designed to aid in early diagnosis and phenotyping neoplastic or hyperplastic disorders.

Another application of anti-HDx antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an HDx protein, e.g. other orthologs of a particular HDx protein or other paralogs from the same species, can then be detected with antibodies, as, for example, reacting nitrocellulose filters lifted from infected plates with anti-HDx antibodies. Positive phage detected by this assay can then be isolated from the infected plate. Thus, the presence of HDx homologs can be detected and cloned from other animals, as can alternate isoforms (including splicing variants) from humans.

Moreover, the nucleotide sequences determined from the cloning of HDx genes from organisms will further allow for the generation of probes and primers designed for use in identifying and/or cloning HDx homologs in other cell types, e.g. from other tissues, as well as HDx homologs from other organisms. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence selected from the group consisting of SEQ ID Nos: 1-4 or naturally occurring mutants thereof. For instance, primers based on the nucleic acid represented in SEQ ID Nos: 1-4 can be used in PCR reactions to clone HDx homologs. Likewise, probes based on the subject HDx sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme cofactors.

Such probes can also be used as a part of a diagnostic test kit for identifying cells or tissue which misexpress an HDx protein, such as by measuring a level of an HDx-encoding nucleic acid in a sample of cells from a patient; e.g. detecting HDx mRNA levels or determining whether a genomic HDx gene has been mutated or deleted.

To illustrate, nucleotide probes can be generated from the subject HDx genes which facilitate histological screening of intact tissue and tissue samples for the presence (or absence) of HDx-encoding transcripts. Similar to the diagnostic uses of anti-HDx antibodies, the use of probes directed to HDx messages, or to genomic HDx sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of an HDx protein. For instance, variation in polypeptide synthesis can be differentiated from a mutation in a coding sequence.

Accordingly, the present method provides a method for determining if a subject is at risk for a disorder characterized by aberrant cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding an HDx-protein, or (ii) the mis-expression of the HDx gene. To illustrate, such genetic lesions can be detected by ascertaining the existence of at least one of (i) a deletion of one or more nucleotides from an HDx gene, (ii) an addition of one or more nucleotides to an HDx gene, (iii) a substitution of one or more nucleotides of an HDx gene, (iv) a gross chromosomal rearrangement of an HDx gene, (v) a gross alteration in the level of a messenger RNA transcript of an HDx gene, (vii) aberrant modification of an HDx gene, such as of the methylation pattern of the genomic DNA, (vii) the presence of a non-wild type splicing pattern of a messenger RNA transcript of an HDx gene, (viii) a non-wild type level of an HDx-protein, and (ix) inappropriate post-translational modification of an HDx-protein. As set out below, the present invention provides a large number of assay techniques for detecting lesions in an HDx gene, and importantly, provides the ability to discern between different molecular causes underlying HDx-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of an HDx gene, such as represented by any of SEQ ID Nos: 1-4, or naturally occurring mutants thereof, or 5' or 3' flanking sequences or intronic sequences naturally associated with the subject. HDx genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1944) PNAS 91:360-364), the later of which can be particularly useful for detecting point mutations in the HDx gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an HDx gene under conditions such that hybridization and amplification of the HDx gene (if present) occurs, and (iv) detecting the presence or absence of an amplification product, or detecting the size of the amplification product and comparing the length to a control sample.

In still another embodiment, the level of an HDx-protein can be detected by immunoassay. For instance, the cells of a biopsy sample can be lysed, and the level of an HDx-protein present in the cell can be quantitated by standard immunoassay techniques. In yet another exemplary embodiment, aberrant methylation patterns of an HDx gene can be detected by digesting genomic DNA from a patient sample with one or more restriction endonucleases that are sensitive to methylation and for which recognition sites exist in the HDx gene (including in the flanking and intronic sequences). See, for example, Buiting et al. (1994) Human Mol Genet. 3:893-895. Digested DNA is separated by gel electrophoresis, and hybridized with probes derived from, for example, genomic or cDNA sequences. The methylation status of the HDx gene can be determined by comparison of the restriction pattern generated from the sample DNA with that for a standard of known methylation.

In yet another aspect of the invention, the subject HDx polypeptides can be used to generate a "two hybrid" assay or an "interaction trap" assay (see, for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; Iwabuchi et al. (1993) Oncogene 8:1693-1696; and Brent WO94/10300), for isolating coding sequences for other cellular proteins which bind HDxs ("HDx-binding proteins" or "HDx-bp"). Such HDx-binding proteins would likely be involved in the regulation of HDx, e.g., as regulatory subunits or transducers, or be substrates which are regulated by an HDx.

Briefly, the interaction trap relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for an HDx polypeptide. The second hybrid protein encodes a transcriptional activation domain fused in frame to a sample gene from a cDNA library. If the bait and sample hybrid proteins are able to interact, e.g., form an HDx-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the HDx and sample proteins.

Furthermore, by making available purified and recombinant HDx polypeptides, the present invention facilitates the development of assays which can be used to screen for drugs, including HDx homologs, which are either agonists or antagonists of the normal cellular function of the subject HDx polypeptides, or of their role in the pathogenesis of cellular differentiation and/or proliferation and disorders related thereto. Moreover, because we have also identified HDx-related proteins, such as the yeast RPD3 proteins, as histone deacetylases, the present invention further provides drug screening assays for detecting agents which modulate the bioactivity of HDx-related proteins. Such agents, when directed to, for example, fungal HDx-related proteins, can be used in the treatment of various infections. In a general sense, the assay evaluates the ability of a compound to modulate binding between an HDx polypeptide and a molecule, be it protein or DNA, that interacts with the HDx polypeptide. It will be apparent from the following description of exemplary assays that, in place of a human HDx protein, the assay can be derived with an HDx-related protein such as RPD3. Likewise, in place of human RbAp48, other HDx-binding proteins can be used, e.g., other human proteins. Exemplary compounds which can be screened include peptides, nucleic acids, carbohydrates, small organic molecules, and natural product extract libraries, such as isolated from animals, plants, fungus and/or microbes.

It is contemplated that any of the novel interactions described herein could be exploited in a drug screening assay. For example, in one embodiment, the interaction between an HDx protein and RbAp48 can be detected in the presence and the absence of a test compound. In another embodiment, the ability of a compound to modulate the binding of an HDx protein, or HDx-related protein such as the yeast RPD3, with histones can be assessed. The identification of a test compound which influences, for example, HD1 catalyzed deacetylation of histones would be useful in the modulation of HD1 activity in mammalian cells, while the identification of a test compound which selectively inhibits the yeast RPD3 deacetylase activity would be useful as an antifungal agent. In other embodiments the effect of a test compound on the binding of an HDx protein to other molecules, such as cytoskeletal components, or other proteins identified by the HDx-dependent ITS set out above, could be tested. A variety of assay formats will suffice and, in light of the present inventions, will be comprehended by a skilled artisan.

In a preferred embodiment, assays which employ the subject mammalian HDx proteins can be used to identify compounds that have therapeutic indexes more favorable than sodium butyrate, trapoxin, trichostatin or the like. For instance; trapoxin-like drugs can be identified by the present invention which have enhanced tissue-type or cell-type specificity relative to trapoxin. To illustrate, the subject assays can be used to generate compounds which preferentially inhibit IL-2 mediated proliferation/activation of lymphocytes, or inhibit proliferation of certain tumor cells, without substantially interfering with other tissues, e.g. hepatocytes. Likewise, similar assays can be used to identify drugs which inhibit proliferation of yeast cells or other lower eukaryotes, but which have a substantially reduced effect on mammalian cells, thereby improving therapeutic index of the drug as an anti-mycotic agent.

In one embodiment, the identification of such compounds is made possible by the use of differential screening assays which detect and compare drug-mediated inhibition of deacetylase activity between two or more different HDx-like enzymes, or compare drug-mediated inhibition of formation of complexes involving two or more different types of HDx-like proteins. To illustrate, the assay can be designed for side-by-side comparison of the effect of a test compound on the deacetylase activity or protein interactions of tissue-type specific HDx proteins. Given the apparent diversity of HDx proteins, it is probable that different functional HDx activities, or HDx complexes exist and, in certain instances, are localized to particular tissue or cell types. Thus, test compounds can be screened for agents able to inhibit the tissue-specific formation of only a subset of the possible repertoire of HDx/regulatory protein complexes, or which preferentially inhibit certain HDx enzymes. In an exemplary embodiment, an interaction trap assay can be derived using two or more different human HDx "bait" proteins, while the "fish" protein is constant in each, e.g. a human RbAp48 construct. Running the interaction trap side-by-side permits the detection of agents, which have a greater effect (e.g. statistically significant) on the formation of one of the HDx/RbAp48 complexes than on the formation of the other HDx complexes.

In similar fashion, differential screening assays can be used to exploit the difference in protein interactions and/or catalytic mechanism of mammalian HDx proteins and yeast RPD3 proteins in order to identify agents which display a statistically significant increase in specificity for inhibiting the yeast enzyme relative to the mammalian enzyme. Thus, lead compounds which act specifically on pathogens, such as fungus involved in mycotic infections, can be developed. By way of illustration, the present assays can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise comparing the relative effectiveness of a test compound on inhibiting the deacetylase activity of a mammalian HDx protein with its effectiveness towards inhibiting the deacetylase activity of an RPD3 homolog cloned from yeast selected from the group consisting of *Candida albicans, Candida stellatoidea, Candida tropicalis, Candida parapsilosis, Candida krusei, Candida pseudotropicalis, Candida quillermondii*, or *Candida rugosa*. Likewise, the present assay can be used to identify anti-fungal agents which may have therapeutic value in the treatment of aspergillosis by selectively targeting RPD3 homologs cloned from yeast such as *Aspergillus fumigatus, Aspergillus flavus, Aspergillus niger, Aspergillus nidulans*, or *Aspergillus terreus*. Where the mycotic infection is mucormycosis, the RPD3 deacetylase can be derived from yeast such as *Rhizopus arrhizus, Rhizopus oryzae, Absidia corymbifera, Absidia ramosa*, or *Mucor pusillus*. Sources of other RPD3 activities for comparison with a mammalian HDx activity includes the pathogen *Pneumocystis carinii*.

In addition to such HDx therapeutic uses, anti-fungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms.

In similar fashion, side by side comparison of inhibition of a mammalian HDx proteins and an insect HDx-related proteins, will permit selection of HDx inhibitors which discriminate between the human/mammalian and insect enzymes. Accordingly, the present invention expressly contemplates the use and formulations of the subject HDx therapeutics in insecticides, such as for use in management of insects like the fruit fly.

In yet another embodiment, certain of the subject HDx inhibitors can be selected on the basis of inhibitory specificity for plant HDx-related activities relative to the mammalian enzyme. For example, a plant HDx-related protein can be disposed in a differential screen with one or more of the human enzymes to select those compounds of greatest selectivity for inhibiting the plant enzyme. Thus, the present invention specifically contemplates formulations of the subject HDx inhibitors for agricultural applications, such as in the form of a defoliant or the like.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, a reaction mixture is generated to include an HDx polypeptide, compound(s) of interest, and a "target polypeptide", e.g., a protein, which interacts with the HDx polypeptide, whether as a substrate or by some other protein-protein interaction. Exemplary target polypeptides include histones and RbAp48 polypeptides. Detection and quantification of complexes containing the HDx protein provide a means for determining a compound's efficacy at inhibiting (or potentiating) complex formation between the HDx and the target polypeptide. The efficacy of the Compound can be assessed by generating dose response curves from data obtained using various concentrations of the test compound. Moreover, a control assay can also be performed to provide a baseline for comparison. In the control assay, isolated and purified HDx polypeptide is added to a composition containing the target polypeptide and the formation of a complex is quantitated in the absence of the test compound.

Complex formation between the HDx polypeptide and the target polypeptide may be detected by a variety of techniques. Modulation of the formation of complexes can be quantitated using, for example, detectably labeled proteins such as radiolabeled, fluorescently labeled, or enzymatically labeled HDx polypeptides, by immunoassay, by chromatographic detection, or by detecting the intrinsic activity of the acetylase.

Typically, it will be desirable to immobilize either HDx or the target polypeptide to facilitate separation of complexes from uncomplexed forms of one or both of the proteins, as well as to accommodate automation of the assay. Binding of HDx to the target polypeptide, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/HDx (GST/HDx) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of HDx-binding protein found in the bead fraction quantitated from the gel using standard electrophoretic techniques such as described in the appended examples.

Other techniques for immobilizing proteins on matrices are also available for use in the subject assay. For instance, either HDx or target polypeptide can be immobilized utilizing conjugation of biotin and streptavidin. For instance, biotinylated HDx molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with HDx, but which do not interfere with the interaction between the HDx and target polypeptide, can be derivatized to the wells of the plate, and HDx trapped in the wells by antibody conjugation. As above, preparations of an target polypeptide and a test compound are incubated in the HDx-presenting wells of the plate, and the amount of complex trapped in the well can be quantitated. Exemplary methods for detecting such complexes, in addition to those described above for the GST-immobilized complexes, include immunodetection of complexes using antibodies reactive with the target polypeptide, or which are reactive with HDx protein and compete with the target polypeptide; as well as enzyme-linked assays which rely on detecting an enzymatic activity associated with the target polypeptide, either intrinsic or extrinsic activity. In the instance of the latter, the enzyme can be chemically conjugated or provided as a fusion protein with the target polypeptide. To illustrate, the target polypeptide can be chemically cross-linked or genetically fused with horseradish peroxidase, and the amount of polypeptide trapped in the complex can be assessed with a chromogenic substrate of the enzyme, e.g. 3,3'-diamino-benzadine tetrahydrochloride or 4-chloro-1-naphthol. Likewise, a fusion protein comprising the polypeptide and glutathione-5-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-HDx antibodies, can be used. Alternatively, the protein to be detected in the complex can be "epitope tagged" in the form of a fusion protein which includes, in addition to the HDx sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharamacia, NJ).

In another embodiment of a drug screening, a two hybrid assay can be generated with an HDx and HDx-binding protein. Drug dependent inhibition or potentiation of the interaction can be scored.

Where the HDx proteins themselves, or in complexes with other proteins, are capable of binding DNA and modifying transcription of a gene, a transcriptional based assay using, for example, an transcriptional regulatory sequences responsive to HDx complexes operably linked to a detectable marker gene.

Furthermore, each of the assay systems set out above can be generated in a "differential" format as set forth above. That is, the assay format can provide information regarding specificity as well as potency. For instance, side-by-side comparison of a test compound's effect on different HDxs can provide information on selectivity, and permit the identification of compounds which selectively modulate the bioactivity of only a subset of the HDx family.

Furthermore, inhibitors of the enzymatic activity of each of the subject HDx proteins can be identified using assays derived from measuring the ability of an agent to inhibit catalytic conversion of a substrate by the subject proteins. For example, the ability of the subject HDx proteins to deacetylate a histone substrate, such as histone H4 (see examples), in the presence and absence of a candidate inhibitor, can be determined using standard enzymatic assays.

A number of methods have been employed in the art for assaying histone deacetylase activity, and can be incorporated in the drug screening assays of the present invention. In preferred embodiments, the assay will employ a labeled acetyl group linked to appropriate histone lysine residues as substrates. In other embodiments, a histone substrate peptide can be labeled with a group whose signal is dependent on the simultaneous presence or absence of an acetyl group, e.g., the label can be a fluorogenic group whose fluorescence is modulated (either quenched or potentiated) by the presence of the acetyl moiety. Using standard enzymatic analysis, the ability of a test agent to cause a statistically significant change in substrate conversion by a histone deacetylase can be measured, and as desirable, inhibition constants, e.g., $K_i$ values, can be calculated. The histone substrate can be provided as a purified or semi-purified polypeptide or as part of a cell lysate. Likewise, the histone deacetylase can be provided to the reaction mixture as a purified or semi-purified polypeptide or as a cell lysate. Accordingly, the reaction mixtures of the subject method can range from reconstituted protein mixtures derived with purified preparations of histones and deacetylases, to mixtures of cell lysates, e.g., by admixing baculovirus lysates containing recombinant histones and deacetylases.

In an exemplary embodiment, the histone substrate for the subject assay is provided by isolation of radiolabeled histones from metabolically labelled cells. To illustrate, as described by Hay et al. (1983) J Biol Chem 258:3726-3734, HeLa cells can be labelled in culture by addition of [$^3$H]acetate (New England Nuclear) to the culture media. The addition of butyrate, trapoxin or the like can be used to increase the abundance of acetylated histones in the cells. Radiolabelled histones can be isolated from the cells by extraction with $H_2SO_4$ (Marushige et al. (1966) *J Mol Biol* 15:160-174). Briefly, cells are homogenized in buffer, centrifuged to isolate a nuclear pellet, the subsequently homogenized nuclear pellet centrifuged through sucrose, and the resulting chromatin pellet extracted by addition of $H_2SO_4$ to yield [$^3$H]acetyl-labelled histones. In an alternate embodiment, nucleosome preparations containing [$^3$H]acetyl-labelled histones can be isolated from the labelled cells. As described in the art, nucleosomes can be isolated from cell preparations by sucrose gradient centrifugation (Hay et al. (1983) *J Biol Chem* 258:3726-3734; and Noll (1967) *Nature* 215:360-363), and polynucleosomes can be prepared by NaCl precipitation from micrococcal nuclease digested cells (Hay et al., supra). Similar procedures for isolating labelled histones from other cells types, including yeast, have been described. See, for example, Alonso et al. (1986) *Biochem Biophys Acta* 866: 161-169; and Kreiger et al. (1974) *Biol Chem* 249:332-334. In yet other embodiments, the histone is generated by recombinant gene expression, and includes an exogenous tag (e.g., an HA epitope, a poly(his) sequence or the like) which facilitates in purification from cell extracts. In still other embodiments, whole nuclei can be isolated from metabolically labelled cells by micrococcal nuclease digestion (Hay et al., supra)

In still another embodiment, the deacetylase substrate can be provided as an acetylated peptide including a sequence corresponding to the sequence about the specific lysyl residues acetylated on histone, e.g., a peptidyl portions of the core histones H2A, H2B, H3 or H4. Such fragments can be produced by cleavage of acetylated histones derived from metabolically labelled cells, e.g., such as by treatment with proteolytic enzymes or cyanogen bromide (Kreiger et al., supra). In other embodiments, the acetylated peptide can be provided by standard solid phase synthesis using acetylated lysine residues (Kreiger et al., supra).

Continuing with the illustrative use of [$^3$H]acetyl-labelled histones, the activity of a histone deacetylase in the subject assays is detected by measuring release of [$^3$H]acetate by standard scintillant techniques. In a merely illustrative example, a reaction mixture is provided which comprises a recombinant HDx protein suspended in buffer, along with a sample of [$^3$H]acetyl-labelled histones and (optionally) a test compound. The reaction mixture is maintained at a desired temperature and pH, such as 22° C. at pH7.8, for several hours, and the reaction terminated by boiling or other form of denaturation. Released [$^3$H]acetate is extracted and counted. For example, the quenched reaction mixture can be acidified with concentrated HCl, and used to create a biphasic mixture with ethyl acetate. The resulting 2 phase system is thoroughly mixed, centrifuged, and the ethyl acetate phase collected and counted by standard scintillation methods. Other methods for detecting acetate release will be easily recognized by those skilled in the art.

In yet another embodiment, the drug screening assay is derived to include a whole cell recombinantly expressing one or more of a target protein or HDx protein. The ability of a test agent to alter the activity of the HDx protein can be detected by analysis of the recombinant cell. For example, agonists and antagonists of the HDx biological activity can by detected by scoring for alterations in growth or differentiation (phenotype) of the cell. General techniques for detecting each are well known, and will vary with respect to the source of the particular reagent cell utilized in any given assay.

For example, quantification of proliferation of cells in the presence and absence of a candidate agent can be measured with a number of techniques well known in the art, including simple measurement of population growth curves. For instance, where the assay involves proliferation in a liquid medium, turbidimetric techniques (i.e. absorbence/transmittance of light of a given wavelength through the sample) can be utilized. For example, in the instance where the reagent cell is a yeast cell, measurement of absorbence of light at a wavelength between 540 and 600 nm can provide a conveniently fast measure of cell growth. Likewise, ability to form colonies in solid medium (e.g. agar) can be used to readily score for proliferation. In other embodiments, an HDx substrate protein, such as a histone, can be provided as a fusion protein which permits the substrate to be isolated from cell lysates and the degree of acetylation detected. Each of these techniques are suitable for high through-put analysis necessary for rapid screening of large numbers of candidate agents.

In addition, where the ability of an agent to cause or reverse a transformed phenotype, growth in solid media such as agar can further aid in establishing whether a mammalian cell is transformed.

Additionally, visual inspection of the morphology of the reagent cell can be used to determine whether the biological activity of the targeted HDx protein has been affected by the added agent. To illustrate, the ability of an agent to influence an apoptotic phenotype which is mediated in some way by a recombinant HDx protein can be assessed by visual microscopy. Likewise, the formation of certain cellular structures as part of differentiation, such as the formation of neuritic process, can be visualized under a light microscope.

The nature of the effect of test agent on reagent cell can be assessed by measuring levels of expression of specific genes, e.g., by reverse transcription-PCR. Another method of scoring for effect on Hdx activity is by detecting cell-type specific marker expression through immunofluorescent staining. Many such markers are known in the art, and antibodies are readily available. For example, the presence of chondroitin sulphate proteoglycans as well as type-II collagen are correlated with cartilage production in chondrocytes, and each can be detected by immunostaining. Similarly, the human kidney differentiation antigen gp160, human aminopeptidase A, is a marker of kidney induction, and the cytoskeletal protein troponin I is a marker of heart induction. In yet another embodiment, the alteration of expression of a reporter gene construct provided in the reagent cell provides a means of detecting the effect on HDx activity. For example, reporter gene constructs derived using the transcriptional regulatory sequences, e.g. the promoters, for developmentally regulated genes can be used to drive the expression of a detectable marker, such as a luciferase gene. In an illustrative embodiment, the construct is derived using the promoter sequence from a gene expressed in a particular differentiative phenotype.

It is also deemed to be within the scope of this invention that the recombinant HDx cells of the present assay can be generated so as to comprise heterologous HDx proteins (i.e. cross-species expression). For example, HDx proteins from one species can be expressed in the cells of another under conditions wherein the heterologous protein is able to rescue loss-of-function mutations in the host cell. For example, the reagent cell can be a yeast cell in which a human MDx protein (e.g. exogenously expressed) is the intended target for development of an anti-proliferative agent. To illustrate, the M778 strain, MATa ura3-52 trp1Δ1 his3-200 leu2-1 trk1Δ rpd3Δ:: HIS3, described by Vidal et al. (1991) *Mol Cell Biol* 6317-6327, which lacks a functional endogenous RPD3 gene can be transfected with an expression plasmid including a mammalian HDx gene in order to complement the RPD3 loss-offunction. For example, the coding sequence for HD1 can be cloned into a pRS integrative plasmid containing a selectable marker (Sikorski et al. (1989) *Genetics* 122:19-27), and resulting construct used to transform the M778 strain. The resulting cells should produce a mammalian HD1 protein which may be capable performing at least some of the functions of the yeast RPD3 protein. The HDx transformed yeast cells can be easier to manipulate than mammalian cells, and can provide access to certain assay formats, such as turbidity detection methods, which may not be obtainable with mammalian cells.

Moreover, the combination of the "mammalianized" strain with the strain M537 (MATa ura3-52 trp1Δ1 his3-200 leu2-1 trk1Δ, Vidal et al., supra) can provide an exquisitely sensitive cell-based assay for detecting agent which specifically inhibit, for example, the yeast RPD3 deacetylase.

In another aspect, the invention provides compounds useful for inhibition of HDxs. In a preferred embodiment, an HDx inhibitor compound of the invention can be represented by the formula A-B-C, in which A is a specificity element for selective binding to an HDx, B is a linker element, and C is an electrophilic moiety capable of reacting with a nucleophilic moiety of an HDx; with the proviso that the compound is not butyrate, trapoxin, or trichostatin.

In another aspect, the invention provides an affinity matrix for binding or purifying an HDx. In a preferred embodiment, the affinity matrix can be represented by the formula S-A-B-C, in which S is a solid or insoluble support, and A, B, and C are as described above. The solid or insoluble support S can be any of a variety of supports, many of which are known in the art, for synthesis of, or immobilization of, compounds, e.g., peptides, benzodiazepines, and the like. For a review of solid-supported synthesis, see, e.g., Hodge et al., *Polymer-supported Reactions in Organic Synthesis*, John Wiley & Sons, New York, 1980. The HDx inhibitor moiety A-B-C can be bonded directly to the support S, or can be bonded to the support S through a linking or spacing moiety, as is known in the art.

In another aspect, the invention provides a method of inhibiting an HDx. The method comprises contacting the HDx with a compound capable of inhibiting HDx activity, under conditions such that HDx activity is inhibited. In preferred embodiments, the compounds can be represented by the formula A-B-C, in which A, B, and C are as described above; with the proviso that the compound is not butyrate, trapoxin, or trichostatin.

In another aspect, the invention provides a method of purifying an HDx. The method includes contacting a reaction mixture comprising an HDx with an affinity matrix capable of selectively binding to an HDx, and separating at least one other component of the reaction mixture from the HDx. In a preferred embodiment, the affinity matrix can be represented by the formula S-A-B-C, in which S, A, B, and C are as described above.

In general, the elements A, B, and C of the inhibitor compounds are selected to permit selective binding to, and inhibition of, at least one HDx. The elements A, B, and C can be selected to provide specificity for particular HDxs. For example, a series of candidate HDx inhibitor compounds can be synthesized, e.g., according to the combinatorial methods described infra, and the library of candidate compounds screened against one or more HDxs to determine the compound or compounds with optimal activity and specificity for a particular HDx.

Thus, in preferred embodiments, the specificity element A is selected such that the HDx inhibitor compound binds selectively to an HDx. In general, the specificity element A will be selected according to factors such as the binding specificity of the HDx or HDxs to which the inhibitor compound should bind, ease of synthesis, stability in vivo or in vitro, and the like. In certain embodiments, the specificity element A is a cyclotetrapeptidyl moiety. In another embodiment, A is a substituted or unsubstituted aryl moiety. In yet another embodiment, A is a nonaromatic carbocycle. In still another embodiment, A is an amino acyl moiety (e.g., a natural or non-natural amino acyl moiety). In yet another embodiment, A is a heterocyclyl moiety.

In preferred embodiments, B is selected from the group consisting of substituted and unsubstituted $C_4$-$C_8$ alkylidene, $C_4$-$C_8$ alkenylidene, $C_4$-$C_8$ alkynylidene, and D-E-F, in which D and F are independently absent or $C_2$-$C_7$ alkylidene, $C_2$-$C_7$ alkenylidene, or $C_2$-$C_7$ alkynylidene, and E is O, S, or NR', in which R' is 14, lower alkyl, lower alkenyl, lower alkynyl, aralkyl, aryl, or heterocyclyl. The element B should be selected to permit the specificity element A to interact with an HDx such that specific binding occurs, while poising the electrophilic moiety C for reaction with a nucleophilic moiety of the HDx.

In a preferred embodiment, C is an electrophilic moiety that is approximately isosteric with an N-acetyl group (i.e., C has approximately the same steric bulk as an N-acetyl group) In preferred embodiments, the element C is capable of reacting, covalently or non-covalently, with a nucleophilic moiety of an HDx. In certain preferred embodiments, the element C is capable of binding (e.g., by chelation) to a metal ion, e.g., a divalent metal ion, e.g., zinc or calcium. In preferred embodiments, C is selected from the group consisting of $\alpha,\beta$-epoxyketones, $\alpha,\beta$-epoxythioketones, $\alpha,\beta$-epoxysulfoxides, hydroxamic acids, $\alpha$-haloketones, $\alpha$-halothioketones, $\alpha$-diazoketones, $\alpha$-diazothioketones, vinyl epoxides, trifluoromethylketone, trifluoromethylthioketone, enones (e.g., of ketones or thioketones), ynones (e.g., of ketones or thioketones), $\alpha,\beta$-aziridinoketones, hydrazones, boronic acids, carboxylates, amides (e.g., —C(O)-amino), sulfones, aldehyde, alkyl halides, epoxides, and the like.

Figure 6:
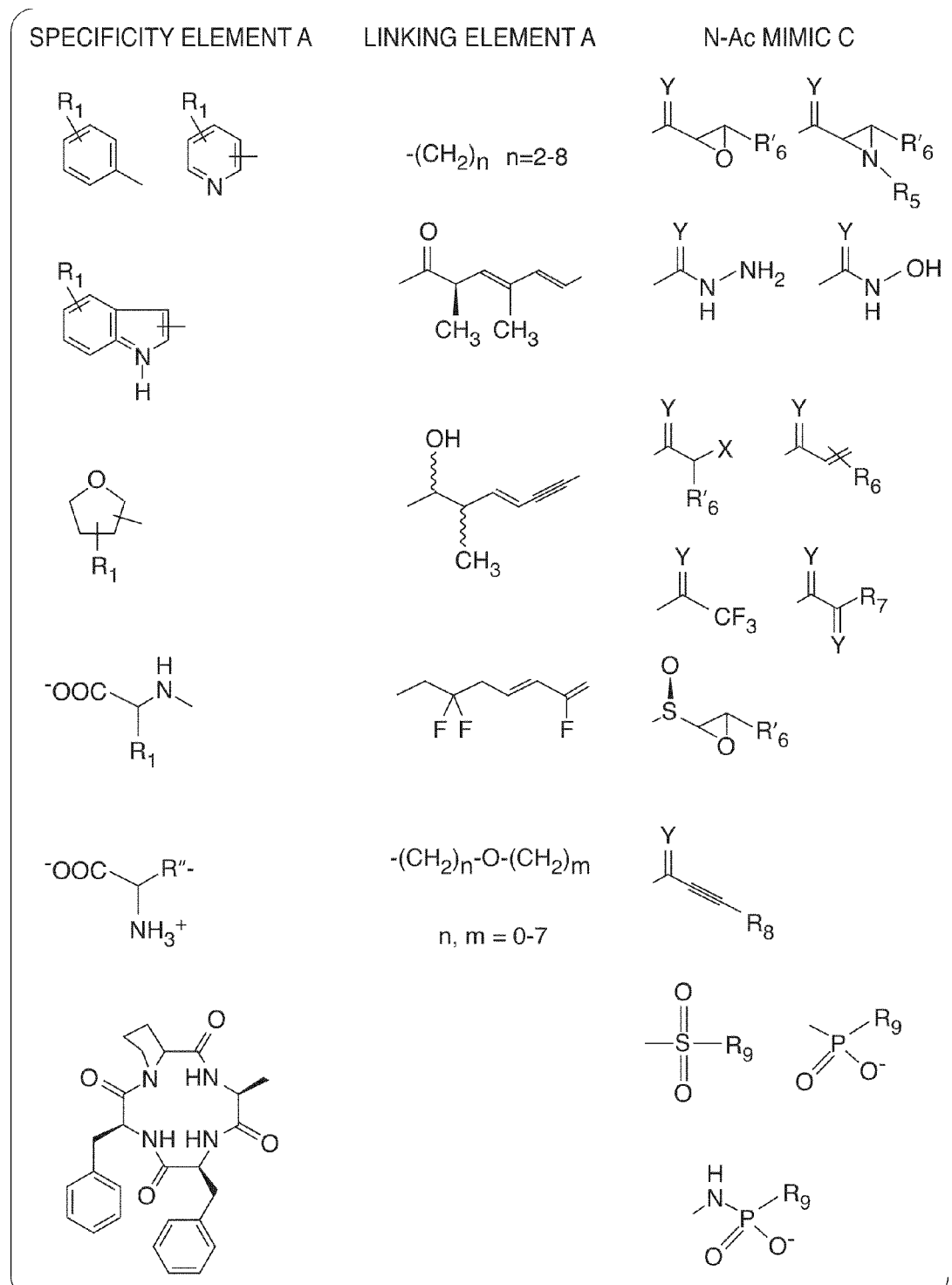
FIG. 6 depicts exemplary specificity elements (A), linker elements (B), and electrophilic moieties (C) for generating compounds which are capable of reacting with a nucleophilic moiety of an HDx protein.

In accordance with the foregoing, the moieties A, B, and C can illustratively be represented by the formulas depicted in FIG. 6, in which $R_1$ represents one or more substituents selected from the group consisting of amino, halogen, alkyl, alkenyl, alkynyl, aryl, aralkyl, heterocyclyl, azido, carboxyl, alkoxycarbonyl, hydroxyl, alkoxy, cyano, trifluoromethyl, and the like; R" is $C_1$-$C_8$ alkylidene, $C_2$-$C_8$ alkenylidene, or $C_2$-$C_8$ alkynylidene; $R_5$ is hydrogen, alkyl, alkoxycarbonyl, aryloxycarbonyl, alkylsulfonyl, arylsulfonyl or aryl; $R_6$ is hydrogen, alkyl, aryl, alkoxy, aryloxy, halogen, and the like; $R'_6$ is hydrogen, alkyl, alkenyl, alkynyl, aryl, and the like; $R_7$ is hydrogen, alkyl, aryl, alkoxy, aryloxy, amino, hydroxylamino, alkoxylamino, halogen, and the like; $R_8$ is hydrogen, alkyl, halogen, and the like; $R_9$ is hydrogen, alkyl, aryl, hydroxyl, alkoxy, aryloxy, amino, and the like; X is a good leaving group, e.g., diazo, halogen, a sulfate or sulfonate ester, e.g., a tosylate or mesylate, and the like; and Y is O or S.

In certain preferred embodiments, an HDx inhibitor compound can be represented by the formula A-B-C, in which A is selected from the group consisting of cycloalkyls, unsubstituted and substituted aryls, heterocyclyls, amino acyls, and cyclotetrapeptides; B is selected from the group consisting of substituted and unsubstituted $C_4$-$C_8$ alkylidene, $C_4$-$C_8$ alkenylidene, $C_4$-$C_8$ alkynylidene, $C_4$-$C_8$ enyne, and D-E-F, in which D and F are independently absent or a C—$C_7$ alkylidene, an $C_2$-$C_7$ alkenylidene, or an $C_2$-$C_7$ alkynylidene, and E is O, S, or NR', in which R' represents H, a lower alkyl, a lower alkenyl, a lower alkynyl, an aralkyl, aryl, or a heterocyclyl; and C is selected from the group consisting of

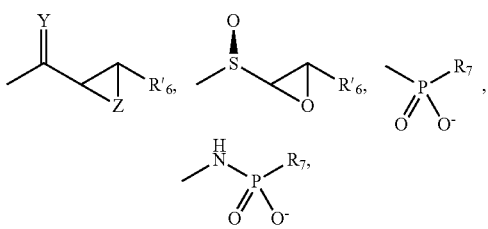

and B(OH)$_2$ (boronic acid); in which Z represents O, S, or NR$_5$, and Y, R$_5$, R'$_6$, and R$_7$ are as defined above. In preferred embodiments, R'$_6$ is hydrogen. In certain preferred embodiments, B is not a C$_4$-C$_8$ alkylidene. In preferred embodiments, if B is a C$_4$-C$_8$ alkylidene, C is not a boronic acid. In other preferred embodiments, the inhibitor compound is not trapoxin.

In certain preferred embodiments, an HDx inhibitor compound can be represented by the formula A-B-C, in which A is selected from the group consisting of cycloalkyls, unsubstituted and substituted aryls, heterocyclyls, amino acyls, and cyclotetrapeptides; B is selected from the group consisting of substituted and unsubstituted C$_4$-C$_8$ alkylidene, C$_4$-C$_8$ alkenylidene, C$_4$-C$_8$ alkynylidene, C$_4$-C$_8$ enyne, and D-E-F, in which D and F are independently absent or C$_1$-C$_7$ alkylidene, C$_2$-C$_7$ alkenylidene, or C$_2$-C$_7$ alkynylidene, and E is O, S, or NR', in which R' represents H, a lower alkyl, a lower alkenyl, a lower alkynyl, an aralkyl, an aryl, or a heterocyclyl; and C is selected from the group consisting of

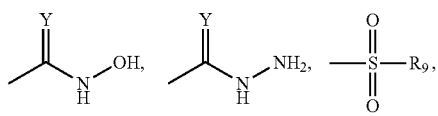

in which R$_9$ is as defined above. In preferred embodiments, B is not a C$_4$-C$_8$ alkylidene. In preferred embodiments, the inhibitor compound is not trichostatin.

In still another preferred embodiment, an HDx inhibitor compound can be represented by the formula A-B-C, in which A is selected from the group consisting of cycloalkyls, unsubstituted and substituted aryls, heterocyclyls, amino acyls, and cyclotetrapeptides; B is selected from the group consisting of substituted and unsubstituted C$_4$-C$_8$ alkylidene, C$_4$-C$_8$ alkenylidene, C$_4$-C$_8$ alkynylidene, C$_4$-C$_8$ enyne, and D-E-F, in which D and F are independently absent or a C$_1$-C$_7$ alkylidene, a C$_2$-C$_7$ alkenylidene, or a C$_2$-C$_7$ alkynylidene, and E is O, S, or NR', in which R' is H, lower alkyl, lower alkenyl, lower alkynyl, aralkyl, aryl, or heterocyclyl; and C is

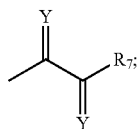

in which Y is O or S, and R$_7$ is as defined above.

Certain HDx inhibitor compounds of the present invention may exist in particular geometric or stereoisomeric forms. For example, amino acids can contain at least one chiral center. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts can be formed with an appropriate optically-active acid or base, followed by resolution of the diastereomers thus formed by fractional crystallization or chromatographic means well known in the art, and subsequent recovery of the pure enantiomers.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C$_1$-C$_{30}$ for straight chain, C$_3$-C$_{30}$ for branched chain), and more preferably 20 or fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as a carboxylate, alkoxycarbonyl, aryloxycarbonyl, alkylcarbonyl, arylcarbonyl, aldehyde, and the like), thiocarbonyl (such as a thioacid, alkoxycarbonyl, and the like), an alkoxyl, unsubstituted amino, mono- or disubstituted amino, amido, amidine, imine, nitro, azido, sulfhydryl, alkylthio, cyano, trifluoromethyl, sulfonato, sulfamoyl, sulfonamido, heterocyclyl, aralkyl, or an aromatic or heteroaromatic moiety. It will be understood by those skilled in the art that the moieties substituted on the hydrocarbon chain can themselves be substituted; as described above, if appropriate. Exemplary substituted alkyls are described below. Cycloalkyls can be further substituted with, e.g., alkyls, alkenyls, alkoxys, alkylthios, aminoalkyls, carbonyl-substituted alkyls, —CF$_3$, —CN, and the like.

The terms "alkenyl" and "alkynyl" refer to unsaturated aliphatic groups analogous in length and possible substitution to the alkyls described above, but that contain at least one double or triple bond respectively. The term "enyne" refers to an unsaturated aliphatic moiety having at least one double bond and one triple bond.

The terms "alkylidene," "alkenylidene," and "alkynylidene" are art-recognized and refer to moieties corresponding to alkyl, alkenyl, and alkynyl moieties as defined above, but having two valences available for bonding.

The term "aryl" as used herein includes 5-, 6- and 7-membered single-ring aromatic groups that may include from zero to four heteroatoms, for example, phenyl, pyrrolyl, furanyl, thiophenyl, imidazolyl, oxazolyl, thiazolyl, triazolyl, pyrazolyl, pyridyl, pyrazinyl, pyridazinyl and pyrimidyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azido, alkyl, aralkyl, alkenyl, alkynyl, cycloalkyl, hydroxyl, amino, nitro, sulfhydryl, imino, amido, carbonyl, carboxyl, silyl, ether, alkylthio, sulfonyl, sulfonamido, ketone, aldehyde, ester, a heterocyclyl, an aromatic or heteroaromatic moiety, —CF$_3$, —CN, or the like.

The term "aralkyl", as used herein, refers to an alkyl group substituted with an aryl group (e.g., an aromatic or heteroaromatic group).

The terms "heterocyclyl" or "heterocyclic group" refer to non-aromatic 4- to 10-membered ring structures, more preferably 4- to 7-membered rings, which ring structures include one to four heteroatoms (e.g., O, N, S, P and the like). Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, alkoxycarbonyl, aryloxycarbonyl, carboxyl, silyl, ether, alkylthio, alkylsulfonyl, arylsulfonyl, ketone (e.g., —C(O)-alkyl or —C(O)-aryl), aldehyde, heterocyclyl, an aryl or heteroaryl moiety, —CF$_3$, —CN, or the like.

Compounds represented by the formula A-B-C, in which A, B, and C have the values described supra, can be synthesized by standard techniques of organic synthesis. For example, precursor synthons corresponding to each of the moieties A, B, and C, or subunits thereof, can be coupled in linear or convergent syntheses to provide HDx inhibitor compounds, or compounds readily converted thereto. Syntheses of the HDx inhibitor compound trichostatin, and related compounds, have been reported; see, e.g., Massa, S. et al. (1990) *J. Med. Chem.* 33:2845-49; Mori, K., and Kosecki, K. (1988) *Tetrahedron* 44:6013-20; Koseki, K. and Mori, K. European Patent Application EP 331524 A2; Fleming, I. et al. (1983) *Tetrahedron* 39:841-46. Analogs of trapoxin have also been synthesized; see, e.g., Yoshida, H. and Sugita, K. (1992) *Jpn. J. Cancer Res.* 83:324-28.

Thus, in an illustrative synthesis, a compound represented by the formula A-B-C, in which A is an phenyl group, while B and C can have a variety of values, can be synthesized as shown below:

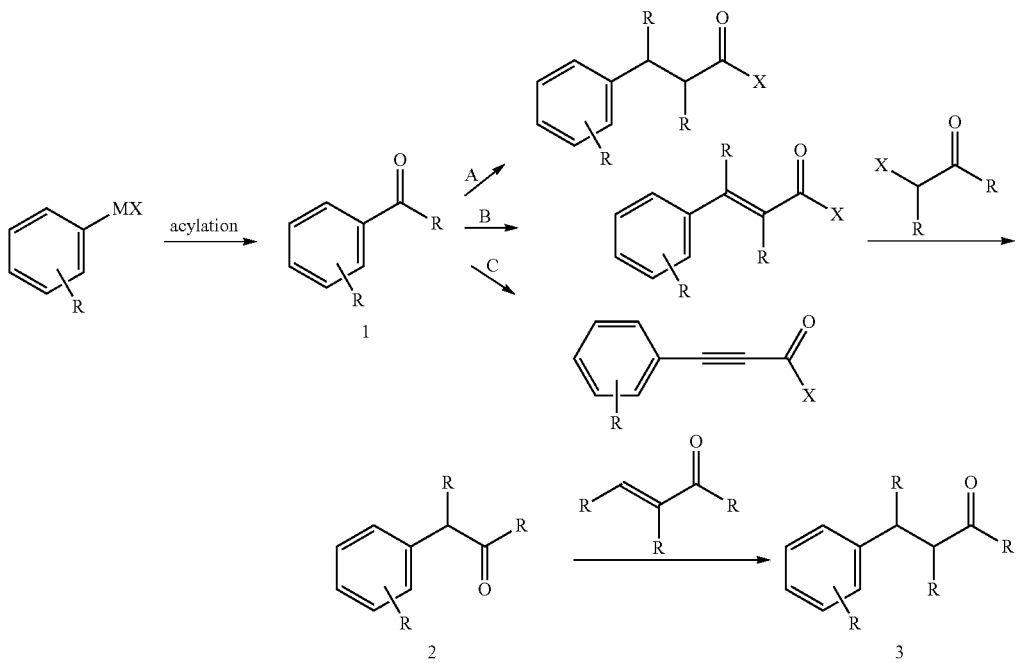

According to the Scheme, a functionalized organometallic aryl compound (MX=organometallic moiety; R is any substituent; X is a leaving group, e.g., halogen) (e.g., organotin, boronate, aryllithium, cuprate, Grignard reagent, etc.) is alkylated or acylated to provide functionalized compounds (e.g., the exemplary compounds 1, 2, or 3) which can be further elaborated to provide compounds with a wide variety of substituents and carbon backbones. Other A moieties (e.g., specificity elements) can be obtained by use of appropriate synthons, e.g., by substituting vinylorganometallic compounds for the organometallic aryl compound of the Scheme (followed by further treatment, e.g., reduction, of the vinyl group, if desired, to yield an alkyl A moiety). By way of illustration, as shown for compound 1, the carbonyl group can be used for elaboration, e.g., by reduction of the carbonyl group to an alcohol, conversion of the alcohol to a tosylate, and nucleophilic displacement of the tosylate by an acyl compound (e.g., a ketone or ester) to provide a chain-lengthened product (Route A), which can be converted to a C(O)X functionality (e.g., by hydrolysis of an ester and conversion of the resulting carboxylic acid to an acid chloride). Alternatively, the carbonyl group of 1 can be used for olefination (Route B), e.g., Horner-Emmons olefination, to provide an elaborated alkenyl compound. Also, the carbonyl group can be converted to an alkynyl functionality, e.g., via the Corey-Fuchs procedure, to provide an elaborated alkynyl compound. For purposes of clarity, only certain chain lengths and functional group patterns are shown in the scheme; however, the skilled artisan will appreciate that many other compounds, with a variety of B moieties (i.e., linking moieties), can be synthesized through analogous procedures. The C(O)X functionality (e.g., an acid chloride where X is Cl) can be converted to functional groups such as amide, hydrazido, trifluoromethylketone, enone, epoxide, aziridine, and the like, through methods conventional in the art. Thus, the synthetic pathways shown in the Scheme provide access to compounds having a variety of C moieties (e.g., reactive moieties) suitable for substitution in the subject HDx inhibitors.

In vitro chemical synthesis provides a method for generating libraries of compounds that can be screened for ability to bind to or inhibit a target protein, e.g., an HDx. Although in vitro methods have previously been used in the pharmaceutical industry to identify potential drugs, recently developed methods have focused on rapidly and efficiently generating and screening large numbers of compounds and are amenable to generating HDx inhibitor compound libraries for use in the subject method. The various approaches to simultaneous preparation and analysis of large numbers of compounds (herein "combinatorial synthesis") each rely on the fundamental concept of synthesis on a solid support introduced for peptides by Merrifield in 1963 (Merrifield, R. B. (1963) *J Am Chem Soc* 85:2149-2154). Many types of solid matrices have been successfully used in solid-phase synthesis, and can be selected according to the type of chemistry to be performed on the immobilized moieties, as is discussed in more detail below.

Several synthetic schemes have been suggested or employed for the combinatorial synthesis of organic compounds (see, e.g., E. M. Gordon et al., *J. Med. Chem.* 37:1385-1401 (1994)).

Multipin Synthesis

One method for combinatorial synthesis of compounds is the multipin synthesis method. Briefly, Geysen and co-workers (Geysen et al. (1984) *PNAS* 81:3998-4002) introduced a method for generating compounds by a parallel synthesis on polyacrylic acid-grated polyethylene pins arrayed in the microtitre plate format. In the original experiments, about 50 nmol of a single compound was covalently linked to the spherical head of each pin, and interactions of each compound with a receptor or antibody could be determined in a direct binding assay. The Geysen technique can be used to synthesize and screen thousands of compounds per week using the multipin method, and the tethered compounds may be reused in many assays. In subsequent work, the level of compound loading on individual pins has been increased to as much as 2 μmol/pin by grafting greater amounts of functionalized acrylate derivatives to detachable pin heads, and the size of the compound library has been increased (Valerio et al. (1993) *Int J Pept Protein Res* 42:1-9). Appropriate linker moieties have also been appended to the pins so that the compounds may be cleaved from the supports after synthesis for assessment of purity and evaluation in competition binding or functional bioassays (Bray et al. (1990) *Tetrahedron Lett* 31:5811-5814; Valerio et al. (1991) *Anal Biochem* 197: 168-177; Bray et al. (1991) *Tetrahedron Lett* 32:6163-6166).

More recent applications of the multipin method have taken advantage of the cleavable linker strategy to prepare soluble compound libraries (Maeji et al. (1990) *J Immunol Methods* 134:23-33; Gammon et al. (1991) *J Exp Med* 173: 609-617; Mutch et al. (1991) *Pept Res* 4:132-137).

Divide-Couple-Recombine

In another embodiment, a variegated library of HDx inhibitor compounds is provided on a set of beads utilizing the strategy of divide-couple-recombine (see, e.g., Houghten (1985) *PNAS* 82:5131-5135; and U.S. Pat. Nos. 4,631,211; 5,440,016; 5,480,971). Briefly, as the name implies, at each synthesis step where degeneracy (e.g., a plurality of different moieties) is introduced into the library, the beads are divided into as many separate groups to correspond to the number of different residues (e.g., functional groups or other moieties) to be added at that position, the different residues coupled in separate reactions, and the beads recombined into one pool for the next step.

In one embodiment, the divide-couple-recombine strategy can be carried out using the so-called "tea bag" method first developed by Houghten, where synthesis occurs on resin that is sealed inside porous polypropylene bags (Houghten et al. (1986) *PNAS* 82:5131-5135). Residues are coupled to the resins by placing the bags in solutions of the appropriate individual activated monomers, while all common steps such as resin washing and deprotection (if appropriate) are performed simultaneously in one reaction vessel. At the end of the synthesis, each bag contains a single compound, and the compounds may be liberated from the resins using a multiple cleavage apparatus (Houghten et al. (1986) *Int J Pept Protein Res* 27:673-678). This technique offers advantages of considerable synthetic flexibility and has been partially automated (Beck-Sickinger et al. (1991) *Pept Res* 4:88-94). Moreover, compounds can be produced in sufficient quantities (>500 μmol) for purification and complete characterization if desired.

Synthesis using the tea-bag approach is useful for the production of a library, albeit of limited size, as is illustrated by its use in a range of molecular recognition problems including antibody epitope analysis (Houghten et al. (1986) *PNAS* 82:5131-5135), peptide hormone structure-function studies (Beck-Sickinger et al. (1990) *Int J Pept Protein Res* 36:522-530; Beck-Sickinger et al. (1990) *Eur J Biochem* 194:449-456), and protein conformational mapping (Zimmerman et al. (1991) *Eur J Biochem* 200:519-528).

Combinatorial Synthesis on Nontraditional Solid Supports

The search for innovative methods of solid-phase synthesis has led to the investigation of alternative polymeric supports to the polystyrene-divinylbenzene matrix originally popularized by Merrifield. Cellulose, either in the form of paper disks (Blankemeyer-Menge et al. (1988) *Tetrahedron Lett* 29-5871-5874; Frank et al. (1988) *Tetrahedron* 44:6031-6040; Eichler et al. (1989) *Collect Czech Chem Commun* 54:1746-1752; Frank, R. (1993) *Bioorg Med Chem Lett* 3:425-430) or cotton fragments (Eichler et al. (1991) *Pept Res* 4:296-307; Schmidt et al. (1993) *Bioorg Med Chem Lett* 3:441-446) has been successfully functionalized for peptide synthesis. Typical loadings attained with cellulose paper range from 1 to 3 μmol/cm$^2$, and HPLC analysis of material cleaved from these supports indicates a reasonable quality for the synthesized peptides. Alternatively, peptides may be synthesized on cellulose sheets via non-cleavable linkers and then used in ELISA-based binding studies (Frank, R. (1992) *Tetrahedron* 48:9217-9232). The porous, polar nature of this support may help suppress unwanted nonspecific protein binding effects. In one convenient configuration synthesis occurs in an 8×12 microtiter plate format. Frank has used this technique to map the dominant epitopes of an antiserum raised against a human cytomegalovirus protein, following the overlapping peptide screening (Pepscan) strategy of Geysen (Frank, R. (1992) *Tetrahedron* 48:9217-9232). Other membrane-like supports that may be used for solid-phase synthesis include polystyrene-grafted polyethylene films (Berg et al. (1989) *J Am Chem Soc* 111:8024-8026).

Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The technique combines two well-developed technologies: solid-phase synthesis chemistry and photolithography. The high coupling yields of solid-phase reactions allows efficient compound synthesis, and the spatial resolution of photolithography affords miniaturization. The merging of these two technologies is done through the use of photolabile protecting groups, e.g., amino protecting groups, in the synthetic procedure.

The key points of this technology are illustrated in Gallop et al. (1994) *J Med Chem* 37:1233-1251. A synthesis substrate is prepared for compound synthesis through the covalent attachment of photolabile nitroveratryloxycarbonyl (NVOC) protected amino linkers. Light is used to selectively activate a specified region of the synthesis support for coupling. Removal of the photolabile protecting groups by lights (deprotection) results in activation of selected areas. After activation, the first of a set of residues, each bearing a photolabile protecting group, is exposed to the entire surface. Coupling only occurs in regions that were addressed by light in the preceding step. The reagent solution is removed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed. The target can be labeled with a fluorescent reporter group to facilitate the identification of specific interactions with individual members of the matrix.

In a light-directed chemical synthesis, the products depend on the pattern of illumination and on the order of addition of reactants. By varying the lithographic patterns, many different sets of test compounds can be synthesized in the same number of steps; this leads to the generation of many different masking strategies.

Encoded Combinatorial Libraries

In yet another embodiment, the subject method provides an HDx inhibitor compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. Two forms of encoding have been reported: encoding with sequenceable bio-oligomers (e.g., oligonucleotides and peptides), and binary encoding with non-sequenceable tags.

Tagging with Sequenceable Bio-Oligomers

The principle of using oligonucleotides to encode combinatorial synthetic libraries was described in 1992 (Brenner et al. (1992) *PNAS* 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, HDx inhibitor compound libraries can be derived and screened using HDxs of the subject invention.

It is noted that an alternative approach useful for generating nucleotide-encoded synthetic peptide libraries employs a branched linker containing selectively protected OH and $NH_2$ groups (Nielsen et al. (1993) *J Am Chem Soc* 115:9812-9813; and Nielsen et al. (1994) *Methods Compan Methods Enzymol* 6:361-371). This approach requires that equimolar quantities of test peptide and tag co-exist, though this may be a potential complication in assessing biological activity, especially with nucleic acid based targets.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis on non-oligomeric libraries. In preferred embodiments, the libraries employ linkers permitting selective detachment of the test HDx inhibitor compound library member for bioassay, in part (as described infra) because assays employing beads limit the choice of targets, and in part because the tags are potentially susceptible to biodegradation.

Peptides themselves have been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the ligand strand.

In an alternative approach (Nikolaiev et al. (1993) *Pept Res* 6:161-170), branched linkers are employed so that the coding unit and the test peptide are both attached to the same functional group on the resin. In one embodiment, a linker can be placed between the branch point and the bead so that cleavage releases a molecule containing both code and ligand (Ptek et al. (1991) *Tetrahedron Lett* 32:3891-3894). In another embodiment, the linker can be placed so that the test peptide can be selectively separated from the bead, leaving the code behind. This last construct is particularly valuable because it permits screening of the test peptide without potential interference, or biodegradation, of the coding groups. Examples in the art of independent cleavage and sequencing of peptide library members and their corresponding tags has confirmed that the tags can accurately predict the peptide structure.

It is noted that peptide tags are more resistant to decomposition during ligand synthesis than are oligonucleotide tags, but they must be employed in molar ratios nearly equal to those of the ligand on typical 130 μm beads in order to be successfully sequenced. As with oligonucleotide encoding, the use of peptides as tags requires complex protection/deprotection chemistries.

Non-Sequenceable Tagging: Binary Encoding

An alternative form of encoding the test peptide library employs a set of non-sequenceable tagging molecules (e.g., molecules having electrophoric moieties) that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable O-nitrobenzyl linker. This approach is convenient when preparing combinatorial libraries of peptides or other amine-containing molecules. A more versatile system has, however, been developed that permits encoding of essentially any combinatorial library. Here, the ligand is attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for bioassay in solution and subsequent decoding by ECGC after oxidative detachment of the tag sets.

Binary encoding with tags, e.g., electrophoric tags, has been particularly useful in defining selective interactions of substrates with synthetic receptors (Borchardt et al. (1994) *J Am Chem Soc* 116:373-374), and model systems for understanding the binding and catalysis of biomolecules. Even using detailed molecular modeling, the identification of the selectivity preferences for synthetic receptors has required the manual synthesis of dozens of potential substrates. The use of encoded libraries makes it possible to rapidly examine all the members of a potential binding set. The use of binary-encoded libraries has made the determination of binding selectivities so facile that structural selectivity has been reported for four novel synthetic macrobicyclic and tricyclic receptors in a single communication (Wennemers et al. (1995) *J Org Chem* 60:1108-1109; and Yoon et al. (1994) *Tetrahedron Lett* 35:8557-8560) using the encoded library mentioned above. Similar facility in defining specificity of interaction would be expected for many other biomolecules.

Although the several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the tags are attached directly to the solid phase (Ohlmeyer et al. (1995) *PNAS* 92:6027-6031) and provide guidance for generating the subject HDx inhibitor compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, ligands are partially detached and transferred to assay plates; third, a bioassay identifies the active wells; fourth, the corresponding beads are rearrayed singly into new microtiter plates; fifth, single active compounds are identified; and sixth, the structures are decoded.

The above approach was employed in screening for carbonic anhydrase (CA) binding and identified compounds which exhibited nanomolar affinities for CA. Unlike sequenceable tagging, a large number of structures can be rapidly decoded from binary-encoded libraries (a single ECGC apparatus can decode 50 structures per day). Thus, binary-encoded libraries can be used for the rapid analysis of structure-activity relationships and optimization of both potency and selectivity of an active series. The synthesis and screening of large unbiased binary encoded HDx inhibitor compound libraries for lead identification, followed by preparation and analysis of smaller focused libraries for lead optimization, offers a particularly powerful approach to discovery of HDx inhibitor compounds.

Figure 7:
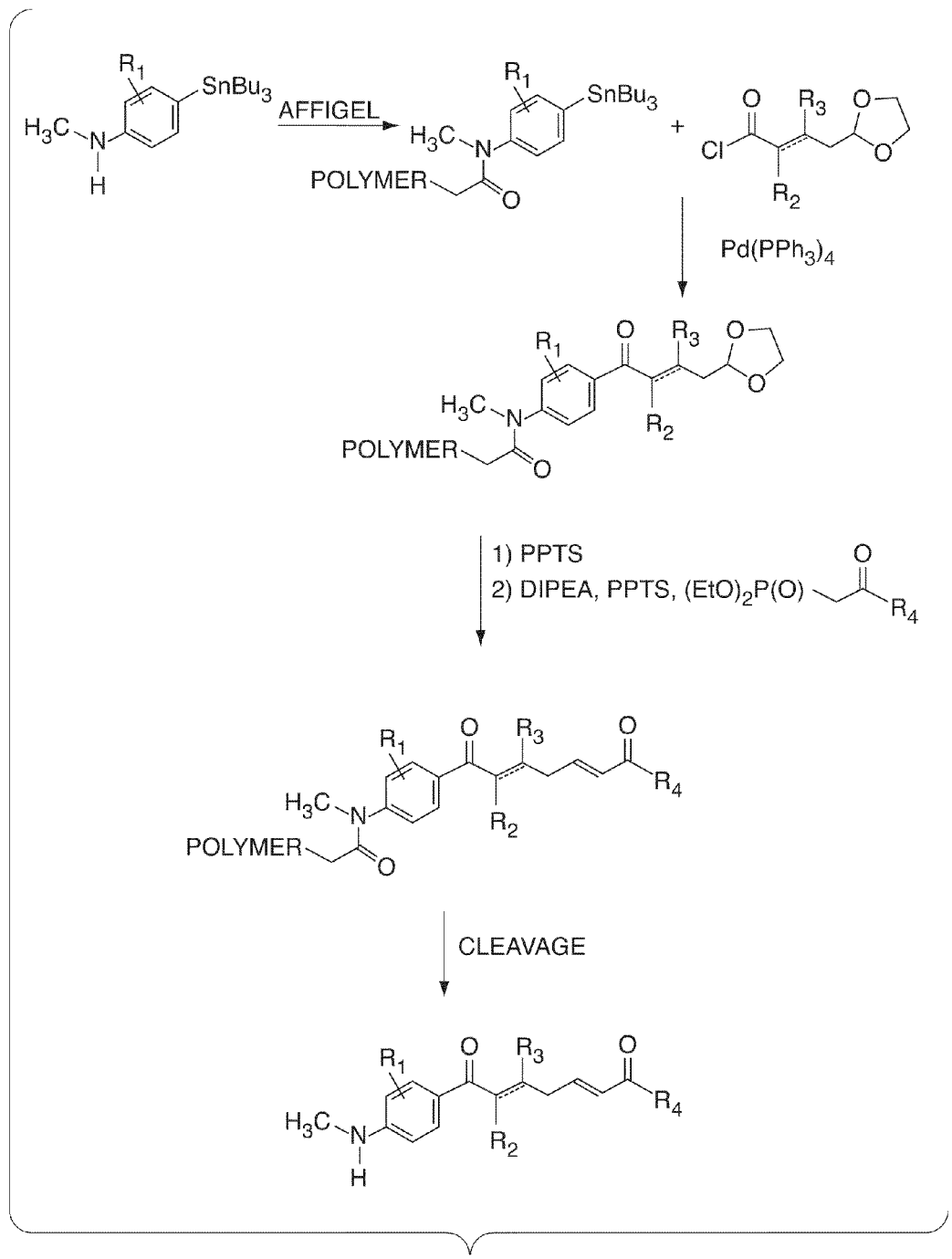
FIG. 7 illustrates an exemplary synthesis of trichostatin analogs.

HDx inhibitor compounds can be synthesized on solid support by appropriate functionalization for attachment to a solid matrix, or alternatively, by solution-phase synthesis followed by immobilization through an appropriate functional group. Thus, in an illustrative embodiment, an HDx inhibitor compound, which is analogous to trichostatin, can be synthesized on a solid support by attachment through an amino group of the specificity element A, as shown in FIG. 7. The solid support is preferably capable of withstanding synthetic conditions required to synthesize the requisite compounds. The compound can preferably be released from the solid support, e.g., by selective cleavage of an amide bond.

The synthetic steps employed to synthesize compounds on solid support are preferably selected to allow a wide variety of residues (e.g., building blocks) to be coupled to the immobilized moieties, preferably under mild conditions. Suitable reaction chemistries include well-known carbon-carbon bond forming reactions such as the Stille and Suzuki couplings, as well as Horner-Emmons reactions, Ni/Cr mediated couplings, and the like. Particularly preferred coupling reactions can be performed in the presence of water and do not require harsh conditions or expensive reagents.

Thus, in an exemplary synthesis shown in FIG. 7, substituted N-methyl-4-(tributyltin)anilines (in which $R_1$ represents one or more substitutions, e.g., hydrogen, halogen, alkyl, alkoxy, and the like) are coupled in a plurality of reaction vessels to beads of a solid support (e.g., Affigel). The beads are further divided into a plurality of reaction vessels, and suspended in a solvent such as DMF, and one acid chloride building block (corresponding to linking element B) is introduced into each vessel ($R_2$ and $R_3$ represent, e.g., hydrogen, halogen, alkyl, and the like; and the broken line represents an optional double bond). The reactions are stirred under an inert gas (e.g. nitrogen) and a palladium catalyst (e.g., Pd(PPh$_3$)$_4$) is added (0.1-1.0 mol %). The reaction is stirred for 1-24 hours. Upon completion of the reaction, the beads are washed, and placed in a plurality of vessels. The aldehyde moiety is deprotected by mild acid treatment (e.g., PPTS in MeOH), and the beads are again washed and placed in a plurality of reaction vessels, and the beads are suspended in dry acetonitrile. One building block (corresponding to the reactive element C) is then added to each reaction vessel. As illustratively shown in FIG. 7, a plurality of phosphonates can be employed (R$_4$ represents, e.g., alkyl, alkenyl, alkynyl, alkoxy, and the like). A Horner-Emmons reaction is performed by addition of LiCl (1.1 equiv.) and diisopropylethylamine (DIPEA) or DBU (1.2 equiv). Upon completion of the reaction, the beads are washed with water and acetonitrile, and then dried to yield a library of candidate HDx inhibitor compounds on solid support. The compounds can then be released from the solid support into solution; or the compounds can be screened while attached to the solid support.

The above combinatorial synthesis can be performed in an encoded mode, e.g., the binary tagging method described supra, by addition of the appropriate tag for each monomer. In this mode, after each reaction has been performed and the corresponding tag attached, the beads from all reactions can be recombined and then divided into aliquots for further derivatization. This method provides the advantage of ease of handling when large libraries are to be synthesized. Regardless of the method of synthesis, the combinatorial library can be screened for activity according to known methods (see, e.g., Gordon et al., supra).

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a deacetylase inhibitor of the present invention which is effective for producing some desired therapeutic effect by inhibiting histone deacetylation in at least a sub-population of cells in an animal and thereby blocking the biological consequences of that event in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject deacetylase inhibitor agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present deacetylase inhibitors may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the deacetylase inhibitory compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending, upon the host being treated, the particular mode of administration. The amount of active ingredient which can be combined with a carrier material to produce a single dosage form will generally be that amount of the deacetylase inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a deacetylase inhibitor of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A deacetylase inhibitor of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered deacetylase inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the deacetylase inhibitors of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active deacetylase inhibitor, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active deacetylase inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a deacetylase inhibitor of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active deacetylase inhibitor of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the deacetylase inhibitor in the proper medium. Absorption enhancers can also be used to increase the flux of the deacetylase inhibitor across the skin. The rate of such flux can be controlled by either providing a rate controlling membrane or dispersing the deacetylase inhibitor in a polymer matrix or gel.

Ophthalmic formulations, eye ointments, powders, solutions and the like, are also contemplated as being within the scope of this invention.

Pharmaceutical compositions of this invention suitable for parenteral administration comprise one or more deacetylase inhibitors of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject deacetylase inhibitors in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

These deacetylase inhibitor may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular deacetylase inhibitor employed, or the ester, salt or amide thereof, the route of administration, the time of administration, the rate of excretion of the particular compound being employed, the duration of the treatment, other drugs, compounds and/or materials used in combination with the particular deacetylase inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Another aspect of the present invention relates to a method of inducing and/or maintaining a differentiated state, enhancing survival, and/or inhibiting (or alternatively potentiating) proliferation of a cell, by contacting the cells with an agent which modulates HDx-dependent transcription. For instance, it is contemplated by the invention that, in light of the present finding of an apparently broad involvement of HDx proteins in the control of chromatin structure and, thus, transcription and replication, the subject method could be used to generate and/or maintain an array of different tissue both in vitro and in vivo. An "HDx therapeutic," whether inhibitory or potentiating with respect to modulating histone deacetylation, can be, as appropriate, any of the preparations described above, including isolated polypeptides, gene therapy constructs, antisense molecules, peptidomimetics or agents identified in the drug assays provided herein.

The HDx compounds of the present invention are likely to play an important role in the modulation of cellular proliferation. There are a wide variety of pathological cell proliferative conditions for which HDx therapeutics of the present invention may be used in treatment. For instance, such agents can provide therapeutic benefits where the general strategy being the inhibition of an anomalous cell proliferation. Diseases that might benefit from this methodology include, but are not limited to various cancers and leukemias, psoriasis, bone diseases, fibroproliferative disorders such as involving connective tissues, atherosclerosis and other smooth muscle proliferative disorders, as well as chronic inflammation.

In addition to proliferative disorders, the present invention contemplates the use of HDx therapeutics for the treatment of differentiative disorders which result from, for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

It will also be apparent that, by transient use of modulators of HDx activities, in vivo reformation of tissue can be accomplished, e.g. in the development and maintenance of organs. By controlling the proliferative and differentiative potential for different cells, the subject HDx therapeutics can be used to reform injured tissue, or to improve grafting and morphology of transplanted tissue. For instance, HDx antagonists and agonists can be employed in a differential manner to regulate different stages of organ repair after physical, chemical or pathological insult. For example, such regimens can be utilized in repair of cartilage, increasing bone density, liver repair subsequent to a partial hepatectomy, or to promote regeneration of lung tissue in the treatment of emphysema. The present method is also applicable to cell culture techniques.

In one embodiment, the HDx therapeutic of the present invention can be used to induce differentiation of uncommitted progenitor cells and thereby give rise to a committed progenitor cell, or to cause further restriction of the developmental fate of a committed progenitor cell towards becoming a terminally-differentiated cell. For example, the present method can be used in vitro or in vivo to induce and/or maintain the differentiation of hematopoietic cells into erythrocytes and other cells of the hematopoietic system. In, an illustrative embodiment, the effect of erythropoietin (EPO) on the growth of EPO-responsive erythroid precursor cells is increased to influence their differentiation into red blood cells. For example, as a result of administering an inhibitor of histone deacetylation, the amount of EPO, or other differentiating agent, required for growth and/or differentiation is reduced (PCT/US92/07737). Accordingly, the HDx therapeutics of the present invention, particularly those which antagonize HDx deacetylase activity, can be administered alone or in conjunction with EPO and in a suitable carrier to vertebrates to promote erythropoiesis. Alternatively, cells could be treated ex vivo. Such treatment is contemplated in the treatment of a variety of disease states, including in individuals who require bone marrow transplants (e.g. patients with aplastic anemia, acute leukemias, recurrent lymphomas, or solid tumors).

To illustrate, prior to receiving a bone marrow transplant, a recipient is prepared by ablating or removing endogenous hematopoietic stem cells. Such treatment is usually carried out by total body irradiation or delivery of a high dose of an alkylating agent or other chemotherapeutic, cytotoxic agent, Anklesaria, et al. (1987) PNAS 84:7681-7685). Following preparation of the recipient, donor bone marrow cells are injected intravenously. Optionally, the HDx therapeutics of the present invention could be contacted with the cells ex vivo or administered to the subject with the reimplanted cells.

It is also contemplated that there may be cell-type specific HDx proteins, and/or that some cell types may be more sensitive to modulation of HDx deacetylase activities. Even within a cell type, the stage of differentiation or position in the cell cycle could influence their response to an HDx therapeutic. Accordingly, the present invention contemplates the use of agents which modulate histone deacetylase activity to specifically inhibit or activate certain cell types. In an illustrative example, T cell proliferation could be preferentially inhibited in order to induce tolerance by using a procedure similar to that for inducing tolerance using sodium butyrate (see, for example, PCT/US93/03045). To illustrate, the HDx therapeutics of the present invention may be used to induce antigen-specific tolerance in any situation in which it is desirable to induce tolerance, such as autoimmune diseases, in allogeneic or xenogeneic transplant recipients, or in graft versus host (GVH) reactions. According to the invention, tolerance will typically be induced by presenting the tolerizing compound (e.g., an HDx inhibitor) substantially contemporaneously with the antigen, i.e. reasonably close together in time with the antigen. In preferred embodiments the HDx therapeutic will be administered after presentation of the antigen, so that they will have their effect after the particular repertoire of Th cells begins to undergo clonal expansion.

Yet another aspect of the present invention concerns the application of HDx therapeutics to modulating morphogenic signals involved in organogenic pathways. Thus, it is contemplated by the invention that compositions comprising HDx therapeutics can also be utilized for both cell culture and therapeutic methods involving generation and maintenance of tissue.

In a further embodiment of the invention, the subject HDx therapeutics will be useful in increasing the amount of protein produced by a cell or recombinant cell. The cell may include any primary cell isolated from any animal, cultured cells, immortalized cells, and established cell lines. The animal cells used in the present invention include cells which intrinsically have an ability to produce a desired protein; cells which are induced to have an ability to produce a desired protein, for example, by stimulation with a cytokine such as an interferon, an interleukin; genetically engineered cells into which a gene for a desired protein is introduced. The protein produced by the process could include any peptides or proteins, including peptide hormone or proteinaceous hormones such as any useful hormone, cytokine, interleukin, or protein which it may be desirable to have in purified form and/or in large quantity.

Another aspect of the invention features transgenic non-human animals which express a heterologous HDx gene of the present invention, or which have had one or more genomic HDx genes disrupted in at least one of the tissue or cell-types of the animal. Accordingly, the invention features an animal model for developmental diseases, which animal has one or more HDx allele which is mis-expressed. For example, a mouse can be bred which has one or more HDx alleles deleted or otherwise rendered inactive. Such a mouse model can then be used to study disorders arising from mis-expressed HDx genes, as well as for evaluating potential therapies for similar disorders.

Another aspect of the present invention concerns transgenic animals which are comprised of cells (of that animal) which contain a transgene of the present invention and which preferably (though optionally) express an exogenous HDx protein in one or more cells in the animal. An HDx transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of an HDx protein can be essential for many forms of lineage analysis and can additionally provide a means to assess the effects of, for example, lack of HDx expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject HDx proteins. For example, excision of a target sequence which interferes with the expression of a recombinant HDx gene, such as one which encodes an antagonistic homolog or an antisense transcript, can be designed to activate expression of that gene. This interference with expression of the protein can result from a variety of mechanisms, such as spatial separation of the HDx gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) PNAS 89:6232-6236; Orban et al. (1992) PNAS 89:6861-6865) or the FLP recombinase system of *Saccharomyces cerevisiae* (O'Gorman et al. (1991) Science 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant HDx protein can be regulated via control of recombinase expression.

Use of the cre/loxP recombinase system to regulate expression of a recombinant HDx protein requires the construction of a transgenic animal containing transgenes encoding both the Cre recombinase and the subject protein. Animals containing both the Cre recombinase and a recombinant HDx gene can be provided through the construction of "double" transgenic animals. A convenient method for providing such animals is to mate two transgenic animals each containing a transgene, e.g., an HDx gene and recombinase gene.

One advantage derived from initially constructing transgenic animals containing an HDx transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic HDx transgene is silent will allow the study of progeny from that founder in which disruption of HDx mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the HDx transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, an HDx transgene could remain silent into adulthood until "turned on" by the introduction of the trans-activator.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) PNAS 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce HDx transgenes into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

Methods of making HDx knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous HDx gene, such that tissue specific and/or temporal control of inactivation of an HDx allele can be controlled as above.

EXEMPLIFICATION

The invention, now being generally described, will be more readily understood by reference to the following examples, which are included merely for purposes of illustration of certain aspects and embodiments of the present invention and are not intended to limit the invention.

Example 1

Trapoxin is a microbially derived cyclotetrapeptide that inhibits histone deacetylation in vivo and causes mammalian cells to arrest in the cell cycle. A trapoxin affinity matrix was used to isolate two nuclear proteins that copurified with histone deacetylase activity. Both proteins were identified by peptide microsequencing, and a cDNA encoding the histone deacetylase catalytic subunit (HD1) was cloned from a Jurkat T cell library. As the predicted protein is highly similar to the yeast transcriptional regulator RPD3, this study supports a role for histone deacetylase as a key regulator of eukaryotic transcription.

A requirement for a functional histone deacetylase in cell cycle progression has been implicated by the discovery that two cytostatic agents, trapoxin and trichostatin (FIG. 1A), inhibit histone deacetylation in cultured mammalian cells and in fractioned cell extracts (4). In addition to causing $G_1$ and $G_2$ phase cell cycle arrest, these natural products alter gene expression and induce certain mammalian cell lines to differentiate. Whereas sodium butyrate also has these properties, both trapoxin and trichostatin are five orders of magnitude more potent.

Trapoxin is an "irreversible" inhibitor of histone deacetylase activity and its molecular structure offers clues as to how it could form a covalent bond with a nucleophilic active site residue. First, trapoxin contains an electrophilic epoxyketone that is essential for biological activity (5). Second, the aliphatic epoxyketone side chain is approximately isosteric with N-acetyl lysine (FIG. 1A). Trapoxin likely acts as a substrate mimic, with epoxyketone poised to alkylate an active site nucleophile. We therefore regarded trapoxin as a tool that could reveal the molecular identity of histone deacetylase, so that its role in transcriptional regulation and cell cycle progression could be elucidated.

Tritium-labeled trapoxin was prepared by total synthesis and used to identify trapoxin binding protein in crude extracts from bovine thymus. We used a charcoal precipitation assay to detect a specific trapoxin binding activity primarily in the nuclear fraction of the extracts (6). The binding activity was saturable with nanomolar concentrations of [$^3$H]trapoxin and was completed by the simultaneous addition of unlabeled trapoxin. Trichostatin also competed with [$^3$H]trapoxin (for synthesis, see Example 2), suggesting that both of these compounds exert their cellular effects by targeting the same molecule.

If trapoxin and trichostatin induce cell cycle arrest by directly inhibiting histone deacetylase, then the binding and enzymatic activities should copurify. To investigate this possibility, we fractioned nuclear thymus proteins by ammonium sulfate precipitation and Mono Q anion exchange chromatography.

Briefly, thymocytes (~12 g) prepared from fresh bovine thymus were homogenized in hypotonic lysis buffer [20 mM tris (pH 7.8), 20 mM NaCl, 1 mM EDTA, 10% glycerol, 1 mM PMSF, 1 mM benzamidine, 10 μg/ml each of pepstatin, aprotinin, and leupeptin] by mechanical disruption and the nuclei were isolated by centrifugation at 3000 g. Nuclei were resuspended in lysis buffer and the proteins were extracted with 0.4 M ammonium sulfate. The viscous lysate was sonicated and clarified by centrifugation at 100,000 g for one hour. Proteins were then precipitated with 90% saturated ammonium sulfate and recovered by centrifugation (100,000 g, one hour). After through dialysis against Q buffer (25 mM tris pH 8, 10 mM NH Cl, 0.25 mM EDTA, 10% glycerol), a portion of the nuclear proteins (~12 mg total protein) was loaded onto a HR 10/10 Mono Q column (Pharmacia). The column was washed with 25 ml Q buffer and eluted with a 50 ml linear gradient of 10 to 500 mM $NH_4Cl$. The column was further washed with 25 ml 500 mM $NH_4$ and 25 ml 1 M histone deacetylase activities or further purified with the K-trap affinity matrix. All procedures were done at 4° C.

Figure 1B:
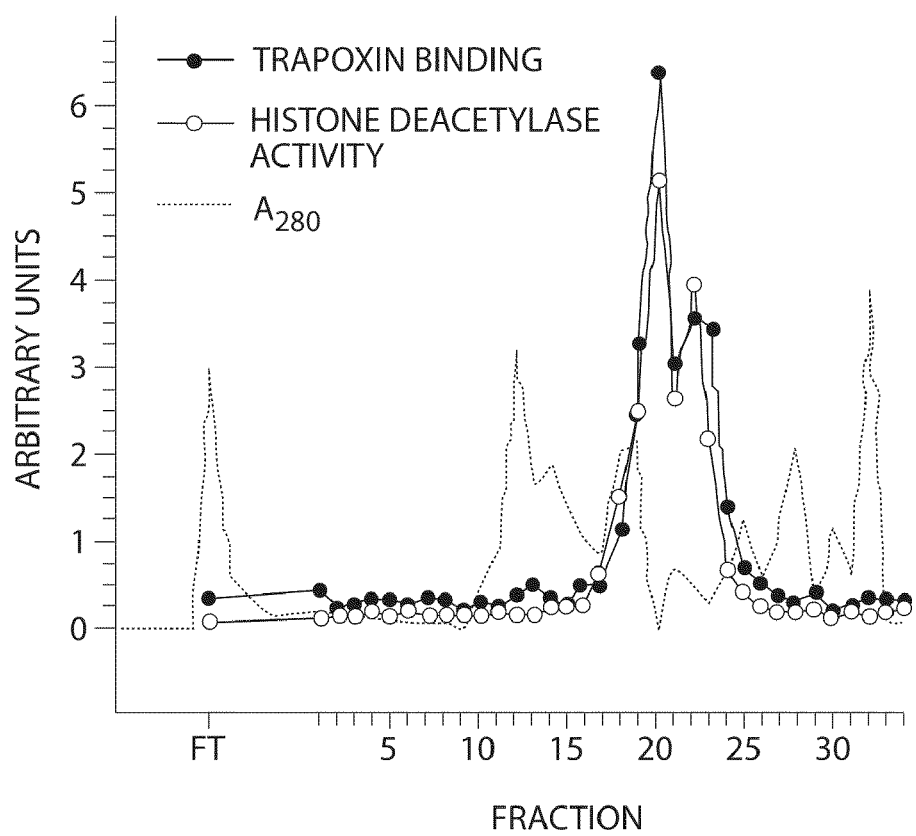
FIG. 1B illustrates the copurification of trapoxin binding and histone deacetylase activities. Nuclear proteins from bovine thymus were precipitated with ammonium sulfate and fractionated on a Mono Q column. Trapoxin binding was assayed by charcoal precipitation with [$^3$H]trapoxin. For the histone deacetylase assay, a peptide corresponding to bovine histone H4 (1-24) was synthesized. The peptide was chemically acetylated with sodium [$^3$H]acetate (5.3 Ci/mmol, New England Nuclear)/BOP reagent (Aldrich) and purified by reverse phase HPLC. Two microliters of [$^3$H]peptide (~40,000 dpm) were used per 200 µo assay. After incubation at 37° C. for one hour, the reaction was quenched with 1 M HCl/0.16 M acetic acid (50 µl). Released [$^3$H]acetic acid was extracted with 600 µl of ethyl acetate and quantified by scintillation counting. Pretreatment of crude or partially purified enzyme with trapoxin or trichostatin (20 nM) for 30 min. at 4° C. abolished deacetylase activity. A$_{280}$=absorbance at 280 n.

Two peaks of histone deacetylase activity eluted from the Mono Q column between 250 and 350 mM $NH_4Cl$ (FIG. 1B). Trapoxin binding activity, as revealed by the charcoal precipitation assay (40 nM [$^3H$]trapoxin), precisely coeluted with the histone deacetylase peaks. Furthermore, all detectable histone deacetylase activity was abolished by treatment with either trapoxin or trichostatin (20 nM). Similar results were obtained with Mono Q fractioned nuclear extracts prepared form human Jurkat T cells.

To purify the histone deacetylase further, we synthesized an affinity matrix based on the trapoxin structure. Because trapoxin itself is not amenable to derivatization and the epoxyketone side chain is indispensable for activity, we chose to replace one of the phenylalanine residues of trapoxin's cyclic core with a lysine that could then be covalently linked to a solid support. This molecule, which we call K-trap, was prepared by a twenty step synthesis starting with commercially available (R)-proline and (S,S)-threitol acetonide (FIG. 2A) (see Example 3). Synthetic K-trap inhibited [$^3H$]thymidine incorporation in MG-63 human osteosarcoma cells with a potency approximately one tenth that of trapoxin. In vitro histone deacetylase activity was also inhibited potently by this compound (complete inactivation at 20 nM) (8).

Figure 2A:
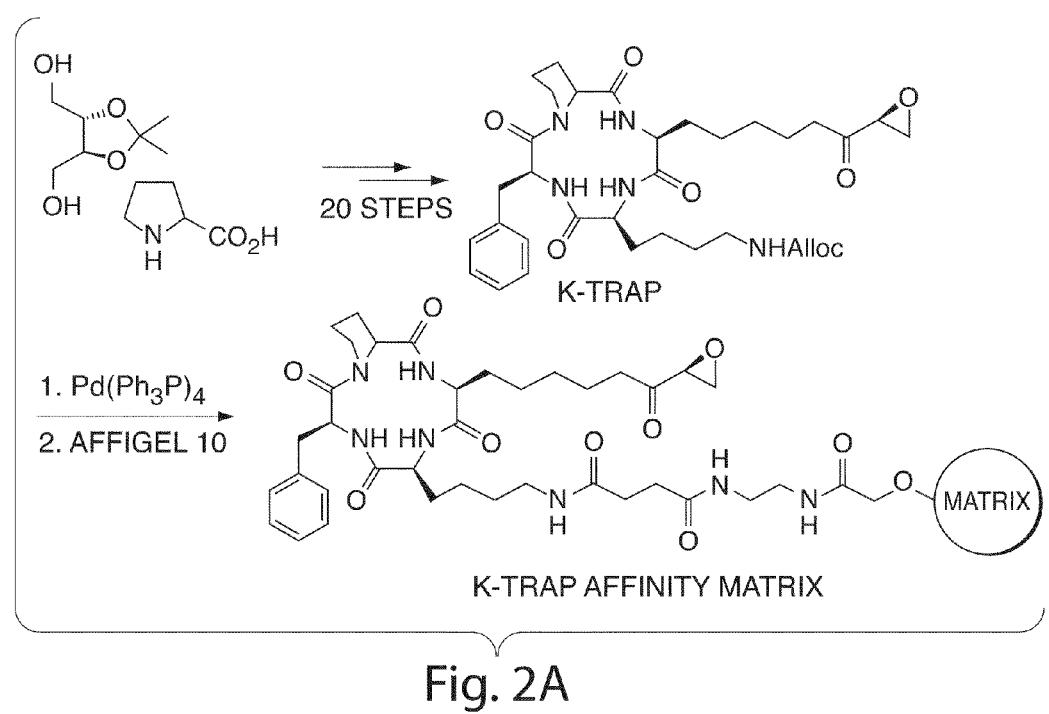
FIG. 2A shows the synthesis of K-trap and the K-trap affinity matrix. K-trap contains a protected lysine residue in place of the phenylalanine at position two in trapoxin. Alloc=allyloxycarbonyl.

K-trap was deprotected with Pd(Ph$_3$P)$_4$ and coupled to an activated agarose matrix (FIG. 2A). Mono Q fractions containing nuclear proteins from bovine thymus were incubated with the K-trap affinity matrix and then tested for both trapoxin binding and histone deacetylase activity. Both activities were depleted (90%) by treatment with the K-trap matrix, yet a control matrix capped with ethanolamine had no effect on either activity (8). Bound polypeptides were eluted by boiling the matrix in 1% SDS buffer and separated b polyacrylamide gel electrophoresis. In vitro binding experiments with soluble [$^3H$]trapoxin indicated that the radiolabel is released into solution following protein denaturation with SDS or guanidinium hydrochloride. Thus, trapoxin binding proteins were expected to elute from the affinity matrix with SDS.

Figure 2B:
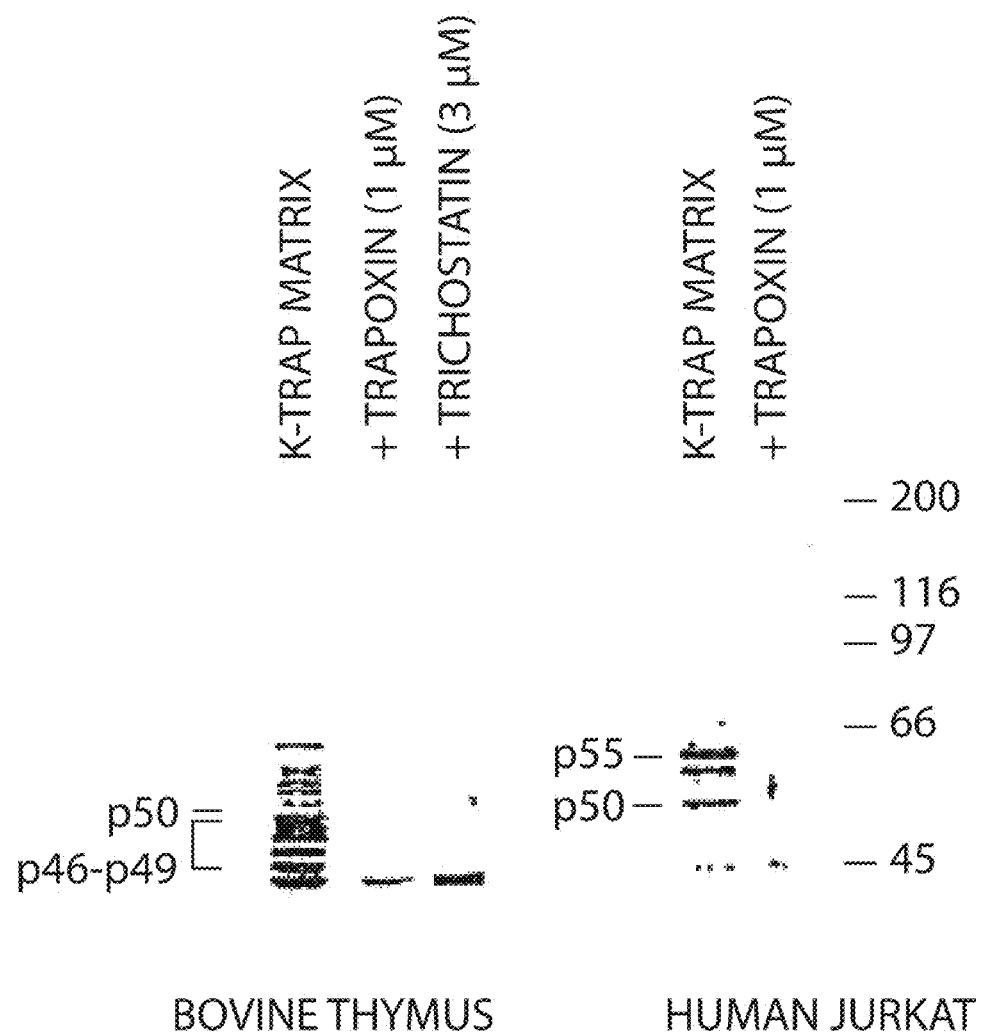
FIG. 2B is a silver stained gel showing bovine and human trapoxin binding proteins. Proteins bound to the K-trap affinity matrix in the presence or absence of trapoxin or trichostatin were eluted by boiling in SDS loading buffer and analyzed by SDS-PAGE (9% gel). Nuclear proteins from human Jurkat T cells were prepared identically to those from bovine thymus (FIG. 1B). Molecular size standards (in kilodaltons) are indicated to the right.

The silver stained gel of the affinity matrix eluates revealed six major polypeptides with apparent molecular sizes between 45 and 50 kD (FIG. 2B). The interaction between bovine p46-p50 and the K-trap matrix appeared to be specific, because these proteins were not retained when the incubation was done in the presence of either trapoxin or trichostatin (FIG. 2B), nor were they structurally unrelated histone deacetylase inhibitor, trichostatin, to prevent p46-p50 from binding to the K-trap matrix implies that one or more of these polypeptides constitute the biologically relevant protein target of both trapoxin and trichostatin. When the affinity purification was repeated with Jurkat nuclear extracts, only two major bands, p50 and p55, were observed by silver staining (FIG. 2B). Recovery of human p50 and p55 was similarly abolished by trapoxin (FIG. 2B) and trichostatin (8). Because the relative intensities of bovine p46-p49 vary with each protein preparation, we suspect that they are proteolytic fragments derived from the bovine equivalent of human p55. One of the bands (p50) is common to both human and bovine sources.

Large scale purification of the bovine proteins led to the resolution of two major bands of ~46 and ~50 kD in the final preparative electrophoresis step, both of which were submitted for microsequencing.

To obtain enough trapoxin binding protein for microsequencing, nuclear ammonium sulfate pellets from 15 bovine thymuses were prepared as described above. Sedimented proteins were resuspended in and dialyzed against buffer A [20 mM bistris (pH 7.2), 20 mM NaCl, 10% glycerol] for 12 hours, and brought to pH 5.8 by dialyzing against bugger A (pH 5.8) for 30 minutes. After centrifugation, the dialysate (~650 mg protein) was loaded onto a Q Sepharose FF column (2.6×10 cm; Pharmacia) and the column was washed with 120 ml buffer A (pH 5.8). Proteins wee eluted with a 400 ml linear gradient of 20 to 600 mM NaCl in buffer A. Fractions (10 ml; each fraction contained 1 ml of 1 M tris pH 8 to neutralize the acidic buffer A) were assayed for trapoxin binding activity. Tween-20 was added to active fractions at a final concentration of 0.05%, and these fractions were incubated with K-trap affinity matrix for 16 hours (25 μl per ml Q fraction). After washing the matrix three times with phosphate buffered saline, bound proteins were eluted by boiling in 40 μl of SDS sample buffer per 25 μl of matrix. SDS eluates were combined and the proteins resolved by SDS-PVDF membrane (Biorad). Staining with Ponceau S revealed two major bands (46 and 50 kD). The excised bands were proteolytically digested and the HPLC purified peptide fragments were sequenced at the Harvard Microchemistry Facility.

The bovine protein of larger molecular size (~50 kD) corresponds to a known protein, RbAp48 (11), that consists of seven WD repeat domains (12). Originally identified as a protein that binds to the retinoblastoma gene product (pRb), RbAp48 may constitute an adaptor subunit that targets the histone deacetylase to specific chromatin domains.

The ~46 kD bovine protein is highly related to the protein encoded by the yeast RPD3 gene, which has been implicated by several genetic screens as a transcriptional regulator, but whose biochemical function is unknown (13). Partial cDNA sequences for the human gene were identified in the expressed sequence tag database (dbEST) and were used to design polymerase chain reaction (PCR) primers. Briefly, after noting sequence similarity between peptides derived from the purified bovine trapoxin binding protein and yeast RPD3, we checked dbEST to see whether any partial sequences for the human homologue had been reported. Two ESTs (Genbank accession numbers: D31480 and F07807) were identified whose predicted translation products aligned with high sequence similarity to $NH_2$- and COOH-terminal regions of HD1, respectively. PCR primers were designed based on these tags and a one kilobase PCR product was obtained from a Jurkat cDNA library (Stratagene). A $^{32}P$ labeled probe prepared by random priming was used to screen the Jurkat library, and ten positive clones were isolated. One of the clones was fully sequenced and found to contain a putative full-length open reading frame (FIG. 3A). The peptide sequences obtained from the purified bovine protein align with 100% identity to sequences deduced from this coding region (FIG. 3A, boxed residues). We call this human protein HD1 (for histone deacetylase), and its predicted size of 55 kD agrees well with the estimated size of p55 isolated from Jurkat nuclear extracts using the K-trap affinity matrix (FIG. 2B). A dbEST search indicated the existence of at least two other related human genes.

Figure 3B:
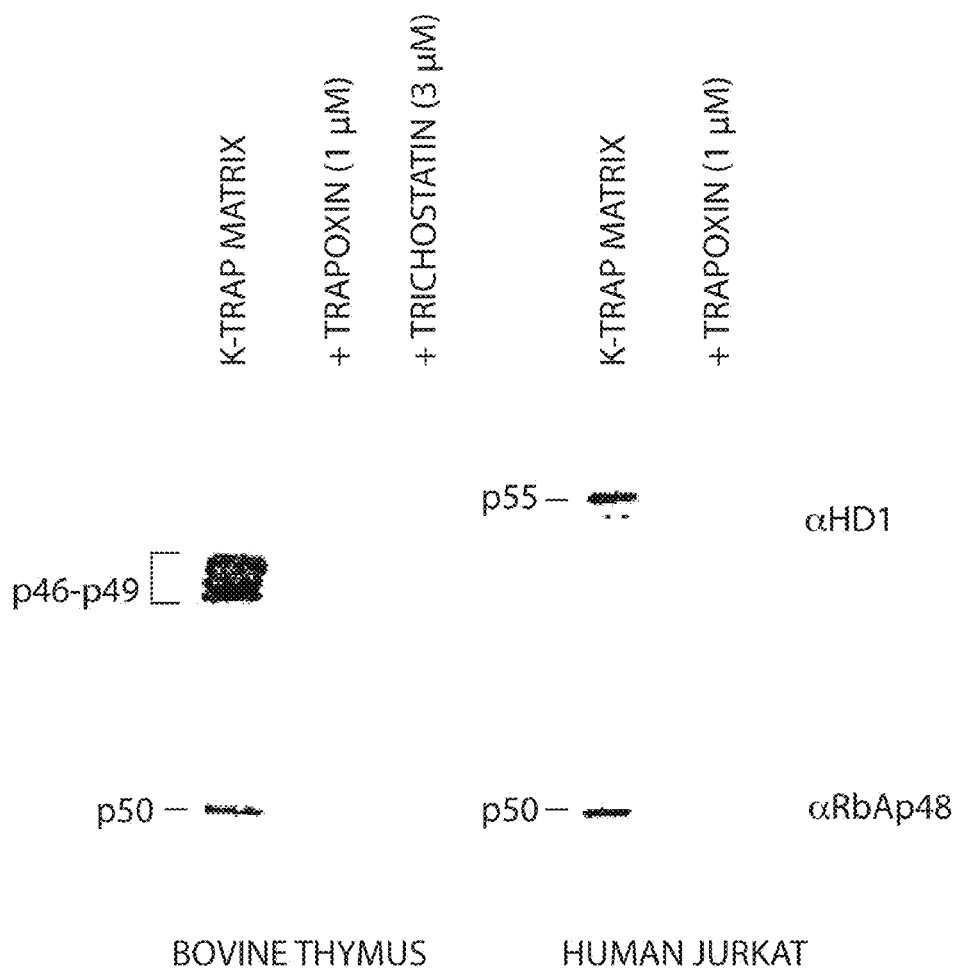
FIG. 3B is a protein immunoblot analogous to the silver stained gel in FIG. 2B, showing the relationship between bovine p46-49 and human p55 (top panels) and confirming the identity of p50 (bovine and human) as RbAp48 (bottom panels). Proteins eluted from the K-trap affinity matrix (FIG. 2) were separated by SDS-PAGE and transferred to Immobilon-P (Millipore). Blots were probed with polyclonal anti-HD1 (319-336) or monoclonal anti-RbAp48 and bound antibodies were detected with enhanced chemiluminescence (Amersham).

To determine the relationship between the proteins from bovine thymus (p46-p50) and the proteins isolated from human Jurkat T cells (p50 and p55), an antiserum was generated against a peptide specified by the HD1 open reading frame (FIG. 3A, amino acids 319 to 334). Immunoblot analysis of the bovine proteins p46-p49 and the human protein p55 showed that they all react with the antiserum and provides additional evidence that these bands correspond to bovine and human HD1 (FIG. 3B). A monoclonal antibody that specifically recognizes RbAp48 was used to confirm the identity of bovine and hum p50. Importantly, neither HD1 nor RbAp48 was detected when the affinity purification was done in the presence of trapoxin or trichostatin (FIG. 3B).

Figure 4A:
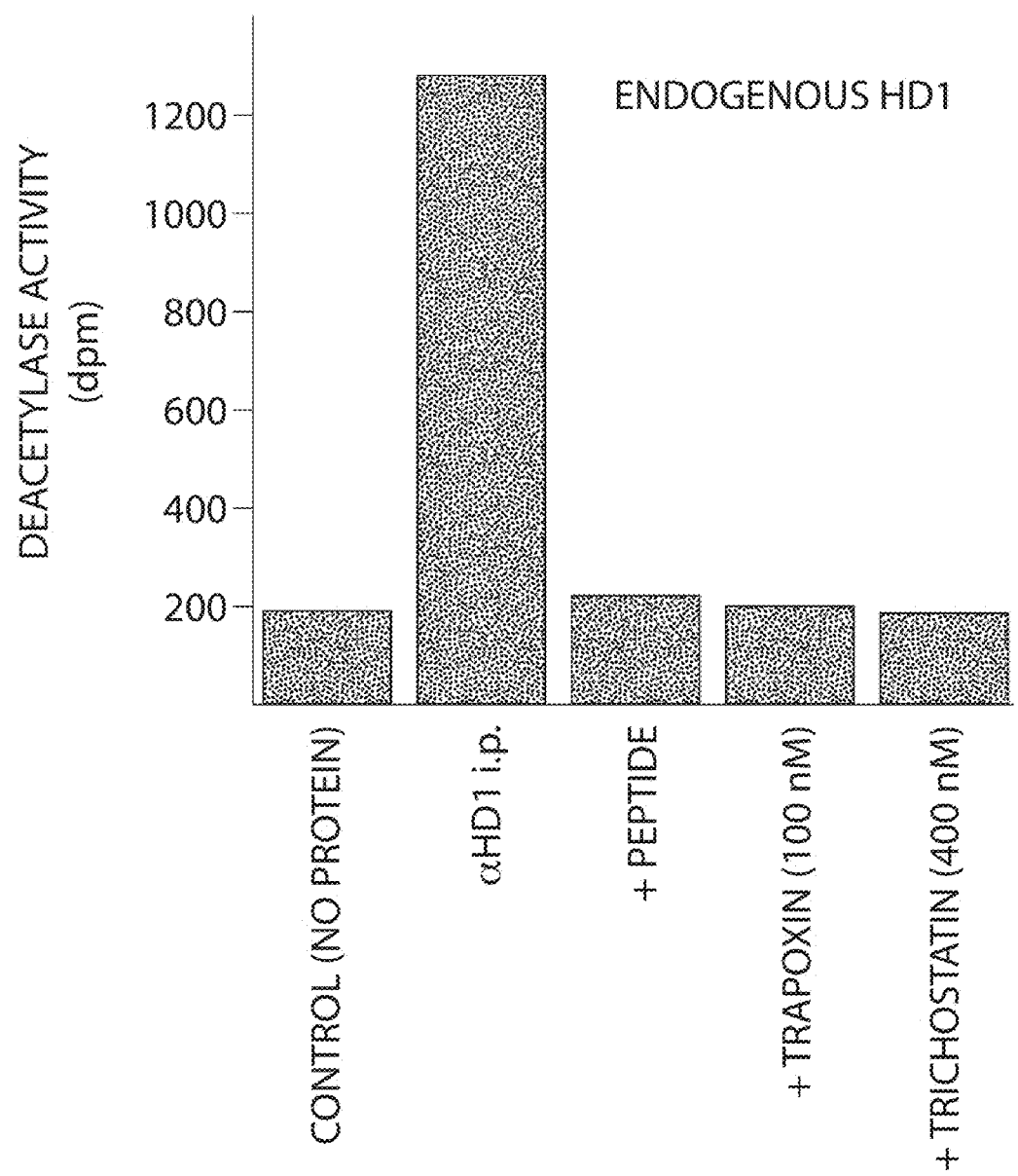
FIG. 4A is an immunoprecipation of endogenous histone deacetylase activity with affinity purified anti-HD1(467-482) antibodies. Anti-HD1(467-482) immunoprecipitates from equivalent amounts of Jurkat nuclear extract (1 mg nuclear protein supplemented with 0.5 M NaCl, 1% BSA, and 0.1% NP-40) were isolated in the presence or absence of HD1(467-482) peptide competitor. After resuspending the immunoprecipitates in HDx buffer [20 mM tris (pH 8), 150 mM NaCl, 10% glycerol], inhibitors were added as indicated, and histone deacetylase activity was measured as described in FIG. 1A.

We used affinity purified antibodies directed against a COON-terminal peptide (amino acids 467 to 482) to immunoprecipitate HD1 from crude nuclear extracts. The immunoprecipitates contained histone deacetylase activity that was inhibited by both trapoxin and trichostatin (FIG. 4A). Consistent with the idea that HD1 and RbAp48 form a complex in vivo, the two proteins coprecipitated with the anti-DH1 antibodies (FIG. 4B). Neither HD1, RbAp48, nor the associated histone deacetylase activity were immunoprecipitated in the presence of the HD1 COOH-terminal peptide (FIGS. 4A and 4B) (15). HD1, like RbAp48 (11), is detected predominantly in the nucleus by immunostaining with the aforementioned antibodies (8). Given that HD1 and RbAp48 are the major proteins eluted from the K-trap matrix (FIG. 2B), it is likely that they interact directly with one another.

Figure 4C:
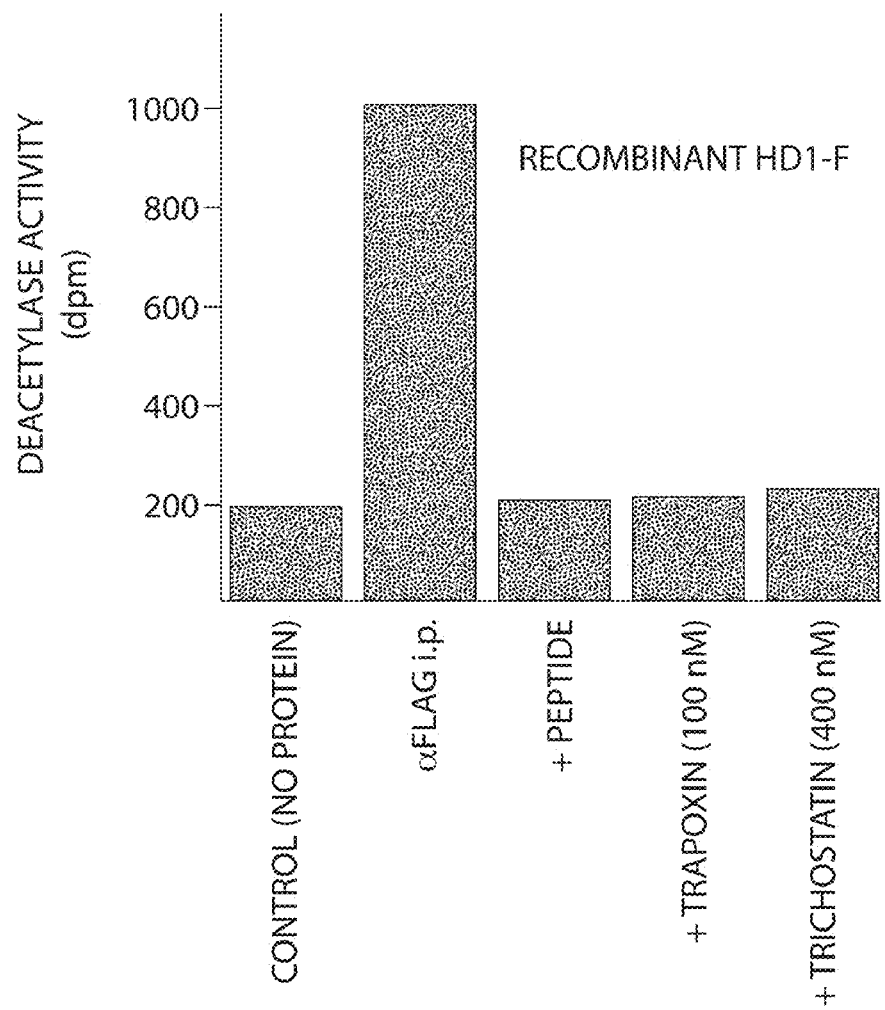
FIG. 4C demonstrates the histone deacetylase activity of recombinant HD1-F. Tag Jurkat cells (Clipstone et al. (1992) *Nature* 357, 695-7) were transfected with pFJ5 (vector alone) or pBJ5/HD1-F (encoding COOH-terminal FLAG epitope tagged HD1) by electroporation and detergent lysates were prepared [0.5% Triton X-100, 50 mM tris (pH 8), 100 mM NaCl, 10% glycerol]. Anti-FLAG antibodies conjugated to agarose beads (IBI) were used to immunoprecipitate recombinant HD1 in the presence or absence of FLAG peptide competitor, and histone deacetylase activity was measured as described above.
Figure 4D:
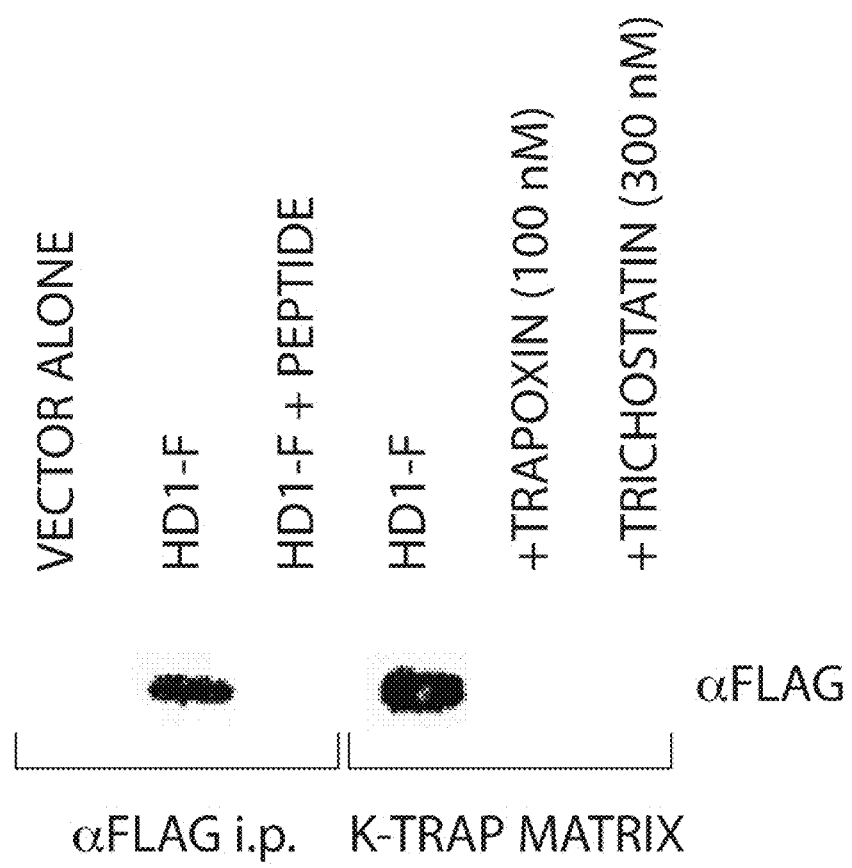
FIG. 4D shows the interaction between recombinant HD1-F and the K-trap affinity matrix. Lysates from Jurkat cells transfected with pBJ5/HD1-F were incubated with the K-trap affinity matrix in the presence or absence of inhibitors. Immunoblots of the eluted proteins were probed with the anti-FLAG M2 monoclonal antibody (IBI).

We extended the results obtained with the endogenous protein by expressing recombinant FLAG epitope tagged HD1 (HD1-F) in Jurkat T cells. Anti-FLAG immunoprecipitates from cells transfected with pBJ5/HD1-F contained histone deacetylase activity that was sensitive to both trapoxin and trichostatin (FIG. 4C). Histone deacetylase activity was not precipitated when the antibody was blocked with excess FLAG peptide (15). Interestingly, endogenous RbAp48 did not coprecipitate with overexpressed HD1-F (8), demonstrating that RbAp48 is not required for either histone deacetylase or trapoxin binding activity. The result is consistent with the idea that RbAp48 serves a targeting rather than an enzymatic function. Finally, lysates from cells transfected with pBJ5/HD1-F were incubated with the K-trap affinity matrix in the presence or absence of trapoxin and trichostatin. Protein immunoblot analysis demonstrated an interaction between recombinant HD1-F and the K-trap affinity matrix that was fully competed by nanomolar concentrations of trapoxin or trichostatin (FIG. 4D).

HD1 is 60% identical to the protein encoded by the yeast RPD3 gene, which was isolated in four independent mutant suppressor screens designed to identify transcriptional repressors (13, 16, 17, 18, 19). No biochemical function for the yeast protein has previously been postulated. A negative regulator of the TRK2 gene, RPD3 is necessary for the transcriptional repression of several genes whose expression is regulated according to specific environmental conditions. Loss of RPD3 also leads to decreased transcriptional activation of certain genes, but this effect may be indirect (13, 17). Although RPD3 had yet to be implicated in silencing at telomeres or the mating loci, the fact that silencing is eliminated by point mutations in specific lysine residues near the $NH_2$-terminus of histones H3 and H4 suggests that lysine deacetylation may contribute to the maintenance of silenced chromatin (20, 21, 22, 23). Indeed, silencing at telomeres and the mating loci has been correlated with the presence of hypoacetylated histones, and sir mutants which are defective in silencing show a corresponding increase in the extent of histone acetylation at these loci (24). The SIR3 and SIR4 proteins have been shown to interact with a bacterially expressed histone H4 $NH_2$-terminal domain in vitro (25), and it is possible that deacetylation of one or more lysine residues is required for this interaction in vivo. Our results further support a role for histone deacetylase as a transcriptional regulator and establish a biochemical connection to the genetic studies that originally characterized RPD3.

How does inhibition of histone deacetylase in mammalian cells lead to $G_1$ and $G_2$ phase cell cycle arrest? One possibility is that specific cell cycle regulatory proteins such as the cyclin dependent kinase inhibitors are transcriptionally upregulated in response to histone deacetylase inactivation. Alternatively, cell cycle checkpoints may exist that monitor histone acetylation or higher-order chromatin structure. It should now be possible to study the regulation of histone deacetylase during the cell cycle, its substrate specificity, and the mechanism by which it is targeted to specific regions of the genome.

Example 2

Figure 8A:
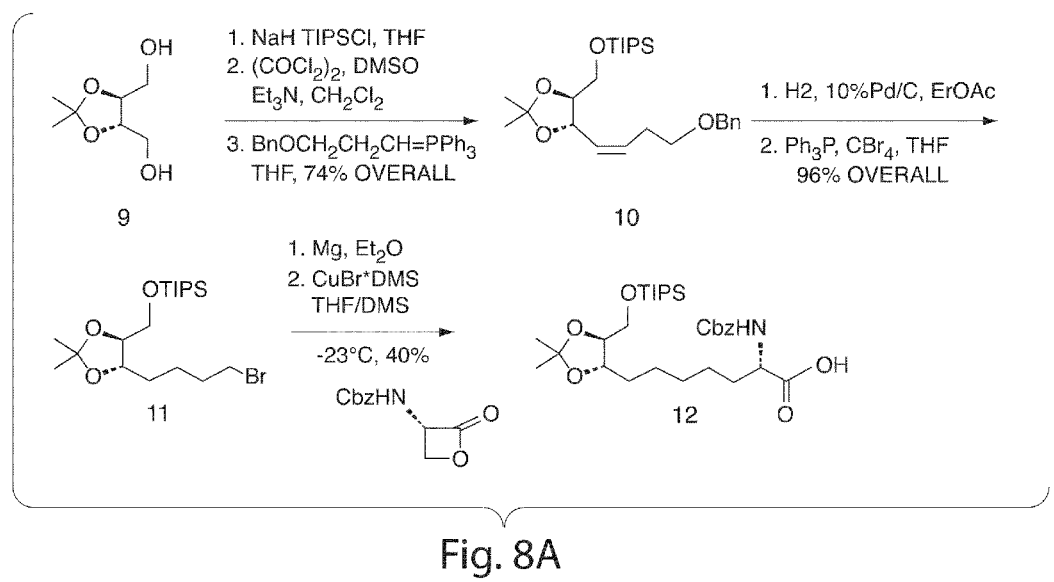
FIGS. 8A-8C illustrate a synthesis of tritiated Trapoxin B.
Figure 8B:
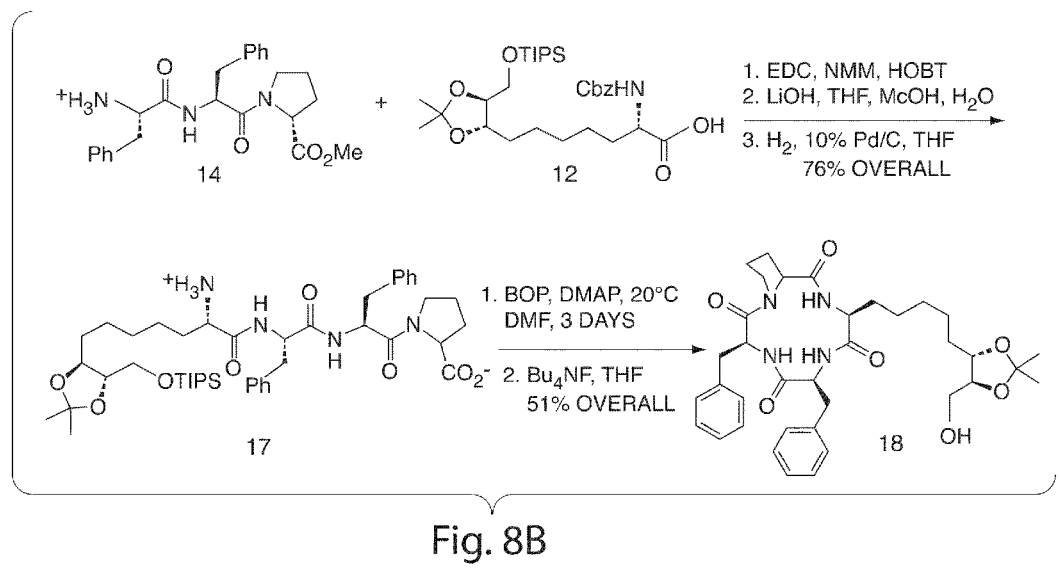
Figure 8C:
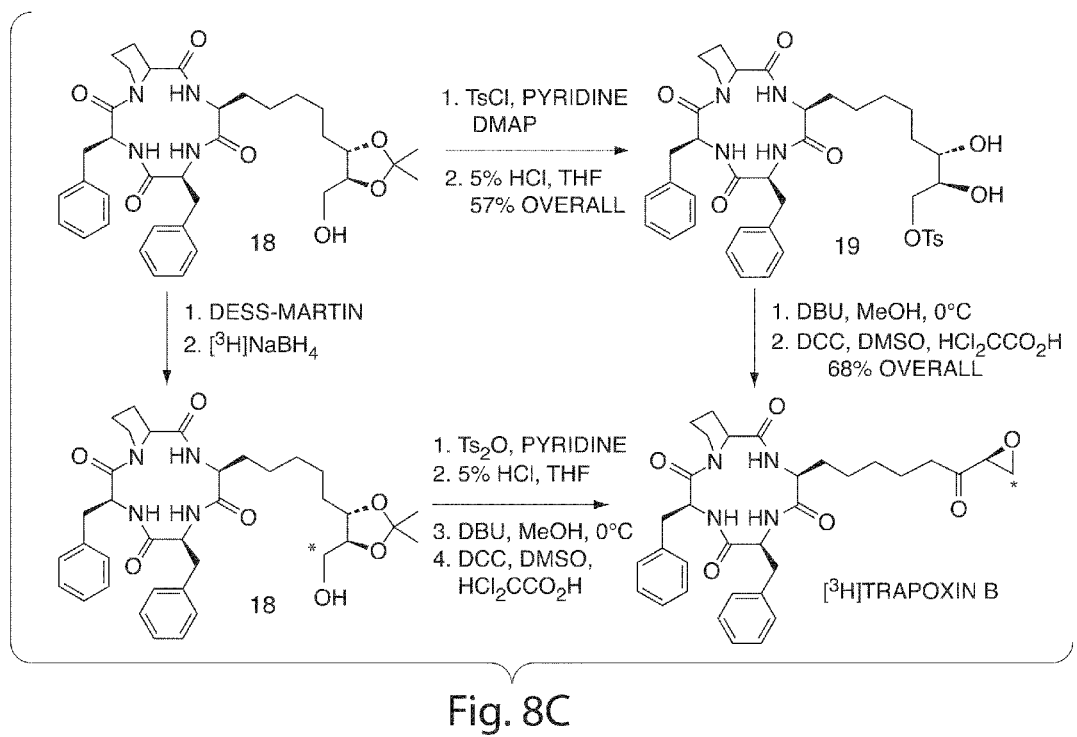

3H-Trapoxin was Prepared from (S,S)-Threitol Acetonide (9) by Total Synthesis, as Outlined in FIGS. 8A-8C As shown in FIG. 8A, (S,S)-threitol acetonide (9) was monoprotected by treatment with triisopropylsilylchloride (TIPSCl) and sodium hydride in tetrahydrofuran (THF). The free alcohol was then subjected to Swern oxidation. Wittig reaction of the resulting aldehyde gave compound 10 in good yield for the three steps. Compound 10 was then hydrogenated with deprotection of the primary alcohol, which was then converted to the bromide 11 in excellent yield. Bromide 11 was converted to the organocuprate and reacted with (S)-serine β-lactone to yield the benzyloxycarbonyl- (Cbz) protected amino acid 12.

As shown in FIG. 8B, 12 was coupled to tripeptide methyl ester 14, and the methyl ester was saponified. The amino acid was then cyclized and the silyl protecting group was removed to yield cyclotetrapeptide 18 in 51% yield.

Cyclotetrapeptide 18 was tritiated, as shown in FIG. 8C, by oxidation of the primary alcohol with the Dess-Martin reagent, and the aldehyde was reduced with tritiated sodium borohydride to provide tritiated 18, which was converted to [$^3$H]Trapoxin B by tosylation of the primary alcohol, deprotection of the diol, epoxide ring closure, and oxidation of the secondary alcohol to yield the desired compound. Non-radio-labelled 18 was converted to [$^3$H]Trapoxin B, via tosylate 19, in 68% overall yield.

Example 2

Figure 9A:
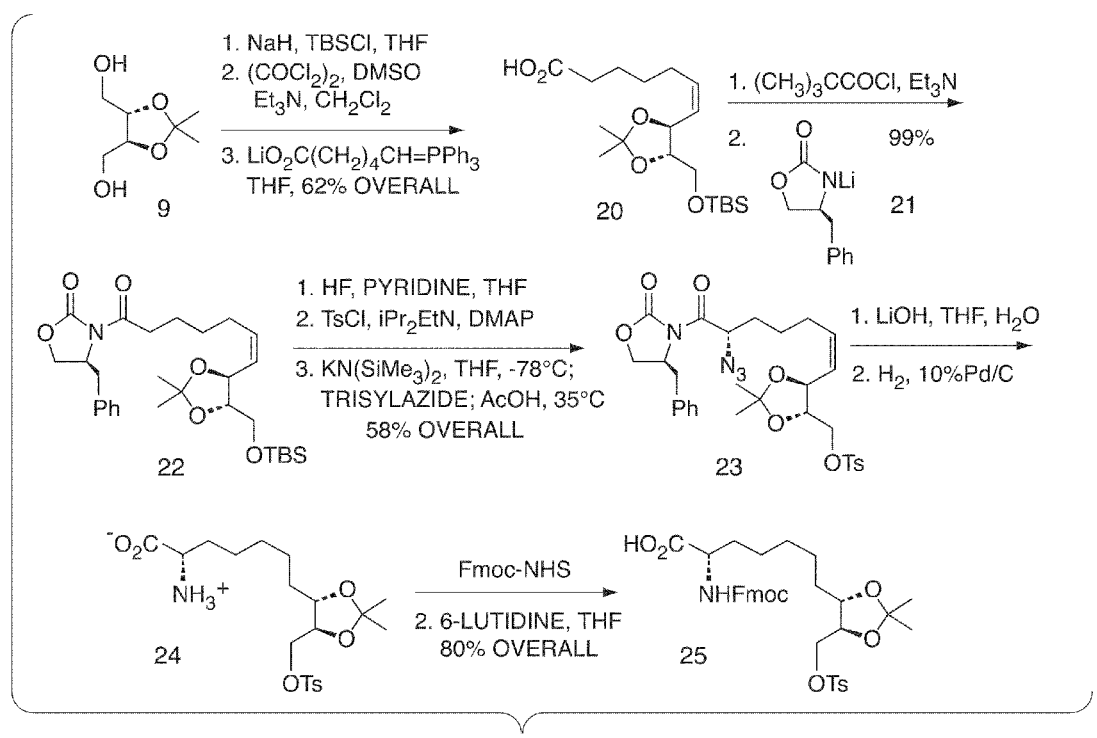
FIGS. 9A-9C depict a synthesis of the K-trap and K-trap affinity matrix.
Figure 9B:
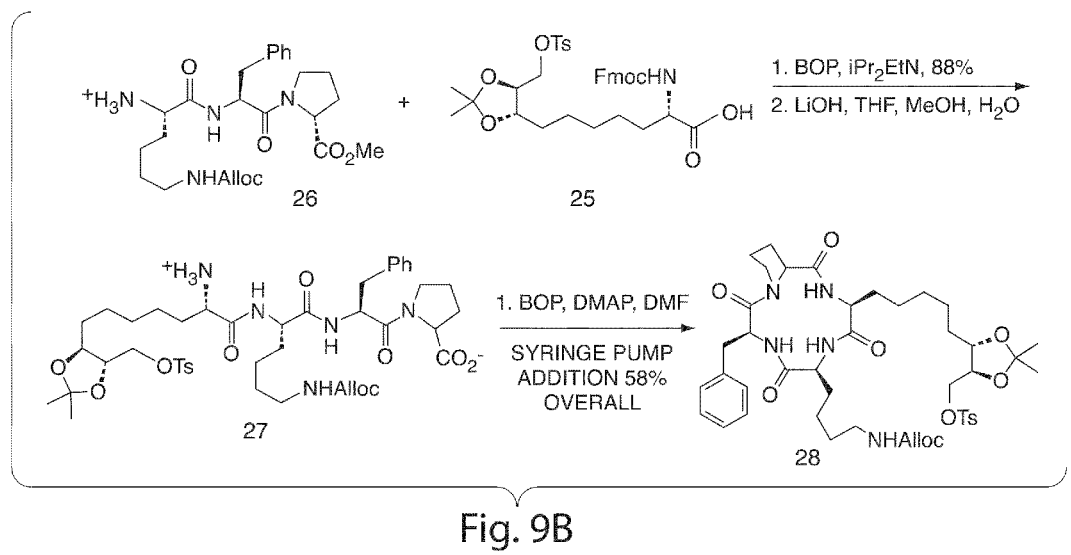
Figure 9C:
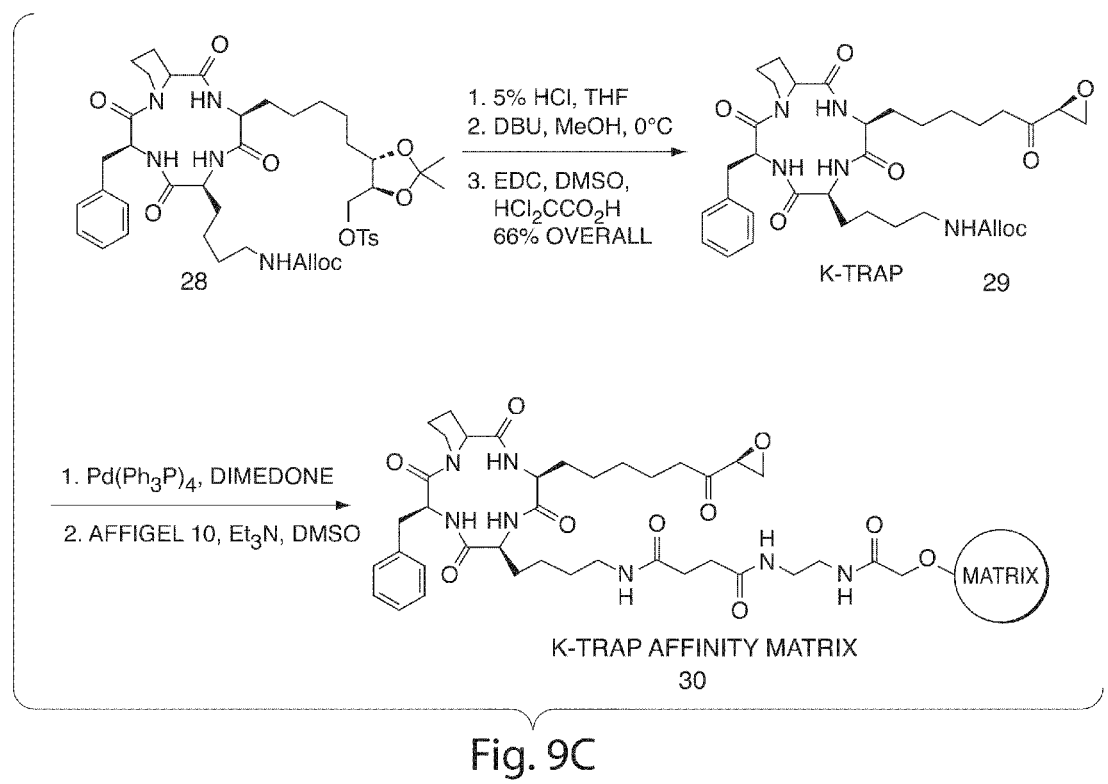

K-Trap was prepared from (S,S)-threitol acetonide (9) by total synthesis, as outlined in FIGS. 9A-9C. As shown in FIG. 9A, monoprotection and Swern oxidation of 9 yielded the aldehyde as above. Wittig homologation yielded carboxylic acid 20, which was converted to the mixed anhydride and treated with lithiated oxazolidinone 21 to provide 22 in excellent yield. Deprotection of the primary alcohol and conversion to the tosylate were followed by treatment of the potassium enolate with trisylazide according to the method of Evans to effect electrophilic azide transfer in good overall yield and stereoselectivity, providing compound 23. Removal of the chiral auxiliary and catalytic reduction of the azido function, with hydrogenation of the olefin, provided amino acid 24, which was N-protected to give the Fmoc derivative 25 in high overall yield.

Referring to FIG. 9B, protected amino acid 25 was coupled to tripeptide methyl ester 26. The methyl ester was saponified to yield 27, which was cyclized under high-dilution conditions to provide cyclotetrapeptide 28 in 58% yield.

As shown in FIG. 9C, compound 28 was converted to K-trap (29) by deprotection of the diol, base-promoted epoxide closure, and oxidation of the secondary alcohol to provide K-trap (29) in good overall yield. The K-trap affinity matrix 30 was provided by palladium-catalyzed removal of the allyloxycarbonyl (Alloc) group from the lysine residue of 29, and immobilization on Affigel 10.

References and Notes.
1. B. M. Turner, Cell 75, 5-8 (1993).
2. D. Y. Lee, J. J. Hayes, D. Pruss, A. P. Wolffe, Cell 72, 73-84 (1993)
3. S. Kelff, E. D Andrulis, C. W. Anderson, R. Sternglanz, J. Biol. Chem. 270, 24674-24677 (1995).
4. M. Yoshida, S. Horinouchi, T. Beppu, Bioessays 17, 423-30 (1995)
5. M. Kijima, M. Yoshida, K. Sugita, S. Horinouchi, T. Beppu, J. Biol. Chem. 268, 22429-35 (1993).
6. J. Tauton, J. L. Collins, S. L. Schreiber manuscript in preparation.
8. J. Taunton, C. A. Hassig, S. L. Schreiber, unpublished results.
11. Y. W. Qian, et al., Nature 364, 648-52 (1993).
12. E. J. Neer, C. J. Schmidt, R. Nambudripad, T. F. Smith, Nature 371, 297-300 (1994).
13. M. Vidal, R. F. Gaber, Mol. Cell. Biol. 11, 6317-27 (1991).
15. Control experiments indicated that competitor peptides had no effect on histone deacetylase activity per se.
16. K. Nasmuth, D. J. Stillman, D. Kipling, Cell 48, 579-87 (1987).
17. D. J. Stillman, S. Dorland, Y. Yu, Genetics 136, 781-8 (1994).
18. E. A. McKenzie, et al., Mol. Gen. Genet. 240, 374-86 (1993).
19. K. S. Bowdish, A. P. Mitchell, Mol. Cell. Biol. 13, 2172-81 (1993).
20. L. M. Johnson, P. S. Kayne, E. S. Kahn, M. Grunstein, Proc. Natl. Acad. Sci. U.S.A. 87, 6286-90 (1990).
21. P. C. Megee, B. A. Morgan, B. A. Mittman, M. M. Smith, Science 247, 841-5 (1990).
22. E. C. Park, J. W. Szostak, Mol. Cell. Biol. 10, 4932-4 (1990).
23. O. M. Aparicio, B. L. Billington, D. E. Gottschling, Cell 66, 1279-87 (1991).
24. M. Braunstein, A. B. Rose, S. G. Holmes, C. D. Allis, J. R. Borach, Genes Dev. 7, 592-604 (1993).
25. A. Hecht, T. Laroche, S. Strahl Bolsinger, S. M. Gasser, M. Grunstein, Cell 80, 583-92 (1995).
26. N. A. Clipstone, G. R. Crabtree, Nature 357, 695-7 (1992).

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

What is claimed is:

1. A method for inhibiting a histone deacetylase in a subject, comprising administering to the subject a pharmaceutically acceptable composition comprising a therapeutically effective amount of a compound represented by the general formula A-B-C, or a pharmaceutically acceptable salt thereof, formulated together with one or more pharmaceutically acceptable carriers or diluents,
wherein:

A is

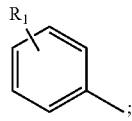

$R_1$ is an alkyl group substituted by one or more moieties selected from the group consisting of halogen, hydroxyl, carboxylate, alkoxycarbonyl, aryloxycarbonyl, alkylcarbonyl, arylcarbonyl, aldehyde, thiocarbonyl, alkoxyl, unsubstituted amino, monosubstituted amino, disubstituted amino, amido, amidine, imine, nitro, azido, sulfhydryl, alkylthio, cyano, trifluoromethyl, sulfonato, sulfamoyl, sulfonamido, heterocyclyl, aralkyl, aromatic, and heteroaromatic moieties;

B is a substituted or unsubstituted $C_2$-$C_8$ alkenylidene; and

C is

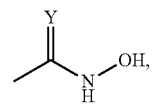

wherein Y is O.

2. The method of claim 1, wherein the compound is administered in an amount effective for inhibiting proliferation of a cell in the subject.

3. A method for treating a subject with leukemia or lymphoma, comprising administering to the subject with leukemia or lymphoma a therapeutically effective amount of a compound of the formula A-B-C, or a pharmaceutically acceptable salt thereof,
wherein:

A is

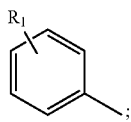

$R_1$ is an alkyl group substituted by one or more moieties selected from the group consisting of halogen, hydroxyl, carboxylate, alkoxycarbonyl, aryloxycarbonyl, alkylcarbonyl, arylcarbonyl, aldehyde, thiocarbonyl, alkoxyl, unsubstituted amino, monosubstituted amino, disubstituted amino, amido, amidine, imine, nitro, azido, sulfhydryl, alkylthio, cyano, trifluoromethyl, sulfonato, sulfamoyl, sulfonamido, heterocyclyl, aralkyl, aromatic, and heteroaromatic moieties;

B is a substituted or unsubstituted $C_2$-$C_8$ alkenylidene; and C is

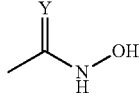

wherein Y is O.

4. The method of claim 1, wherein B is a substituted or unsubstituted $C_2$ alkenylidene.

5. The method of claim 1, wherein B is an unsubstituted $C_2$ alkenylidene.

6. The method of claim 3, wherein B is a substituted or unsubstituted $C_2$ alkenylidene.

7. The method of claim 3, wherein B is an unsubstituted $C_2$ alkenylidene.

8. The method of claim 1, wherein the compound is of the formula:

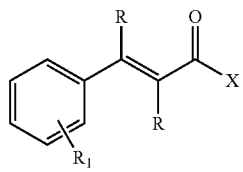

or a pharmaceutically acceptable salt thereof,
wherein:
$R_1$ is an alkyl group substituted by one or more moieties selected from the group consisting of halogen, hydroxyl, carboxylate, alkoxycarbonyl, aryloxycarbonyl, alkylcarbonyl, arylcarbonyl, aldehyde, thiocarbonyl, alkoxyl, unsubstituted amino, monosubstituted amino, disubstituted amino, amido, amidine, imine, nitro, azido, sulfhydryl, alkylthio, cyano, trifluoromethyl, sulfonato, sulfamoyl, sulfonamido, heterocyclyl, aralkyl, aromatic, and heteroaromatic moieties;

each R is independently selected from the group consisting of hydrogen, substituted and unsubstituted alkyl, substituted and unsubstituted alkenyl, substituted and unsubstituted alkynyl, substituted and unsubstituted aryl, substituted and unsubstituted aralkyl, substituted and unsubstituted heterocyclyl, halogen, hydroxyl, carboxylate, alkoxycarbonyl, aryloxycarbonyl, alkylcarbonyl, arylcarbonyl, aldehyde, thiocarbonyl, alkoxyl, unsubstituted amino, monosubstituted amino, disubstituted amino, amido, amidine, imine, nitro, azido, sulfhydryl, alkylthio, cyano, trifluoromethyl, sulfonato, sulfamoyl, and sulfonamido;
and

represents a group of the formula

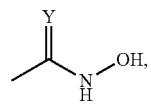

wherein Y is O.

9. The method of claim 8, wherein R is H.

10. The method of claim 3, wherein the compound is of the formula:

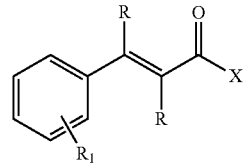

or a pharmaceutically acceptable salt thereof,
wherein:
$R_1$ is an alkyl group substituted by one or more moieties selected from the group consisting of halogen, hydroxyl, carboxylate, alkoxycarbonyl, aryloxycarbonyl, alkylcarbonyl, arylcarbonyl, aldehyde, thiocarbonyl, alkoxyl, unsubstituted amino, monosubstituted amino, disubstituted amino, amido, amidine, imine, nitro, azido, sulfhydryl, alkylthio, cyano, trifluoromethyl, sulfonato, sulfamoyl, sulfonamido, heterocyclyl, aralkyl, aromatic, and heteroaromatic moieties;

each R is independently selected from the group consisting of hydrogen, substituted and unsubstituted alkyl, substituted and unsubstituted alkenyl, substituted and unsubstituted alkynyl, substituted and unsubstituted aryl, substituted and unsubstituted aralkyl, substituted and unsubstituted heterocyclyl, halogen, hydroxyl, carboxylate, alkoxycarbonyl, aryloxycarbonyl, alkylcarbonyl, arylcarbonyl, aldehyde, thiocarbonyl, alkoxyl, unsubstituted amino, monosubstituted amino, disubstituted amino, amido, amidine, imine, nitro, azido, sulfhydryl, alkylthio, cyano, trifluoromethyl, sulfonato, sulfamoyl, and sulfonamido;
and

represents a group of the formula

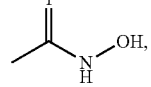

wherein Y is O.

11. The method of claim 10, wherein R is H.

12. The method of claim 3, wherein the subject has leukemia.

13. The method of claim 3, wherein the subject has lymphoma.

* * * * *

UNITED STATES PATENT AND TRADEMARK OFFICE
CERTIFICATE OF CORRECTION

PATENT NO. : 8,362,084 B2
APPLICATION NO. : 13/030086
DATED : January 29, 2013
INVENTOR(S) : Stuart L. Schreiber et al.

It is certified that error appears in the above-identified patent and that said Letters Patent is hereby corrected as shown below:

In the Specification

In column 1, lines 16-20, please delete the following section:

"GOVERNMENT FUNDING

Word described herein was supported in part by funding from the National Institutes of Health. The United States Government has certain rights in the invention."

Signed and Sealed this
Twenty-fourth Day of September, 2013

Teresa Stanek Rea
*Deputy Director of the United States Patent and Trademark Office*

SEQUENCE LISTING

```
<160> NUMBER OF SEQ ID NOS: 23

<210> SEQ ID NO 1
<211> LENGTH: 1449
<212> TYPE: DNA
<213> ORGANISM: Homo sapiens
<220> FEATURE:
<221> NAME/KEY: CDS
<222> LOCATION: (1)..(1446)

<400> SEQUENCE: 1 atg gcg cag acg cag ggc acc cgg agg aaa gtc tgt tac tac tac gac      48
Met Ala Gln Thr Gln Gly Thr Arg Arg Lys Val Cys Tyr Tyr Tyr Asp
1               5                   10                  15 ggg gat gtt gga aat tac tat tat gga caa ggc cac cca atg aag cct      96
Gly Asp Val Gly Asn Tyr Tyr Tyr Gly Gln Gly His Pro Met Lys Pro
            20                  25                  30 cac cga atc cgc atg act cat aat ttg ctg ctc aac tat ggt ctc tac      144
His Arg Ile Arg Met Thr His Asn Leu Leu Leu Asn Tyr Gly Leu Tyr
        35                  40                  45 cga aaa atg gaa atc tat cgc cct cac aaa gcc aat gct gag gag atg      192
Arg Lys Met Glu Ile Tyr Arg Pro His Lys Ala Asn Ala Glu Glu Met
    50                  55                  60 acc aag tac cac agc gat gac tac att aaa ttc ttg cgc tcc atc cgt      240
Thr Lys Tyr His Ser Asp Asp Tyr Ile Lys Phe Leu Arg Ser Ile Arg
```

```
              65                  70                  75                  80
cca gat aac atg tcg gag tac agc aag cag atg cag aga ttc aac gtt      288
Pro Asp Asn Met Ser Glu Tyr Ser Lys Gln Met Gln Arg Phe Asn Val
                        85                  90                  95 ggt gag gac tgt cca gta ttc gat ggc ctg ttt gag ttc tgt cag ttg      336
Gly Glu Asp Cys Pro Val Phe Asp Gly Leu Phe Glu Phe Cys Gln Leu
                100                 105                 110 tct act ggt ggt tct gtg gca agt gct gtg aaa ctt aat aag cag cag      384
Ser Thr Gly Gly Ser Val Ala Ser Ala Val Lys Leu Asn Lys Gln Gln
            115                 120                 125 acg gac atc gct gtg aat tgg gct ggg ggg ctg cac cat gca aag aag      432
Thr Asp Ile Ala Val Asn Trp Ala Gly Gly Leu His His Ala Lys Lys
        130                 135                 140 tcc gag gca tct ggc ttc tgt tac gtc aat gat atc gtc ttg gcc atc      480
Ser Glu Ala Ser Gly Phe Cys Tyr Val Asn Asp Ile Val Leu Ala Ile
145                 150                 155                 160 ctg gaa ctg cta aag tat cac cag agg gtg ctg tac att gac att gat      528
Leu Glu Leu Leu Lys Tyr His Gln Arg Val Leu Tyr Ile Asp Ile Asp
                165                 170                 175 att cac cat ggt gac ggc gtg gaa gag gcc ttc tac acc acg gac cgg      576
Ile His His Gly Asp Gly Val Glu Glu Ala Phe Tyr Thr Thr Asp Arg
                180                 185                 190 gtc atg act gtg tcc ttt cat aag tat gga gag tac ttc cca gga act      624
Val Met Thr Val Ser Phe His Lys Tyr Gly Glu Tyr Phe Pro Gly Thr
            195                 200                 205 ggg gac cta cgg gat atc ggg gct ggc aaa ggc aag tat tat gct gtt      672
Gly Asp Leu Arg Asp Ile Gly Ala Gly Lys Gly Lys Tyr Tyr Ala Val
        210                 215                 220 aac tac ccg ctc cga gac ggg att gat gac gag tcc tat gag gcc att      720
Asn Tyr Pro Leu Arg Asp Gly Ile Asp Asp Glu Ser Tyr Glu Ala Ile
225                 230                 235                 240 ttc aag ccg gtc atg tcc aaa gta atg gag atg ttc cag cct agt gcg      768
Phe Lys Pro Val Met Ser Lys Val Met Glu Met Phe Gln Pro Ser Ala
                245                 250                 255 gtg gtc tta cag tgt ggc tca gac tcc cta tct ggg gat cgg tta ggt      816
Val Val Leu Gln Cys Gly Ser Asp Ser Leu Ser Gly Asp Arg Leu Gly
                260                 265                 270 tgc ttc aat cta act atc aaa gga cac gcc aag tgt gtg gaa ttt gtc      864
Cys Phe Asn Leu Thr Ile Lys Gly His Ala Lys Cys Val Glu Phe Val
            275                 280                 285 aag agc ttt aac ctg cct atg ctg atg ctg gga ggc ggt ggt tac acc      912
Lys Ser Phe Asn Leu Pro Met Leu Met Leu Gly Gly Gly Gly Tyr Thr
        290                 295                 300 att cgt aac gtt gcc cgg tgc tgg aca tat gag aca gct gtg gcc ctg      960
Ile Arg Asn Val Ala Arg Cys Trp Thr Tyr Glu Thr Ala Val Ala Leu
305                 310                 315                 320 gat acg gag atc cct aat gag ctt cca tac aat gac tac ttt gaa tac     1008
Asp Thr Glu Ile Pro Asn Glu Leu Pro Tyr Asn Asp Tyr Phe Glu Tyr
                325                 330                 335 ttt gga cca gat ttc aag ctc cac atc agt cct tcc aat atg act aac     1056
Phe Gly Pro Asp Phe Lys Leu His Ile Ser Pro Ser Asn Met Thr Asn
                340                 345                 350 cag aac acg aat gag tac ctg gag aag atc aaa cag cga ctg ttt gag     1104
Gln Asn Thr Asn Glu Tyr Leu Glu Lys Ile Lys Gln Arg Leu Phe Glu
            355                 360                 365 aac ctt aga atg ctg ccg cac gca cct ggg gtc caa atg cag gcg att     1152
Asn Leu Arg Met Leu Pro His Ala Pro Gly Val Gln Met Gln Ala Ile
        370                 375                 380 cct gag gac gcc atc cct gag gag agt ggc gat gag gac gaa gac gac     1200
Pro Glu Asp Ala Ile Pro Glu Glu Ser Gly Asp Glu Asp Glu Asp Asp
```

```
                385                 390                 395                 400
cct gac aag cgc atc tcg atc tgc tcc tct gac aaa cga att gcc tgt    1248
Pro Asp Lys Arg Ile Ser Ile Cys Ser Ser Asp Lys Arg Ile Ala Cys
                405                 410                 415 gag gaa gag ttc tcc gat tct gaa gag gag gga gag ggg ggc cgc aag    1296
Glu Glu Glu Phe Ser Asp Ser Glu Glu Glu Gly Glu Gly Gly Arg Lys
                420                 425                 430 aac tct tcc aac ttc aaa aaa gcc aag aga gtc aaa aca gag gat gaa    1344
Asn Ser Ser Asn Phe Lys Lys Ala Lys Arg Val Lys Thr Glu Asp Glu
                435                 440                 445 aaa gag aaa gac cca gag gag aag aaa gaa gtc acc gaa gag gag aaa    1392
Lys Glu Lys Asp Pro Glu Glu Lys Lys Glu Val Thr Glu Glu Glu Lys
        450                 455                 460 acc aag gag gag aag cca gaa gcc aaa ggg gtc aag gag gag gtc aag    1440
Thr Lys Glu Glu Lys Pro Glu Ala Lys Gly Val Lys Glu Glu Val Lys
465                 470                 475                 480 ttg gcc tga                                                        1449
Leu Ala

<210> SEQ ID NO 2
<211> LENGTH: 379
<212> TYPE: DNA
<213> ORGANISM: Homo sapiens

<400> SEQUENCE: 2
attgacttcc tgcagagagt cagccccacc aatatgcaag gcttcaccaa gagtcttaat    60
gccttcaacg taggcgatga ctgcccagtg tttcccgggc tctttgagtt ctgctcgcgt   120
tacacaggcg catctctgca aggagcaacc cagctgaaca acaagatctg tgatattgcc   180
attaactggg ctggtggtct gcaccatgcc tagaagtttg aggcctctgg cttctgctat   240
gtcaacgaca ttgtgtttgg catcctggag ctgctcaagt accaccctcg ggtgctctac   300
attgacattg acatccacca tggtgacggg gttcaagaag cttctctacct cactgaccgg   360 gtcatgacgg tgtcctttc                                                379

<210> SEQ ID NO 3
<211> LENGTH: 375
<212> TYPE: DNA
<213> ORGANISM: Homo sapiens

<400> SEQUENCE: 3
tactactgtc tgaacgtgcc cctgcggatg ggcattgatg accagagtta caagcacctt    60
ttccagccgg ttatcaacca ggtagtggac ttctaccaac ccacgtgcat tgtgctccag   120
tgtggagctg actctctggg ctgtgatcga ttgggctgct taacctcag catccgaggg   180 catggggaat gcgttgaata tgtcaagagc ttcaatatcc ctctactcgt gctgggtggt   240
ggtggttata ctgtccgaaa tgttgcccgc tgctggacat atgagacatc gctgctggta   300
gaagaggcca ttagtgagga gcttcccta agtgaatact cgagtactt gccccagac    360 ttcacacttc atcca                                                   375

<210> SEQ ID NO 4
<211> LENGTH: 226
<212> TYPE: DNA
<213> ORGANISM: Homo sapiens

<400> SEQUENCE: 4
ggtcatgcta aatgtgtaga agttgtaaaa acttttaact taccattact gatgcttgga    60
ggaggtggct acacaatccg taatgttgct cgatgttgga catatgagac tgcagttgcc   120
```

```
cttgattgtg agattcccaa tgagttgcca tataatgatt actttgagta ttttggacca    180
gacttcaaac tgcatattag tccttcaaac atgacaacca gaacac                    226
```

<210> SEQ ID NO 5
<211> LENGTH: 482
<212> TYPE: PRT
<213> ORGANISM: Homo sapiens

<400> SEQUENCE: 5

```
Met Ala Gln Thr Gln Gly Thr Arg Arg Lys Val Cys Tyr Tyr Tyr Asp
1               5                   10                  15

Gly Asp Val Gly Asn Tyr Tyr Gly Gln Gly His Pro Met Lys Pro
            20                  25                  30

His Arg Ile Arg Met Thr His Asn Leu Leu Leu Asn Tyr Gly Leu Tyr
        35                  40                  45

Arg Lys Met Glu Ile Tyr Arg Pro His Lys Ala Asn Ala Glu Glu Met
    50                  55                  60

Thr Lys Tyr His Ser Asp Asp Tyr Ile Lys Phe Leu Arg Ser Ile Arg
65                  70                  75                  80

Pro Asp Asn Met Ser Glu Tyr Ser Lys Gln Met Gln Arg Phe Asn Val
                85                  90                  95

Gly Glu Asp Cys Pro Val Phe Asp Gly Leu Phe Glu Phe Cys Gln Leu
            100                 105                 110

Ser Thr Gly Gly Ser Val Ala Ser Ala Val Lys Leu Asn Lys Gln Gln
        115                 120                 125

Thr Asp Ile Ala Val Asn Trp Ala Gly Gly Leu His His Ala Lys Lys
    130                 135                 140

Ser Glu Ala Ser Gly Phe Cys Tyr Val Asn Asp Ile Val Leu Ala Ile
145                 150                 155                 160

Leu Glu Leu Leu Lys Tyr His Gln Arg Val Leu Tyr Ile Asp Ile Asp
                165                 170                 175

Ile His His Gly Asp Gly Val Glu Glu Ala Phe Tyr Thr Thr Asp Arg
            180                 185                 190

Val Met Thr Val Ser Phe His Lys Tyr Gly Glu Tyr Phe Pro Gly Thr
        195                 200                 205

Gly Asp Leu Arg Asp Ile Gly Ala Gly Lys Gly Lys Tyr Tyr Ala Val
    210                 215                 220

Asn Tyr Pro Leu Arg Asp Gly Ile Asp Asp Glu Ser Tyr Glu Ala Ile
225                 230                 235                 240

Phe Lys Pro Val Met Ser Lys Val Met Glu Met Phe Gln Pro Ser Ala
                245                 250                 255

Val Val Leu Gln Cys Gly Ser Asp Ser Leu Ser Gly Asp Arg Leu Gly
            260                 265                 270

Cys Phe Asn Leu Thr Ile Lys Gly His Ala Lys Cys Val Glu Phe Val
        275                 280                 285

Lys Ser Phe Asn Leu Pro Met Leu Met Leu Gly Gly Gly Gly Tyr Thr
    290                 295                 300

Ile Arg Asn Val Ala Arg Cys Trp Thr Tyr Glu Thr Ala Val Ala Leu
305                 310                 315                 320

Asp Thr Glu Ile Pro Asn Glu Leu Pro Tyr Asn Asp Tyr Phe Glu Tyr
                325                 330                 335

Phe Gly Pro Asp Phe Lys Leu His Ile Ser Pro Ser Asn Met Thr Asn
            340                 345                 350

Gln Asn Thr Asn Glu Tyr Leu Glu Lys Ile Lys Gln Arg Leu Phe Glu
```

```
                355                 360                 365
Asn Leu Arg Met Leu Pro His Ala Pro Gly Val Gln Met Gln Ala Ile
            370                 375                 380

Pro Glu Asp Ala Ile Pro Glu Glu Ser Gly Asp Glu Asp Asp
385                 390                 395                 400

Pro Asp Lys Arg Ile Ser Ile Cys Ser Ser Asp Lys Arg Ile Ala Cys
                405                 410                 415

Glu Glu Glu Phe Ser Asp Ser Glu Glu Glu Gly Glu Gly Gly Arg Lys
            420                 425                 430

Asn Ser Ser Asn Phe Lys Lys Ala Lys Arg Val Lys Thr Glu Asp Glu
            435                 440                 445

Lys Glu Lys Asp Pro Glu Glu Lys Glu Val Thr Glu Glu Lys
450                 455                 460

Thr Lys Glu Glu Lys Pro Glu Ala Lys Gly Val Lys Glu Val Lys
465                 470                 475                 480

Leu Ala

<210> SEQ ID NO 6
<211> LENGTH: 133
<212> TYPE: PRT
<213> ORGANISM: Homo sapiens

<400> SEQUENCE: 6

Ile Asp Phe Leu Gln Arg Val Ser Pro Thr Asn Met Gln Gly Phe Thr
1               5                   10                  15

Lys Ser Leu Asn Ala Phe Asn Val Gly Asp Asp Cys Pro Val Phe Pro
            20                  25                  30

Gly Leu Phe Glu Phe Cys Ser Arg Tyr Thr Gly Ala Ser Leu Gln Gly
        35                  40                  45

Ala Thr Gln Leu Asn Asn Lys Ile Cys Asp Ile Ala Ile Asn Trp Ala
    50                  55                  60

Gly Gly Leu His His Ala Lys Lys Phe Glu Ala Ser Gly Phe Cys Tyr
65                  70                  75                  80

Val Asn Asp Ile Val Phe Gly Ile Leu Glu Leu Leu Lys Tyr His Pro
                85                  90                  95

Arg Val Leu Tyr Ile Asp Ile Asp Ile His His Gly Asp Gly Val Gln
            100                 105                 110

Glu Ala Phe Tyr Leu Thr Asp Arg Val Met Thr Val Ser Phe Pro Gln
        115                 120                 125

Ile Arg Glu Ile Tyr
        130

<210> SEQ ID NO 7
<211> LENGTH: 125
<212> TYPE: PRT
<213> ORGANISM: Homo sapiens

<400> SEQUENCE: 7

Tyr Tyr Cys Leu Asn Val Pro Leu Arg Met Gly Ile Asp Asp Gln Ser
1               5                   10                  15

Tyr Lys His Leu Phe Gln Pro Val Ile Asn Gln Val Val Asp Phe Tyr
            20                  25                  30

Gln Pro Thr Cys Ile Val Leu Gln Cys Gly Ala Asp Ser Leu Gly Cys
        35                  40                  45

Asp Arg Leu Gly Cys Phe Asn Leu Ser Ile Arg Gly His Gly Glu Cys
    50                  55                  60
```

```
Val Glu Tyr Val Lys Ser Phe Asn Ile Pro Leu Leu Val Leu Gly Gly
 65                  70                  75                  80

Gly Gly Tyr Thr Val Arg Asn Val Ala Arg Cys Trp Thr Tyr Glu Thr
                 85                  90                  95

Ser Leu Leu Val Glu Glu Ala Ile Ser Glu Glu Leu Pro Tyr Ser Glu
                100                 105                 110

Tyr Phe Glu Tyr Phe Ala Pro Asp Phe Thr Leu His Pro
            115                 120                 125

<210> SEQ ID NO 8
<211> LENGTH: 80
<212> TYPE: PRT
<213> ORGANISM: Homo sapiens

<400> SEQUENCE: 8

Asn Leu Leu Val Leu Gly His Ala Lys Cys Val Glu Val Val Lys Thr
 1               5                  10                  15

Phe Asn Leu Pro Leu Leu Met Leu Gly Gly Gly Tyr Thr Ile Arg
                 20                  25                  30

Asn Val Ala Arg Cys Trp Thr Tyr Glu Thr Ala Val Ala Leu Asp Cys
             35                  40                  45

Glu Ile Pro Asn Glu Leu Pro Tyr Asn Asp Tyr Phe Glu Tyr Phe Gly
     50                  55                  60

Pro Asp Phe Lys Leu His Ile Ser Pro Ser Asn Met Thr Asn Gln Asn
 65                  70                  75                  80

<210> SEQ ID NO 9
<211> LENGTH: 432
<212> TYPE: PRT
<213> ORGANISM: Saccharomyces cerevisiae

<400> SEQUENCE: 9

Met Val Tyr Glu Ala Thr Pro Phe Asp Pro Ile Thr Val Lys Pro Ser
 1               5                  10                  15

Asp Lys Arg Arg Val Ala Tyr Phe Tyr Asp Ala Asp Val Gly Asn Tyr
                 20                  25                  30

Ala Tyr Gly Ala Gly His Pro Met Lys Pro His Arg Ile Arg Met Ala
             35                  40                  45

His Ser Leu Ile Met Asn Tyr Gly Leu Tyr Lys Lys Met Glu Ile Tyr
     50                  55                  60

Arg Ala Lys Pro Ala Thr Lys Gln Glu Met Cys Gln Phe His Thr Asp
 65                  70                  75                  80

Glu Tyr Ile Asp Phe Leu Ser Arg Val Thr Pro Asp Asn Leu Glu Met
                 85                  90                  95

Phe Lys Arg Glu Ser Val Lys Phe Asn Val Gly Asp Asp Cys Pro Val
                100                 105                 110

Phe Asp Gly Leu Tyr Glu Tyr Cys Ser Ile Ser Gly Gly Gly Ser Met
            115                 120                 125

Glu Gly Ala Ala Arg Leu Asn Arg Gly Lys Cys Asp Val Ala Val Asn
130                 135                 140

Tyr Ala Gly Gly Leu His His Ala Lys Lys Ser Glu Ala Ser Gly Phe
145                 150                 155                 160

Cys Tyr Leu Asn Asp Ile Val Leu Gly Ile Ile Glu Leu Leu Arg Tyr
                165                 170                 175

His Pro Arg Val Leu Tyr Ile Asp Ile Asp Val His His Gly Asp Gly
                180                 185                 190

Val Glu Glu Ala Phe Tyr Thr Thr Asp Arg Val Met Thr Cys Ser Phe
```

His Lys Tyr Gly Glu Phe Phe Pro Gly Thr Gly Glu Leu Arg Asp Ile
195                 200                 205
                                                        210
Gly Val Gly Ala Gly Lys Asn Tyr Ala Val Asn Val Pro Leu Arg Asp
225                 230                 235                 240
Gly Ile Asp Asp Ala Thr Tyr Arg Ser Val Phe Glu Pro Val Ile Lys
                        245                 250                 255
Lys Ile Met Glu Trp Tyr Gln Pro Ser Ala Val Val Leu Gln Cys Gly
                260                 265                 270
Gly Asp Ser Leu Ser Gly Asp Arg Leu Gly Cys Phe Asn Leu Ser Met
                275                 280                 285
Glu Gly His Ala Asn Cys Val Asn Tyr Val Lys Ser Phe Gly Ile Pro
                290                 295                 300
Met Met Val Val Gly Gly Gly Gly Tyr Thr Met Arg Asn Val Ala Arg
305                 310                 315                 320
Thr Trp Cys Phe Glu Thr Gly Leu Leu Asn Asn Val Val Leu Asp Lys
                        325                 330                 335
Asp Leu Pro Tyr Asn Glu Tyr Tyr Glu Tyr Tyr Gly Pro Asp Tyr Lys
                        340                 345                 350
Leu Ser Val Arg Pro Ser Asn Met Phe Asn Val Asn Thr Pro Glu Tyr
                355                 360                 365
Leu Asp Lys Val Met Thr Asn Ile Phe Ala Asn Leu Glu Asn Thr Lys
370                 375                 380
Tyr Ala Pro Ser Val Gln Leu Asn His Thr Pro Arg Asp Ala Glu Asp
385                 390                 395                 400
Leu Gly Asp Val Glu Glu Asp Ser Ala Glu Ala Lys Asp Thr Lys Gly
                        405                 410                 415
Gly Ser Gln Tyr Ala Arg Asp Leu His Val Glu His Asp Asn Glu Phe
                        420                 425                 430

<210> SEQ ID NO 10
<211> LENGTH: 480
<212> TYPE: PRT
<213> ORGANISM: Xenopus laevis

<400> SEQUENCE: 10

Met Ala Leu Thr Leu Gly Thr Lys Lys Val Cys Tyr Tyr Tyr Asp
1               5                   10                  15

Gly Asp Val Gly Asn Tyr Tyr Gly Gln Gly His Pro Met Lys Pro
                20                  25                  30

His Arg Ile Arg Met Thr His Asn Leu Leu Leu Asn Tyr Gly Leu Tyr
                35                  40                  45

Arg Lys Met Glu Ile Phe Arg Pro His Lys Ala Ser Ala Glu Asp Met
                50                  55                  60

Thr Lys Tyr His Ser Asp Asp Tyr Ile Lys Phe Leu Arg Ser Ile Arg
65                  70                  75                  80

Pro Asp Asn Met Ser Glu Tyr Ser Lys Gln Met Gln Arg Phe Asn Val
                        85                  90                  95

Gly Glu Asp Cys Pro Val Phe Asp Gly Leu Phe Glu Phe Cys Gln Leu
                100                 105                 110

Ser Ala Gly Gly Ser Val Ala Ser Ala Val Lys Leu Asn Lys Gln Gln
                115                 120                 125

Thr Asp Ile Ser Val Asn Trp Ser Gly Gly Leu His His Ala Lys Lys
                130                 135                 140

Ser Glu Ala Ser Gly Phe Cys Tyr Val Asn Asp Ile Val Leu Ala Ile

```
                145                 150                 155                 160
Leu Glu Leu Leu Lys Tyr His Gln Arg Val Val Tyr Ile Asp Ile Asp
                    165                 170                 175

Ile His His Gly Asp Gly Val Glu Glu Ala Phe Tyr Thr Thr Asp Arg
                180                 185                 190

Val Met Thr Val Ser Phe His Lys Tyr Gly Glu Tyr Phe Pro Gly Thr
            195                 200                 205

Gly Asp Leu Arg Asp Ile Gly Ala Gly Lys Gly Lys Tyr Tyr Ala Val
        210                 215                 220

Asn Tyr Ala Leu Arg Asp Gly Ile Asp Asp Glu Ser Tyr Glu Ala Ile
225                 230                 235                 240

Phe Lys Pro Val Met Ser Lys Val Met Glu Met Phe Gln Pro Ser Ala
                245                 250                 255

Val Val Leu Gln Cys Gly Ala Asp Ser Leu Ser Gly Asp Arg Leu Gly
                260                 265                 270

Cys Phe Asn Leu Thr Ile Lys Gly His Ala Lys Cys Val Glu Phe Ile
            275                 280                 285

Lys Thr Phe Asn Leu Pro Leu Leu Met Leu Gly Gly Gly Gly Tyr Thr
        290                 295                 300

Ile Arg Asn Val Ala Arg Cys Trp Thr Tyr Glu Thr Ala Val Ala Leu
305                 310                 315                 320

Asp Ser Glu Ile Pro Asn Glu Leu Pro Tyr Asn Asp Tyr Phe Glu Tyr
                325                 330                 335

Phe Gly Pro Asp Phe Lys Leu His Ile Ser Pro Ser Asn Met Thr Asn
                340                 345                 350

Gln Asn Thr Asn Glu Tyr Leu Glu Lys Ile Lys Gln Arg Leu Phe Glu
            355                 360                 365

Asn Leu Arg Met Leu Pro His Ala Pro Gly Val Gln Met Gln Ala Val
        370                 375                 380

Ala Glu Asp Ser Ile His Asp Asp Ser Gly Glu Glu Asp Glu Asp Asp
385                 390                 395                 400

Pro Asp Lys Arg Ile Ser Ile Arg Ser Ser Asp Lys Arg Ile Ala Cys
                405                 410                 415

Asp Glu Glu Phe Ser Asp Ser Glu Asp Glu Gly Glu Gly Gly Arg Lys
                420                 425                 430

Asn Val Ala Asn Phe Lys Lys Val Lys Arg Val Lys Thr Glu Glu Glu
            435                 440                 445

Lys Glu Gly Glu Asp Lys Lys Asp Val Lys Glu Glu Lys Ala Lys
        450                 455                 460

Asp Glu Lys Thr Asp Ser Lys Arg Val Lys Glu Glu Thr Lys Ser Val
465                 470                 475                 480

<210> SEQ ID NO 11
<211> LENGTH: 1278
<212> TYPE: DNA
<213> ORGANISM: Homo sapiens
<220> FEATURE:
<221> NAME/KEY: CDS
<222> LOCATION: (1)..(1278)

<400> SEQUENCE: 11 atg gcc gac aag gaa gca gcc ttc gac gac gca gtg gaa gaa cga gtg      48
Met Ala Asp Lys Glu Ala Ala Phe Asp Asp Ala Val Glu Glu Arg Val
1               5                   10                  15 atc aac gag gaa tac aaa ata tgg aaa aag aac acc cct ttt ctt tat      96
Ile Asn Glu Glu Tyr Lys Ile Trp Lys Lys Asn Thr Pro Phe Leu Tyr
            20                  25                  30
```

```
gat ttg gtg atg acc cat gct ctg gag tgg ccc agc cta act gcc cag      144
Asp Leu Val Met Thr His Ala Leu Glu Trp Pro Ser Leu Thr Ala Gln
         35                  40                  45 tgg ctt cca gat gta acc aga cca gaa ggg aaa gat ttc agc att cat      192
Trp Leu Pro Asp Val Thr Arg Pro Glu Gly Lys Asp Phe Ser Ile His
 50                  55                  60 cga ctt gtc ctg ggg aca cac aca tcg gat gaa caa aac cat ctt gtt      240
Arg Leu Val Leu Gly Thr His Thr Ser Asp Glu Gln Asn His Leu Val
 65                  70                  75                  80 ata gcc agt gtg cag ctc cct aat gat gat gct cag ttt gat gcg tca      288
Ile Ala Ser Val Gln Leu Pro Asn Asp Asp Ala Gln Phe Asp Ala Ser
                 85                  90                  95 cac tac gac agt gag aaa gga gaa ttt gga ggt ttt ggt tca gtt agt      336
His Tyr Asp Ser Glu Lys Gly Glu Phe Gly Gly Phe Gly Ser Val Ser
            100                 105                 110 gga aaa att gaa ata gaa atc aag atc aac cat gaa gga gaa gta aac      384
Gly Lys Ile Glu Ile Glu Ile Lys Ile Asn His Glu Gly Glu Val Asn
        115                 120                 125 agg gcc cgt tat atg ccc cag aac cct tgt atc atc gca aca aag act      432
Arg Ala Arg Tyr Met Pro Gln Asn Pro Cys Ile Ile Ala Thr Lys Thr
130                 135                 140 cct tcc agt gat gtt ctt gtc ttt gac tat aca aaa cat cct tct aaa      480
Pro Ser Ser Asp Val Leu Val Phe Asp Tyr Thr Lys His Pro Ser Lys
145                 150                 155                 160 cca gat cct tct gga gag tgc aac cca gac ttg cgt ctc cgt gga cat      528
Pro Asp Pro Ser Gly Glu Cys Asn Pro Asp Leu Arg Leu Arg Gly His
                165                 170                 175 cag aag gaa ggc tat ggg ctt tct tgg aac cca aat ctc agt ggg cac      576
Gln Lys Glu Gly Tyr Gly Leu Ser Trp Asn Pro Asn Leu Ser Gly His
            180                 185                 190 tta ctt agt gct tca gat gac cat acc atc tgc ctg tgg gac atc agt      624
Leu Leu Ser Ala Ser Asp Asp His Thr Ile Cys Leu Trp Asp Ile Ser
        195                 200                 205 gcc gtt cca aag gag gga aaa gtg gta gat gcg aag acc atc ttt aca      672
Ala Val Pro Lys Glu Gly Lys Val Val Asp Ala Lys Thr Ile Phe Thr
    210                 215                 220 ggg cat acg gca gta gta gaa gat gtt tcc tgg cat cta ctc cat gag      720
Gly His Thr Ala Val Val Glu Asp Val Ser Trp His Leu Leu His Glu
225                 230                 235                 240 tct ctg ttt ggg tca gtt gct gat gat cag aaa ctt atg att tgg gat      768
Ser Leu Phe Gly Ser Val Ala Asp Asp Gln Lys Leu Met Ile Trp Asp
                245                 250                 255 act cgt tca aac aat act tcc aaa cca agc cac tca gtt gat gct cac      816
Thr Arg Ser Asn Asn Thr Ser Lys Pro Ser His Ser Val Asp Ala His
            260                 265                 270 act gct gaa gtg aac tgc ctt tct ttc aat cct tat agt gag ttc att      864
Thr Ala Glu Val Asn Cys Leu Ser Phe Asn Pro Tyr Ser Glu Phe Ile
        275                 280                 285 ctt gcc aca gga tca gct gac aag act gtt gcc ttg tgg gat ctg aga      912
Leu Ala Thr Gly Ser Ala Asp Lys Thr Val Ala Leu Trp Asp Leu Arg
    290                 295                 300 aat ctg aaa ctt aag ttg cat tcc ttt gag tca cat aag gat gaa ata      960
Asn Leu Lys Leu Lys Leu His Ser Phe Glu Ser His Lys Asp Glu Ile
305                 310                 315                 320 ttc cag gtt cag tgg tca cct cac aat gag act att tta gct tcc agt     1008
Phe Gln Val Gln Trp Ser Pro His Asn Glu Thr Ile Leu Ala Ser Ser
                325                 330                 335 ggt act gat cgc aga ctg aat gtc tgg gat tta agt aaa att gga gag     1056
Gly Thr Asp Arg Arg Leu Asn Val Trp Asp Leu Ser Lys Ile Gly Glu
            340                 345                 350
```

-continued

```
gaa caa tcc cca gaa gat gca gaa gac ggg cca cca gag ttg ttg ttt    1104
Glu Gln Ser Pro Glu Asp Ala Glu Asp Gly Pro Pro Glu Leu Leu Phe
        355                 360                 365 att cat ggt ggt cat act gcc aag ata tct gat ttc tcc tgg aat ccc    1152
Ile His Gly Gly His Thr Ala Lys Ile Ser Asp Phe Ser Trp Asn Pro
370                 375                 380 aat gaa cct tgg gtg att tgt tct gta tca gaa gac aat atc atg caa    1200
Asn Glu Pro Trp Val Ile Cys Ser Val Ser Glu Asp Asn Ile Met Gln
385                 390                 395                 400 gtg tgg caa atg gca gag aac att tat aat gat gaa gac cct gaa gga    1248
Val Trp Gln Met Ala Glu Asn Ile Tyr Asn Asp Glu Asp Pro Glu Gly
                405                 410                 415 agc gtg gat cca gaa gga caa ggg tcc tag                            1278
Ser Val Asp Pro Glu Gly Gln Gly Ser
                420                 425

<210> SEQ ID NO 12
<211> LENGTH: 66
<212> TYPE: PRT
<213> ORGANISM: Artificial Sequence
<220> FEATURE:
<223> OTHER INFORMATION: Synthetic motif consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
```

```
<220> FEATURE:
<221> NAME/KEY: misc_feature
<222> LOCATION: (64)..(64)
<223> OTHER INFORMATION: Xaa can be any naturally occurring amino acid

<400> SEQUENCE: 12

Asp Xaa Xaa Asn Xaa Gly Gly Leu His His Ala Lys Lys Xaa Glu Ala
1               5                   10                  15

Ser Gly Phe Cys Tyr Xaa Asn Asp Ile Val Xaa Xaa Ile Xaa Glu Leu
            20                  25                  30

Leu Xaa Tyr His Xaa Arg Val Xaa Tyr Ile Asp Xaa Asp Xaa His His
        35                  40                  45

Gly Asp Gly Xaa Glu Ala Phe Tyr Xaa Thr Asp Arg Val Met Thr Xaa
    50                  55                  60

Ser Phe
65

<210> SEQ ID NO 13
<211> LENGTH: 68
<212> TYPE: PRT
<213> ORGANISM: Artificial Sequence
<220> FEATURE:
<223> OTHER INFORMATION: Synthetic motif consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 13

Asp Ile Ala Xaa Asn Trp Ala Gly Gly Leu His His Ala Lys Lys Xaa
1               5                   10                  15

Glu Ala Ser Gly Phe Cys Tyr Val Asn Asp Ile Val Xaa Xaa Ile Leu
            20                  25                  30

Glu Leu Leu Lys Tyr His Xaa Arg Val Leu Tyr Ile Asp Ile Asp Ile
        35                  40                  45

His His Gly Asp Gly Xaa Glu Ala Phe Tyr Xaa Thr Asp Arg Val Met
    50                  55                  60

Thr Val Ser Phe
65

<210> SEQ ID NO 14
<211> LENGTH: 33
<212> TYPE: PRT
<213> ORGANISM: Artificial Sequence
<220> FEATURE:
<223> OTHER INFORMATION: Synthetic motif consensus sequence
<220> FEATURE:
<221> NAME/KEY: misc_feature
```

```
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid

<400> SEQUENCE: 14

Cys Val Xaa Xaa Xaa Lys Xaa Phe Xaa Xaa Pro Xaa Xaa Xaa Xaa Gly
1               5                   10                  15

Gly Gly Gly Tyr Thr Xaa Arg Asn Val Ala Arg Xaa Trp Xaa Xaa Glu
            20                  25                  30

Thr

<210> SEQ ID NO 15
<211> LENGTH: 33
<212> TYPE: PRT
<213> ORGANISM: Artificial Sequence
<220> FEATURE:
<223> OTHER INFORMATION: Synthetic motif consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 15

Cys Val Glu Xaa Val Lys Xaa Phe Asn Xaa Pro Leu Leu Xaa Leu Gly
1               5                   10                  15

Gly Gly Gly Tyr Thr Xaa Arg Asn Val Ala Arg Cys Trp Thr Tyr Glu
            20                  25                  30

Thr

<210> SEQ ID NO 16
<211> LENGTH: 33
<212> TYPE: PRT
<213> ORGANISM: Artificial Sequence
```

```
<220> FEATURE:
<223> OTHER INFORMATION: Synthetic motif consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 16

Cys Val Glu Xaa Val Lys Xaa Phe Asn Xaa Pro Xaa Leu Xaa Leu Gly
1               5                   10                  15

Gly Gly Gly Tyr Thr Xaa Arg Asn Val Ala Arg Cys Trp Thr Tyr Glu
            20                  25                  30

Thr

<210> SEQ ID NO 17
<211> LENGTH: 425
<212> TYPE: PRT
<213> ORGANISM: Homo sapiens

<400> SEQUENCE: 17

Met Ala Asp Lys Glu Ala Ala Phe Asp Asp Ala Val Glu Glu Arg Val
1               5                   10                  15

Ile Asn Glu Glu Tyr Lys Ile Trp Lys Lys Asn Thr Pro Phe Leu Tyr
            20                  25                  30

Asp Leu Val Met Thr His Ala Leu Glu Trp Pro Ser Leu Thr Ala Gln
        35                  40                  45

Trp Leu Pro Asp Val Thr Arg Pro Glu Gly Lys Asp Phe Ser Ile His
    50                  55                  60

Arg Leu Val Leu Gly Thr His Thr Ser Asp Glu Gln Asn His Leu Val
65                  70                  75                  80

Ile Ala Ser Val Gln Leu Pro Asn Asp Asp Ala Gln Phe Asp Ala Ser
                85                  90                  95

His Tyr Asp Ser Glu Lys Gly Glu Phe Gly Gly Phe Gly Ser Val Ser
            100                 105                 110

Gly Lys Ile Glu Ile Glu Ile Lys Ile Asn His Glu Gly Glu Val Asn
        115                 120                 125

Arg Ala Arg Tyr Met Pro Gln Asn Pro Cys Ile Ile Ala Thr Lys Thr
    130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190
```

```
Leu Leu Ser Ala Ser Asp Asp His Thr Ile Cys Leu Trp Asp Ile Ser
        195                 200                 205

Ala Val Pro Lys Glu Gly Lys Val Asp Ala Lys Thr Ile Phe Thr
    210                 215                 220

Gly His Thr Ala Val Glu Asp Val Ser Trp His Leu Leu His Glu
225                 230                 235                 240

Ser Leu Phe Gly Ser Val Ala Asp Asp Gln Lys Leu Met Ile Trp Asp
                245                 250                 255

Thr Arg Ser Asn Asn Thr Ser Lys Pro Ser His Ser Val Asp Ala His
            260                 265                 270

Thr Ala Glu Val Asn Cys Leu Ser Phe Asn Pro Tyr Ser Glu Phe Ile
        275                 280                 285

Leu Ala Thr Gly Ser Ala Asp Lys Thr Val Ala Leu Trp Asp Leu Arg
    290                 295                 300

Asn Leu Lys Leu Lys Leu His Ser Phe Glu Ser His Lys Asp Glu Ile
305                 310                 315                 320

Phe Gln Val Gln Trp Ser Pro His Asn Glu Thr Ile Leu Ala Ser Ser
                325                 330                 335

Gly Thr Asp Arg Arg Leu Asn Val Trp Asp Leu Ser Lys Ile Gly Glu
            340                 345                 350

Glu Gln Ser Pro Glu Asp Ala Glu Asp Gly Pro Pro Glu Leu Leu Phe
        355                 360                 365

Ile His Gly Gly His Thr Ala Lys Ile Ser Asp Phe Ser Trp Asn Pro
    370                 375                 380

Asn Glu Pro Trp Val Ile Cys Ser Val Ser Glu Asp Asn Ile Met Gln
385                 390                 395                 400

Val Trp Gln Met Ala Glu Asn Ile Tyr Asn Asp Glu Asp Pro Glu Gly
                405                 410                 415

Ser Val Asp Pro Glu Gly Gln Gly Ser
            420                 425

<210> SEQ ID NO 18
<211> LENGTH: 383
<212> TYPE: DNA
<213> ORGANISM: Unknown
<220> FEATURE:
<223> OTHER INFORMATION: R18769 nucleotide sequence
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (328)..(328)
```

```
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t

<400> SEQUENCE: 18
cgatgactgc ccagtgtttc ccgggctctt tgagttctgc tcgcgttaca caggcgcatc      60
tctgcaagga gcaacccagc tgaacaacaa gatctgtgat attgccatta acttggctgg     120
tggcttnaac natgccanga ngtttnaggc ctctggnttc tgctatgtca acgacattgt     180
gattggcatc ctggagctgc tcaagtacca ccctcgggtg ctctacattg acattgacat     240
ccaccatggt gacggggttc aagaagcttt ctacctcact gaccgggtca tgacggtgtc     300
ctttccacaa atacgggaaa tttacttntt ccngggcac aggtgacatg ttntggaagt      360 tcgggggca ggagagttgg ccc                                              383

<210> SEQ ID NO 19
<211> LENGTH: 213
<212> TYPE: DNA
<213> ORGANISM: Unknown
<220> FEATURE:
<223> OTHER INFORMATION: R31480 nucleotide sequence
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 19
atggcgcaga cgcagggcac ccggaggaaa gtntgttact actacgacgg ggatgttgga      60
aattactatt atggacaagg ccacccaatg aagcctcacc gaatccgcat gactcataat     120
ttgctgctca actatggtct ctaccgaaaa atggaaatct atcgncctca caaagccaat     180
nctgaggaga tgaccaagta ncacagcgat gac                                   213

<210> SEQ ID NO 20
<211> LENGTH: 313
<212> TYPE: DNA
<213> ORGANISM: Unknown
<220> FEATURE:
<223> OTHER INFORMATION: R98879 nucleotide sequence
<220> FEATURE:
<221> NAME/KEY: misc_feature
<222> LOCATION: (189)..(189)
<223> OTHER INFORMATION: n is a, c, g, or t

<400> SEQUENCE: 20
tcctgcagag agtcagcccc accaatatgc aaggcttcac caagagtctt aatgccttca      60
acgtaggcga tgactgccca gtgtttcccg ggctctttga gttctgctcg cgttacacag     120
gcgcatctct gcaaggagca acccagctga acaacaagat ctgtgatatt gccattaact     180
```

```
gggctggtng tctgcaccat gccaagaagt ttgaggcctc tggtttctgc tatgtcaacg    240
acattgtgat tggcatcctg gagctgctca agtaccaccc tcgggtgctc tacattgaca    300
ttgacatcca cca                                                        313
```

```
<210> SEQ ID NO 21
<211> LENGTH: 370
<212> TYPE: DNA
<213> ORGANISM: Unknown
<220> FEATURE:
<223> OTHER INFORMATION: N59055 nucleotide sequence
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t

<400> SEQUENCE: 21
ccctatagtg agtcgtattn ntnaaaacat gactcactng gntnnntacg attgggctgc     60
tttaacctca gcatccgagg gcatgggnaa tgcgttgaat atgtcaagag cttcaatatc    120
cctctactcg tgctgggtgg tggtggttat actgtccgaa atgtngcccg ctgctggaca    180
tatgagacan cgctgctggt agaagaggcc attagtgagg agcttcccta atagtgaata    240
cttcgntact ttgccccaga cttcacactt catccanatg tcagcacccg catcgagaat    300
ccagaactca cgccagtatc nggaccaaga tccgccagac aatctttgna aacctgaagg    360
```

```
<210> SEQ ID NO 22
<211> LENGTH: 177
<212> TYPE: DNA
<213> ORGANISM: Unknown
<220> FEATURE:
<223> OTHER INFORMATION: F06693 nucleotide sequence
<220> FEATURE:
<221> NAME/KEY: misc_feature
<222> LOCATION: (5)..(5)
<223> OTHER INFORMATION: n is a, c, g, or t

<400> SEQUENCE: 22
aggtnatgct aaatgtgtag aagttgtaaa aacttttaac ttaccattac tgatgcttgg      60
aggaggtggc tacacaatcc gtaatgttgc tcgatgttgg acatatgaga ctgcagttgc     120
ccttgattgt gagattccca atggtaagtg ttctcattac aatatcttta ttgtatg       177

<210> SEQ ID NO 23
<211> LENGTH: 208
<212> TYPE: DNA
<213> ORGANISM: Unknown
<220> FEATURE:
<223> OTHER INFORMATION: H05234 nucleotide sequence
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 23
ctacaccacg gaccgggtca tgactgtgtc ctttcataag tatggagagt acttcccagg      60
gacttgggac ctacgggata tcggggctgg caaaggcaag tattatgctg ttaactaccc     120
gctccgagac gggattnatg acgagtccta tgaggccatt ttcaagccgg tcatgtccaa     180
agtaatngag atgttccagc ctagtgcg                                         208
```